United States Patent
Draghia-Akli et al.

(10) Patent No.: US 7,846,720 B2
(45) Date of Patent: Dec. 7, 2010

(54) OPTIMIZED HIGH YIELD SYNTHETIC PLASMIDS

(75) Inventors: Ruxandra Draghia-Akli, Houston, TX (US); Melissa Pope, The Woodlands, TX (US)

(73) Assignee: VGX Pharmaceuticals, Inc., Blue Bell, PA (US)

( * ) Notice: Subject to any disclaimer, the term of this patent is extended or adjusted under 35 U.S.C. 154(b) by 635 days.

(21) Appl. No.: 11/339,894

(22) Filed: Jan. 26, 2006

(65) Prior Publication Data

US 2006/0188988 A1 Aug. 24, 2006

Related U.S. Application Data

(60) Provisional application No. 60/647,170, filed on Jan. 26, 2005.

(51) Int. Cl.
C12N 15/79 (2006.01)
C07H 21/04 (2006.01)

(52) U.S. Cl. .................... 435/320.1; 536/23.1

(58) Field of Classification Search .......... 435/320.1; 536/23.1
See application file for complete search history.

(56) References Cited

U.S. PATENT DOCUMENTS

| | | | |
|---|---|---|---|
| 4,822,470 A | 4/1989 | Chang | |
| 4,970,154 A | 11/1990 | Chang | |
| 5,061,690 A | 10/1991 | Kann et al. | |
| 5,134,120 A | 7/1992 | Boyd et al. | |
| 5,292,721 A | 3/1994 | Boyd et al. | |
| 5,298,422 A | 3/1994 | Schwartz et al. | |
| 5,304,486 A | 4/1994 | Chang | |
| 5,364,791 A | 11/1994 | Vegeto et al. | |
| 5,374,544 A | 12/1994 | Schwartz et al. | |
| 5,756,264 A | 5/1998 | Schwartz et al. | |
| 5,874,534 A | 2/1999 | Vegeto et al. | |
| 5,925,564 A | 7/1999 | Schwartz et al. | |
| 5,935,934 A | 8/1999 | Vegeto et al. | |
| 6,040,295 A | 3/2000 | Rolland et al. | |
| 6,114,148 A | 9/2000 | Seed et al. | |
| 6,410,228 B1 | 6/2002 | Schwartz et al. | |
| 6,423,693 B1 | 7/2002 | Schwartz et al. | |
| 6,551,996 B1 | 4/2003 | Schwartz et al. | |
| 7,316,925 B2* | 1/2008 | Draghia-Akli et al. | ... 435/320.1 |
| 2003/0074679 A1 | 4/2003 | Schwartz et al. | |
| 2003/0157717 A1 | 8/2003 | Draghia-Akli | |
| 2004/0014645 A1 | 1/2004 | Draghia-Akli et al. | |
| 2004/0038918 A1 | 2/2004 | Draghia-Akli et al. | |
| 2004/0057941 A1 | 3/2004 | Draghia-Akli et al. | |
| 2004/0092009 A1* | 5/2004 | Draghia-Akli et al. | ... 435/320.1 |
| 2004/0138111 A1 | 7/2004 | Draghia-Akli et al. | |
| 2004/0167458 A1 | 8/2004 | Draghia-Akli et al. | |
| 2004/0175727 A1 | 9/2004 | Draghia-Akli et al. | |
| 2004/0192593 A1 | 9/2004 | Draghia-Akli et al. | |
| 2004/0204358 A1 | 10/2004 | Brown et al. | |
| 2005/0004060 A1 | 1/2005 | Draghia-Akli et al. | |
| 2005/0014245 A1 | 1/2005 | Hebel et al. | |
| 2005/0032737 A1 | 2/2005 | Draghia-Akli | |
| 2005/0052630 A1 | 3/2005 | Smith et al. | |
| 2005/0171046 A1 | 8/2005 | Draghia-Akli et al. | |
| 2005/0182014 A1 | 8/2005 | Draghia-Akli et al. | |
| 2005/0238624 A1 | 10/2005 | Rabinovsky et al. | |
| 2006/0025368 A1* | 2/2006 | Draghia-Akli et al. | ........ 514/44 |

FOREIGN PATENT DOCUMENTS

| | | |
|---|---|---|
| AU | 772752 | 2/2001 |
| AU | 200197157 A1 | 2/2002 |

OTHER PUBLICATIONS

CVU47122, 1996.*
1994, AAA52609.*
Seyfang et al, Analy. Biochem. 324:285-291, 2004.*
U.S. Appl. No. 60/590,739, filed Jul. 23, 2004, Draghia-Akli et al.
Acsadi G, Dickson G, Love DR, Jani A, Walsh FS, Gurusinghe A, Wolff JA, Davies KE. Human dystrophin expression in mdx mice after intramuscular injection of DNA constructs. Nature. Aug. 29, 1991;352(6338):757-8.
Aihara H, Miyazaki J. Gene transfer into muscle by electroporation in vivo. Nat Biotechnol. Jun. 1999;17(6):517.
Almendro N, Bellon T, Rius C, Lastres P, Langa C, Corbi A, Bernabeu C. Cloning of the human platelet endothelial cell adhesion molecule-1 promoter and its tissue-specific expression. Structural and functional characterization. J Immunol. Dec. 15, 1996;157(12):5411-21.
Aratani Y, Okazaki R, Koyama H. End extension repair of introduced targeting vectors mediated by homologous recombination in mammalian cells. Nucleic Acids Res. Sep. 25, 1992;20(18):4795-801.

(Continued)

*Primary Examiner*—Kevin K. Hill
(74) *Attorney, Agent, or Firm*—Thomas Kim

(57) ABSTRACT

One aspect of the current invention is an optimized synthetic mammalian expression plasmid with a mutated origin of replication (e.g. "mut" family of plasmids). This new plasmid comprises a therapeutic element, and a replication element. The therapeutic element of the new plasmid comprises a eukaryotic promoter; a 5' untranslated region ("UTR"); a codon-optimized-eukaryotic therapeutic gene sequence; and a poly adenylation signal. The therapeutic elements of this plasmid are operatively linked and located in a first operatively-linked arrangement. Additionally, the optimized synthetic mammalian expression plasmid comprises replication elements, wherein the replication elements are operatively linked and located in a second operatively-linked arrangement. The replication elements comprise a selectable marker gene promoter, a ribosomal binding site, a selectable marker gene sequence, and an improved origin of replication. The first-operatively-linked arrangement and the second-operatively-linked arrangement comprise a circular structure of the codon optimized synthetic mammalian expression plasmid.

2 Claims, 10 Drawing Sheets

OTHER PUBLICATIONS

Babiuk LA, Pontarollo R, Babiuk S, Loehr B, van Drunen Littel-van den Hurk S. Induction of immune responses by DNA vaccines in large animals. Vaccine. Jan. 30, 2003;21(7-8):649-58.

Bert AG, Burrows J, Osborne CS, Cockerill PN. Generation of an improved luciferase reporter gene plasmid that employs a novel mechanism for high-copy replication. Plasmid. Sep. 2000;44(2):173-82.

Bettan M, Emmanuel F, Darteil R, Caillaud JM, Soubrier F, Delaere P, Branelec D, Mahfoudi A, Duverger N, Scherman D. High-level protein secretion into blood circulation after electric pulse-mediated gene transfer into skeletal muscle. Mol Ther. Sep. 2000;2(3):204-10.

Boshart M, Weber F, Jahn G, Dorsch-Hasler K, Fleckenstein B, Schaffner W. A very strong enhancer is located upstream of an immediate early gene of human cytomegalovirus. Cell. Jun. 1985;41(2):521-30.

Brown PA, Davis WC, Draghia-Akli R. Immune-enhancing effects of growth hormone-releasing hormone delivered by plasmid injection and electroporation. Mol Ther. Oct. 2004;10(4):644-51.

Bujard H, Baldari C, Brunner M, Deuschle U, Gentz R, Hughes J, Kammerer W, Stuber D. Integration of efficient promoters of the *E. coli* system into plasmid vectors. Gene Amplif Anal. 1983;3:65-87.

Carbonelli DL, Corley E, Seigelchifer M, Zorzopulos J. A plasmid vector for isolation of strong promoters in *Escherichia coli*. FEMS Microbiol Lett. Aug. 1, 1999;177(1):75-82.

Chandler SD, Mayeda A, Yeakley JM, Krainer AR, Fu XD RNA splicing specificity determined by the coordinated action of RNA recognition motifs in SR proteins. Proc Natl Acad Sci U S A. Apr. 15, 1997;94(8):3596-601.

Cocea L. Duplication of a region in the multiple cloning site of a plasmid vector to enhance cloning-mediated addition of restriction sites to a DNA fragment. Biotechniques. Nov. 1997;23(5):814-6.

Dai B, Wu H, Holthuizen E, Singh P. Identification of a novel cis element required for cell density-dependent down-regulation of insulin-like growth factor-2 P3 promoter activity in Caco2 cells. J Biol Chem. Mar. 9, 2001;276(10):6937-44. Epub Dec. 8, 2000.

Danko I, Wolff JA. Direct gene transfer into muscle. Vaccine. Dec. 1994;12(16):1499-502.

Darquet AM, Cameron B, Wils P, Scherman D, Crouzet J. A new DNA vehicle for nonviral gene delivery: supercoiled minicircle. Gene Ther. Dec. 1997;4(12):1341-9.

Darquet AM, Rangara R, Kreiss P, Schwartz B, Naimi S, Delaere P, Crouzet J, Scherman Minicircle: an improved DNA molecule for in vitro and in vivo gene transfer. Gene Ther. Feb. 1999;6(2):209-18.

Dasgupta S, Masukata H, Tomizawa J. Multiple mechanisms for initiation of ColE1 DNA replication: DNA synthesis in the presence and absence of ribonuclease H. EMBO J. Nov. 1986;5(11):2987-94.

Davis HL, Whalen RG, Demeneix BA. Direct gene transfer into skeletal muscle in vivo: factors affecting efficiency of transfer and stability of expression. Hum Gene Ther. Apr. 1993;4(2):151-9.

Deuschle U, Kammerer W, Gentz R, Bujard H. Promoters of *Escherichia coli*: a hierarchy of in vivo strength indicates alternate structures. EMBO J. Nov. 1986;5(11):2987-94.

Dolnik V, Novotny M, Chmelik J. Electromigration behavior of poly-(L-glutamate) conformers in concentrated polyacrylamide gels. Biopolymers. Aug. 1993;33(8):1299-306.

Dorsch-Hasler K, Keil GM, Weber F, Jasin M. Schaffner W, Koszinowski UH. A long and complex enhancer activates transcription of the gene coding for the highly abundant immediate early mRNA in murine cytomegalovirus. Proc Natl Acad Sci U S A. Dec. 1985;82(24):8325-9.

Draghia-Akli R, Ellis KM, Hill LA, Malone PB, Fiorotto ML. High-efficiency growth hormone-releasing hormone plasmid vector administration into skeletal muscle mediated by electroporation in pigs. FASEB J. Mar. 2003;17(3):526-8. Epub Jan. 2, 2003.

Draghia-Akli R, Fiorotto ML, Hill LA, Malone PB, Deaver DR, Schwartz RJ. Myogenic expression of an injectable protease-resistant growth hormone-releasing hormone augments long-term growth in pigs. Nat Biotechnol Dec. 1999;17(12):1179-83.

Draghia-Akli R, Khan AS, Cummings KK, Parghi D, Carpenter RH, Brown PA. Electrical enhancement of formulated plasmid delivery in animals. Technol Cancer Res Treat. Oct. 2002;1(5):365-72.

Draghia-Akli R, Li X, Schwartz RJ. Enhanced growth by ectopic expression of growth hormone releasing hormone using an injectable myogenic vector. Nat Biotechnol. Nov. 1997;15(12):1285-9.

Draghia-Akli R, Malone PB, Hill LA, Ellis KM, Schwartz RJ, Nordstrom JL. Enhanced animal growth via ligand-regulated GHRH myogenic-injectable vectors. FASEB J. Mar. 2002,16(3):426-8. Epub Jan. 14, 2002.

Fewell JG, Maclaughlin F, Mehta V, Gondo M, Nicol F, Wilson E, Smith LC. Gene therapy for the treatment of hemophilia B using PINC-formulated plasmid delivered to muscle with electroporation. Mol Ther. Apr. 2001;3(4):574-83.

Frederickson RM, Carter BJ, Pilaro AM. Nonclinical toxicology in support of licensure of gene therapies. Arlington, VA, USA, Mar. 13-14, 2003. Mol Ther. Jul. 2003;8(1):8-10.

Fryer AD, Jacoby DB. Effect of inflammatory cell mediators on M2 muscarinic receptors in the lungs. Life Sci. 1993;52(5-6):529-36.

Gayle RB 3rd, Vermersch PS, Bennett GN. Construction and characterization of pBR322-derived plasmids with deletions of the RNA I region. Gene. 1986;41(2-3):281-8.

Gehl J, Skovsgaard T, Mir LM. Enhancement of cytotoxicity by electropermeabilization: an improved method for screening drugs. Anticancer Drugs. Apr. 1998;9(4):319-25.

Gehl J, Sorensen TH, Nielsen K, Raskmark P, Nielsen SL, Skovsgaard T, Mir LM. In vivo electroporation of skeletal muscle: threshold, efficacy and relation to electric field distribution. Biochim Biophys Acta. Aug. 5, 1999;1428(2-3):233-40.

German M, Ashcroft S, Docherty K, Edlund H, Edlund T, Goodison S, Imura H, Kennedy G, Madsen O, Melloul D, et al. The insulin gene promoter. A simplified nomenclature. Diabetes. Aug. 1995;44(8):1002-4.

Harley CB, Reynolds RP. Analysis of *E. coli* promoter sequences. Nucleic Acids Res. Mar. 11, 1987;15(5):2343-61.

Heller R, Jaroszeski MJ, Glass LF, Messina JL, Rapaport DP, DeConti RC, Fenske NA, Gilbert RA, Mir LM, Reintgen DS. Phase I/II trial for the treatment of cutaneous and subcutaneous tumors using electrochemotherapy. Cancer. Mar. 1, 1996;77(5):964-71.

Horlick RA, Benfield PA. The upstream muscle-specific enhancer of the rat muscle creatine kinase gene is composed of multiple elements. Mol Cell Biol. Jun. 1989;9(6):2396-413.

Inouye C, Remondelli P, Karin M, Elledge S. Isolation of a cDNA encoding a metal response element binding protein using a novel expression cloning procedure: the one hybrid system. DNA Cell Biol. Jul. 1994;13(7):731-42.

Inouye S, Nakazawa A, Nakazawa T. Determination of the transcription initiation site and identification of the protein product of the regulatory gene xylR for xyl operons on the TOL plasmid. J Bacteriol. Sep. 1985;163(3):863-9.

Jaynes JB, Johnson JE, Buskin JN, Gartside CL, Hauschka SD. The muscle creatine kinase gene is regulated by multiple upstream elements, including a muscle-specific enhancer. Mol Cell Biol. Jan. 1988;8(1):62-70.

Jenkins GJ, Suzen HS, Sueiro RA, Parry JM. The restriction site mutation assay: a review of the methodology development and the current status of the technique. Mutagenesis. Sep. 1999;14(5):439-48.

Kammerer W, Deuschle U, Gentz R, Bujard H. Functional dissection of *Escherichia coli* promoters: information in the transcribed region is involved in late steps of the overall process. EMBO J. Nov. 1986;5(11):2995-3000.

Kawamoto T, Makino K, Niwa H, Sugiyama H, Kimura S, Amemura M, Nakata A, Kakunaga T. Identification of the human beta-actin enhancer and its binding factor. Mol Cell Biol. Jan. 1988;8(1):267-72.

Kawamoto T, Makino K, Orita S, Nakata A, Kakunaga T. DNA bending and binding factors of the human beta-actin promoter. Nucleic Acids Res. Jan. 25, 1989;17(2):523-37.

Klamut HJ, Bosnoyan-Collins LO, Worton RG, Ray PN, Davis HL. Identification of a transcriptional enhancer within muscle intron 1 of the human dystrophin gene. Hum Mol Genet. Oct. 1996;5(10):1599-606.

Klamut HJ, Gangopadhyay SB, Worton RG, Ray PN. Molecular and functional analysis of the muscle-specific promoter region of the Duchenne muscular dystrophy gene. Mol Cell Biol. Jan. 1990;10(1):193-205.

Kraus J, Woltje M, Schonwetter N, Hollt V. Alternative promoter usage and tissue specific expression of the mouse somatostatin receptor 2 gene. FEBS Lett. May 29, 1998;428(3):165-70.

Lahijani R, Hulley G, Soriano G, Horn NA, Marquet M. High-yield production of pBR322-derived plasmids intended for human gene therapy by employing a temperature-controllable point mutation. Hum Gene Ther. Oct. 20, 1996;7(16):1971-80.

Lareyre JJ, Thomas TZ, Zheng WL, Kasper S, Ong DE, Orgebln-Crist MC, Matusik RJ. A 5-kilobase pair promoter fragment of the murine epididymal retinoic acid-binding protein gene drives the tissue-specific, cell-specific, and androgen-regulated expression of a foreign gene in the epididymis of transgenic mice. J Biol Chem. Mar. 19, 1999;274(12):8282-90.

Larsen PR, Harney JW, Moore DD. Sequences required for cell-type specific thyroid hormone regulation of rat growth hormone promoter activity. J Biol Chem. Nov. 5, 1986;261(31):14373-6.

Ledwith BJ, Manam S, Troilo PJ, Barnum AB, Pauley CJ, Griffiths TG 2nd, Harper LB, Beare CM, Bagdon WJ, Nichols WW. Plasmid DNA vaccines: investigation of integration into host cellular DNA following intramuscular injection in mice. Intervirology. 2000;43(4-6):258-72.

Ledwith BJ, Manam S, Troilo PJ, Barnum AB, Pauley CJ, Griffiths TG 2nd, Harper LB, Schock HB, Zhang H, Faris JE, Way PA, Beare CM, Bagdon WJ, Nichols WW. Plasmid DNA vaccines: assay for integration into host genomic DNA. Dev Biol (Basel). 2000;104:33-43.

Lee SH, Wang W, Yajima S, Jose PA, Mouradian MM. Tissue-specific promoter usage in the D1A dopamine receptor gene in brain and kidney. DNA Cell Biol. Nov. 1997;16(11):1267-75.

Lesbordes JC, Bordet T, Haase G, Castelnau-Ptakhine L, Rouhani S, Gilgenkrantz H, Kahn A. In vivo electrotransfer of the cardiotrophin-1 gene into skeletal muscle slows down progression of motor neuron degeneration in pmn mice. Hum Mol Genet. Jul. 1, 2002;11(14):1615-25.

Levenson VV, Transue ED, Roninson IB. Internal ribosomal entry site-containing retroviral vectors with green fluorescent protein and drug resistance markers. Hum Gene Ther. May 20, 1998;9(8):1233-6.

Li C, Ke S, Wu QP, Tansey W, Hunter N, Buchmiller LM, Miles L, Charnsangavej C, Wallace S. Tumor irradiation enhances the tumor-specific distribution of poly(L-glutamic acid)-conjugated paclitaxel and its antitumor efficacy. Clin Cancer Res. Jul. 2000;6(7):2829-34.

Li X, Eastman EM, Schwartz RJ, Draghia-Akli R. Synthetic muscle promoters: activities exceeding naturally occurring regulatory sequences. Nat Biotechnol. Mar. 1999;17(3):241-5.

Lin H, Yutzey KE, Konieczny SF. Muscle-specific expression of the troponin I gene requires interactions between helix-loop-helix muscle regulatory factors and ubiquitous transcription factors. Mol Cell Biol. Jan. 1991; 11(1):267-80.

Lin-Chao S, Chen WT, Wong TT. High copy number of the pUC plasmid results from a Rom/Rop-suppressible point mutation in RNA II. Mol Microbiol. Nov. 1992;6(22):3385-93.

Liu Y. Li H, Tanaka K, Tsumaki N, Yamada Y. Identification of an enhancer sequence within the first intron required for cartilage-specific transcription of the alpha2(XI) collagen gene. J Biol Chem. Apr. 28, 2000;275(17):12712-8.

Lucas ML, Heller L, Coppola D, Heller R. IL-12 plasmid delivery by in vivo electroporation for the successful treatment of established subcutaneous B16.F10 melanoma. Mol Ther. Jun. 2002;5(6):668-75.

Lucas ML, Jaroszeski MJ, Gilbert R, Heller R. In vivo electroporation using an exponentially enhanced pulse: a new waveform. DNA Cell Biol. Mar. 2001;20(3):183-8.

Lyons AJ, Robertson HD. Detection of tRNA-like structure through RNase P cleavage of viral internal ribosome entry site RNAs near the AUG start triplet. J Biol Chem. Jul. 18, 2003;278(29):26844-50. Epub May 12, 2003.

Macejak DG, Sarnow P. Internal initiation of translation mediated by the 5' leader of a cellular mRNA. Nature. Sep. 5, 1991;353(6339):90-4.

Manam S, Ledwith BJ, Barnum AB, Troilo PJ, Pauley CJ, Harper LB, Griffiths TG 2nd, Niu Z, Denisova L, Follmer TT, Pacchlone SJ, Wang Z, Beare CM, Bagdon WJ, Nichols WW. Plasmid DNA vaccines: tissue distribution and effects of DNA sequence, adjuvants and delivery method on integration Into host DNA. Intervirology. 2000;43(4-6):273-81.

Manders P, Thomas R. Immunology of DNA vaccines: CpG motifs and antigen presentation. Inflamm Res. May 2000;49(5):199-205.

Martineau Y, Le Bec C, Monbrun L, Allo V, Chiu IM, Danos O, Moine H, Prats H, Prats AC. Internal ribosome entry site structural motifs conserved among mammalian fibroblast growth factor 1 alternatively spliced mRNAs. Mol Cell Biol. Sep. 2004;24(17):7622-35.

Matsubara H, Gunji Y, Maeda T, Tasaki K, Koide Y, Asano T, Ochiai T, Sakiyama S, Tagawa M. Electroporation-mediated transfer of cytokine genes into human esophageal tumors produces anti-tumor effects in mice. Anticancer Res. Jul.-Aug. 2001;21(4A):2501-3.

Matsuo A, Tooyama I, Isobe S. Oomura Y, Akiguchi I, Hanai K, Kimura J, Kimura H. Immunohistochemical localization in the rat brain of an epitope corresponding to the fibroblast growth factor receptor-1. Neuroscience. May 1994;60(1):49-66.

McCluskie MJ, Weeratna RD, Davis HL. The role of CpG in DNA vaccines. Springer Semin Immunopathol. 2000;22(1-2):125-32.

McNally MA, Lebkowski JS, Okarma TB, Lerch LB. Optimizing electroporation parameters for a variety of human hematopoietic cell lines. Biotechniques. Oct. 1988;6(9):882-6.

Miklavcic D, Berays K, Semrov D, Cemazar M, Demsar F, Sersa G. The importance of electric field distribution for effective in vivo electroporation of tissues. Biophys J. May 1998;74(5):2152-8.

Mumper RJ, Wang J, Klakamp SL, Nitta H, Anwer K, Tagliaferri F, Rolland AP. Protective interactive noncondensing (PINC) polymers for enhanced plasmid distribution and expression in rat skeletal muscle. J Control Release. Mar. 2, 1998;52(1-2):191-203.

Muramatsu T, Arakawa S, Fukazawa K, Fujiwara Y, Yoshida T, Sasaki R, Masuda S, Park HM. In vivo gene electroporation in skeletal muscle with special reference to the duration of gene expression. Int J Mol Med. Jan. 2001;7(1):37-42.

Nairn RS, Adair GM, Porter T, Pennington SL, Smith DG, Wilson JH, Seidman MM. Targeting vector configuration and method of gene transfer influence targeted correction of the APRT gene in Chinese hamster ovary cells. Somat Cell Mol Genet. Jul. 1993;19(4):363-75.

Narum DL, Kumar S, Rogers WO, Fuhrmann SR, Liang H, Oakley M, Taye A, Sim BK, Hoffman SL. Codon optimization of gene fragments encoding Plasmodium falciparum merzoite proteins enhances DNA vaccine protein expression and immunogenicity in mice. Infect Immun. Dec. 2001;69(12):7250-3.

Neumann E, Schaefer-Ridder M, Wang Y, Hofschneider PH. Gene transfer into mouse lyoma cells by electroporation in high electric fields. EMBO J. 1982;1(7):841-5.

Nomoto S, Tatematsu Y, Takahashi T, Osada H. Cloning and characterization of the alternative promoter regions of the human LIMK2 gene responsible for alternative transcripts with tissue-specific expression. Gene. Aug. 20, 1999 ;236(2):259-71.

Ohlsson H, Thor S, Edlund T. Novel insulin promoter- and enhancer-binding proteins that discriminate between pancreatic alpha- and beta-cells. Mol Endocrinol. Jul. 1991;5(7):897-904.

Otani Y, Tabata Y, Ikada Y. Rapidly curable biological glue composed of gelatin and poly(L-glutamic acid). Biomaterials. Jul. 1996;17(14):1387-91.

Otani Y, Tabata Y, Ikada Y. Hemostatic capability of rapidly curable glues from gelatin, poly(L-glutamic acid), and carbodiimide. Biomaterials. Nov. 1998;19(22):2091-8.

Pech M, Rao CD, Robbins KC, Aaronson SA. Functional identification of regulatory elements within the promoter region of platelet-derived growth factor 2. Mol Cell Biol. Feb. 1989;9(2):396-405.

Pelletier J, Sonenberg N. Internal initiation of translation of eukaryotic mRNA directed by a sequence derived from poliovirus RNA. Nature. Jul. 28, 1988;334(6180):320-5.

Pinkert CA, Ornitz DM, Brinster RL, Palmiter RD. An albumin enhancer located 10 kb upstream functions along with its promoter to direct efficient, liver-specific expression in transgenic mice. Genes Dev. May 1987;1(3):268-76.

Potter H, Weir L, Leder P. Enhancer-dependent expression of human kappa immunoglobulin genes introduced into mouse pre-B lymphocytes by electroporation. Proc Natl Acad Sci U S A. Nov. 1984;81(22):7161-5.

Ross W, Aiyar SE, Salomon J, Gourse RL. *Escherichia coli* promoters with UP elements of different strengths: modular structure of bacterial promoters. J Bacteriol. Oct. 1998;180(20):5375-83.

Ryu DD, Nam DH. Recent progress in biomolecular engineering. Biotechnol Prog. Jan.-Feb. 2000;16(1):2-16.

Scheule RK. The role of CpG motifs in immunostimulation and gene therapy. Adv Drug Deliv Rev. Nov. 15, 2000;44(2-3):119-34.

Shi H, Yan PS, Chen CM, Rahmatpanah F, Lofton-Day C, Caldwell CW, Huang TH. Expressed CpG island sequence tag microarray for dual screening of DNA hypermethylation and gene silencing in cancer cells. Cancer Res. Jun. 1, 2002;62(11):3214-20.

Shiraishi M, Sekiguchi A, Terry MJ, Oates AJ, Miyamoto Y, Chuu YH, Munakata M, Sekiya T. A comprehensive catalog of CpG islands methylated in human lung adenocarcinomas for the identification of tumor suppressor genes. Oncogene. May 23, 2002;21(23):3804-13.

Skroch P, Buchman C, Karin M. Regulation of human and yeast metallothionein gene transcription by heavy metal ions. Prog Clin Biol Res. 1993;380:113-28.

Smith LC, Nordstrom JL. Advances in plasmid gene delivery and expression in skeletal muscle. Curr Opin Mol Ther. Apr. 2000;2(2):150-4.

Soubrier F, Cameron B, Manse B, Somarriba S, Dubertret C, Jaslin G, Jung G, Caer CL, Dang D, Mouvault JM, Scherman D, Mayaux JF, Crouzet J. pCOR: a new design of plasmid vectors for nonviral gene therapy. Gene Ther. Aug. 1999;6(8):1482-8.

Stanford WL, Cohn JB, Cordes SP. Gene-trap mutagenesis: past, present and beyond. Nat Rev Genet. Oct. 2001;2(10):756-68.

Terada Y, Tanaka H, Okado T, Inoshita S, Kuwahara M, Akiba T, Sasaki S, Marumo F. Efficient and ligand-dependent regulated erythropoietin production by naked dna injection and in vivo electroporation. Am J Kidney Dis. Oct. 2001;38(4 Suppl 1):S50-3.

Tollefsen S, Vordermeier M, Olsen I, Storset AK, Reitan LJ, Clifford D, Lowrie DB, Wiker HG, Huygen K, Hewinson G, Mathiesen I, Tjelle TE. DNA injection in combination with electroporation: a novel method for vaccination of farmed ruminants. Scand J Immunol. Mar. 2003;57(3):229-38.

Tone CM, Cardoza DM, Carpenter RH, Draghia-Akli R. Long-term effects of plasmid-mediated growth hormone releasing hormone in dogs. Cancer Gene Ther. May 2004;11(5):389-96.

Toneguzzo F, Keating A, Glynn S, McDonald K. Electric field-mediated gene transfer: characterization of DNA transfer and patterns of integration in lymphoid cells. Nucleic Acids Res. Jun. 24, 1988;16(12):5515-32.

Tripathy SK, Svensson EC, Black HB, Goldwasser E, Margalith M, Hobart PM, Leiden JM. Long-term expression of erythropoietin in the systemic circulation of mice after intramuscular injection of a plasmid DNA vector. Proc Natl Acad Sci U S A. Oct. 1, 1996;93(20):10876-80.

Tronche F, Rollier A, Bach I, Weiss MC, Yaniv M. The rat albumin promoter: cooperation with upstream elements is required when binding of APF/HNF1 to the proximal element is partially impaired by mutation or bacterial methylation. Mol Cell Biol. Nov. 1989;9(11):4759-66.

Tronche F, Rollier A, Herbomel P, Bach I, Cereghini S, Weiss M, Yaniv M. Anatomy of the rat albumin promoter. Mol Biol Med. Apr. 1990;7(2):173-85.

Trudel M, Costantini F. A 3' enhancer contributes to the stage-specific expression of the human beta-globin gene. Genes Dev. Nov. 1987;1(9):954-61. Abstract only.

Tsumaki N, Kimura T, Tanaka K, Kimura JH, Ochi T, Yamada Y. Modular arrangement of cartilage- and neural tissue-specific cis-elements in the mouse alpha2(XI) collagen promoter. J Biol Chem. Sep. 4, 1998;273(36):22861-4.

Tsurumi Y, Takeshita S, Chen D, Kearney M, Rossow ST, Passeri J, Horowitz JR, Symes JF, Isner JM. Direct intramuscular gene transfer of naked DNA encoding vascular endothelial growth factor augments collateral development and tissue perfusion. Circulation. Dec. 15, 1996;94(12):3281-90.

Tur-Kaspa R, Teicher L, Levine BJ, Skoultchi AI, Shafritz DA. Use of electroporation to introduce biologically active foreign genes into primary rat hepatocytes. Mol Cell Biol. Feb. 1986;6(2):716-8.

Vilquin JT, Kennel PF, Paturneau-Jouas M, Chapdelaine P, Boissel N, Delaere P, Tremblay JP, Scherman D, Fiszman MY, Schwartz K. Electrotransfer of naked DNA in the skeletal muscles of animal models of muscular dystrophies. Gene Ther. Jul. 2001;8(14):1097-107.

Wolff JA, Malone RW, Williams P, Chong W, Acsadi G, Jani A, Feigner PL. Direct gene transfer into mouse muscle in vivo. Science. Mar. 23, 1990;247(4949 Pt 1):1465-8.

Wu HK, Squire JA, Song Q, Weksberg R. Promoter-dependent tissue-specific expressive nature of imprinting gene, insulin-like growth factor II, in human tissues. Biochem Biophys Res Commun. Apr. 7, 1997;233(1):221-6.

Xie TD, Tsong TY. Study of mechanisms of electric field-induced DNA transfection. V. Effects of DNA topology on surface binding, cell uptake, expression, and integration into host chromosomes of DNA in the mammalian cell. Biophys J. Oct. 1993;65(4):1684-9.

Yasui A, Oda K, Usunomiya H, Kakudo K, Suzuki T, Yoshida T, Park HM, Fukazawa K, Muramatsu T. Elevated gastrin secretion by in vivo gene electroporation in skeletal muscle. Int J Mol Med. Nov. 2001;8(5):489-94.

Yin D, Tang JG. Gene therapy for streptozotocin-induced diabetic mice by electroporational transfer of naked human insulin precursor DNA into skeletal muscle in vivo. FEBS Lett. Apr. 20, 2001;495(1-2):16-20.

Yorifuji T, Mikawa H. Co-transfer of restriction endonucleases and plasmid DNA into mammalian cells by electroporation: effects on stable transformation. Mutat Res. Feb. 1990;243(2):121-6.

Yutzey KE, Konieczny SF. Different E-box regulatory sequences are functionally distinct when placed within the context of the troponin I enhancer. Nucleic Acids Res. Oct. 11, 1992;20(19):5105-13.

Zhao-Emonet JC, Boyer O, Cohen JL, Klatzmann D. Deletional and mutational analyses of the human CD4 gene promoter: characterization of a minimal tissue-specific promoter. Biochim Biophys Acta. Nov. 8, 1998;1442(2-3):109-19.

Zheng Q, Kyle DJ. Computational screening of combinatorial libraries. Bioorg Med Chem. May 1996;4(5):631-8.

Zuker M. Mfold web server for nucleic acid folding and hybridization prediction. Nucleic Acids Res. Jul. 1, 2003;31(13):3406-15.

Draghia-Akli R, Hahn KA, King GK, Cummings KK, Carpenter RH. Effects of plasmid-mediated growth hormone-releasing hormone in severely debilitated dogs with cancer. Mol Ther. Dec. 2002;6(6):830-6.

Nagata, T., et al., Codon optimization effect on translational efficiency of DNA vaccine in mammalian cells: analysis of plasmid DNA encoding a CTL epitope derived from microorganisms, Biochem Biophys Res Commun., Aug. 2, 1999;261(2):445-51.

Uchijima, M., et al., Optimization of codon usage of plasmid DNA vaccine is required for the effective MHC class I-restricted T cell responses against an intracellular bacterium, J Immunol., Nov. 15, 1998;161(10):5594-9.

Meetei, A. R., et al., Hyperexpression of rat spermatidal protein TP2 in *Escherichia coli* by codon optimization and engineering the vector-encoded 5' UTR, Protein Expr Purif., Jul. 1998;13(2):184-90.

Andre, S., et al., Increased immune response elicited by DNA vaccination with a synthetic gp120 sequence with optimized codon usage, J Virol., Feb. 1998;72(2):1497-503.

Hale, R. S., et al., Codon optimization of the gene encoding a domain from human type 1 neurofibromin protein results in a threefold improvement in expression level in *Escherichia coli*, Protein Expr Purif., Mar. 1998;12(2):185-8.

Hubatsch, I., et al., Human glutathione transferase A4-4: an alpha class enzyme with high catalytic efficiency in the conjugation of 4-hydroxynonenal and other genotoxic products of lipid peroxidation, Biochem J., Feb. 15, 1998;330 ( Pt 1):175-9.

Misra, R. et al., Intermediates in the synthesis of ToIC protein include an incomplete peptide stalled at a rare Arg codon, Eur J Biochem. Oct. 1, 1985;152(1):151-5.

Deng, T., Bacterial expression and purification of biologically active mouse c-Fos proteins by selective codon optimization, FEBS Lett., Jun. 9, 1997;409(2):269-72.

Cormack, B. P., et al., Yeast-enhanced green fluorescent protein (yEGFP)a reporter of gene expression in Candida albicans, Microbiology., Feb. 1997;143 ( Pt 2):303-11.

Prapunwattana, P., et al., Chemical synthesis of the Plasmodium falciparum dihydrofolate reductase-thymidylate synthase gene, Mol Biochem Parasitol., Dec. 2, 1996;83(1):93-106.

Pikaart, M. J., et al., Expression and codon usage optimization of the erythroid-specific transcription factor cGATA-1 in baculoviral and bacterial systems, Protein Expr Purif., Dec. 1996;8(4):469-75.

Yang, T. T., et al., Optimized codon usage and chromophore mutations provide enhanced sensitivity with the green fluorescent protein, Nucleic Acids Res., Nov. 15, 1996;24(22):4592-3.

Gouka, R. J., et al., Analysis of heterologous protein production in defined recombinant Aspergillus awamori strains, Appl Environ Microbiol., Jun. 1996;62(6):1951-7.

Altmann, S. W., et al., Expression and purification of a synthetic human obese gene product, Protein Expr Purif., Dec. 1995;6(6):722-6.

Kane, J. F., Effects of rare codon clusters on high-level expression of heterologous proteins in *Escherichia coli*, Curr Opin Biotechnol., Oct. 1995;6(5):494-500.

Airenne, K. J., et al., Production of recombinant avidin in *Escherichia coli*, Gene, Jun. 24, 1994;144(1):75-80.

Wang, B. Q., et al., Importance of codon preference for production of human RAP74 and reconstitution of the RAP30/74 complex, Protein Expr Purif., Oct. 1994;5(5):476-85.

Gerchman, S. E., et al., Expression of chicken linker histones in *E. coli*: sources of problems and methods for overcoming some of the difficulties, Protein Expr Purif., Jun. 1994;5(3):242-51.

Robinson, M., et al., Codon usage can affect efficiency of translation of genes in *Escherichia coli*, Nucleic Acids Res. Sep. 11, 1984;12(17):6663-71.

Holler, T. P., et al., HIV1 integrase expressed in *Escherichia coli* from a synthetic gene, Gene, Dec. 22, 1993;136 (1-2):323-8.

Kane, J. F., et al., Novel in-frame two codon translational hop during synthesis of bovine placental lactogen in a recombinant strain of *Escherichia coli*, Nucleic Acids Res., Dec. 25, 1992;20(24):6707-12.

Pedersen, S., *Escherichia coli* ribosomes translate in vivo with variable rate, EMBO J., Dec. 1, 1984;3(12):2895-8.

Makoff, A. J., et al., Expression of tetanus toxin fragment C in *E. coli*: high level expression by removing rare codons, Nucleic Acids Res., Dec. 25, 1989;17(24):10191-202.

Kotula, L., et al., Evaluation of foreign gene codon optimization in yeast: expression of a mouse IG kappa chain, Biotechnology (N Y). Dec. 1991;9(12):1386-9.

Kim, C. H., et al., Codon optimization for high-level expression of human erythropoietin (EPO) in mammalian cells, Gene., Oct. 15, 1997;199(1-2):293-301.

Dittrich, W., et al., Production and secretion of recombinant proteins in Dictyostelium discoideum, Biotechnology (N Y). Jun. 1994;12(6):614-8.

\* cited by examiner

OPTIMIZED HIGH YIELD SYNTHETIC PLASMIDS

RELATED APPLICATIONS

This application claims priority to U.S. Provisional Patent Application Ser. No. 60/647,170 titled "Optimized High Yield Synthetic Plasmids," filed on Jan. 26, 2005, having Draghia-Akli et al., listed as inventors, the entire content of which is hereby incorporated by reference.

STATEMENT OF RIGHTS TO INVENTIONS MADE UNDER FEDERALLY SPONSORED RESEARCH

No federal funds were used in the development of the present invention.

BACKGROUND

One aspect of the current invention is an optimized high yield nucleic acid delivery vehicle, or synthetic expression plasmid. The synthetic expression plasmid of this invention has reduced components, and has been optimized to increase yield. In addition to a mammalian gene of interest, a typical nucleic acid delivery vehicle or synthetic expression plasmid contains many structural elements necessary for the in vitro amplification of the plasmid in a bacterial host. By restricting the plasmid backbone to essential bacterial structural elements (e.g. bacterial antibiotic resistance gene and origin of replication) one can eliminate detrimental sequences, but not affect the final gene product. By introducing targeted substitutions in the bacterial origin of replication, one can increase plasmid yield and decrease fermentation time, thus increasing productivity. The current invention involves a "synthetic plasmid backbone" that provides a small backbone with an improved origin of replication ("mut 8"), which is useful for plasmid supplementation therapy in mammals.

A plasmid based mammalian expression system is minimally composed of a plasmid backbone, and a nucleic acid sequence encoding a therapeutic expression product under the transcriptional regulation of a promoter, and followed by a 3'UTR and/or polyadenylation signal. A plasmid backbone typically contains elements necessary for the specific growth of only the bacteria that are transformed with the proper plasmid: (1) a bacterial origin of replication, and (2) a selection marker, typically a bacterial antibiotic resistance gene. However, there are plasmids, called mini-circles, that lack both the antibiotic resistance gene and the origin of replication (Darquet et al., 1997; Darquet et al., 1999; Soubrier et al., 1999). Production and purification of mini-circles is complex and extremely costly, and thus impractical for therapeutic applications in large animals and humans.

The use of in vitro amplified expression plasmid DNA (i.e. non-viral expression systems or plasmids) avoids the risks associated with viral vectors (Frederickson et al., 2003). The non-viral expression systems products generally have low toxicity due to the use of "species-specific" components, or components that are not expressed in eukaryotic cells, which minimizes the risks of immunogenicity generally associated with viral vectors. One aspect of the current invention is a new, versatile, optimized high yield plasmid-based mammalian expression system that will reduce the risk of adverse effects associated with prokaryotic nucleic acid sequences in mammalian hosts, while facilitating its in vitro production. In addition, this new plasmid will constitute the base of a species-specific library of plasmids for expression of hormones or other proteins for agricultural, companion animal and human applications.

The nucleotide sequence of the bacterial gene products can adversely affect a mammalian host receiving plasmid DNA. For example, it is desirable to avoid CpG sequences, as these sequences have been shown to cause a recipient host to have an immune response targeted against the plasmids (Manders and Thomas, 2000; Scheule, 2000), as well as possible gene silencing (Shi et al., 2002; Shiraishi et al., 2002). Thus, when properly designing and generating DNA coding regions of any expressed genes one could avoid the "cg" sequence, without changing the amino acid sequence. This process, called "optimization" was used to generate the plasmids described in the present application. Another aspect of the current invention involves the removal of unnecessary backbone DNA sequences that were shown to have no functionality in the new plasmid context. As a result of removal of unnecessary DNA sequences, a new plasmid backbone ("pAV9001") with unique cloning sites was constructed, which will be useful for plasmid-mediated gene supplementation.

RNA II is the primer for replication of ColE1-derived plasmids and it is inhibited by RNA I (Dasgupta et al., 1987; Gayle, III et al., 1986). Increasing the RNA II to RNA I ratio should increase the frequency of DNA replication initiation events, which should yield higher plasmid copy number. The danger is the production of levels of RNA II that are so elevated that they would lead to "runaway" plasmid replication. Thus, strict control of the relative potency of these sequences is necessary. In another embodiment of this invention, new improved RNA II sites were created. Plasmids containing these new sequences have decreased fermentation time to optimum concentration and result in high plasmid yields.

Two conserved regions about 35 and 10 base pairs (bp) upstream from the transcription start (−35 and −10 regions, respectively) were identified by comparison of numerous promoters (Harley and Reynolds, 1987). Extensive compilations and comparison of promoters of genes of *E. coli* and it plasmids supported and extended the concept of a "consensus" promoter sequence: a −35 (TTGACA) and −10 (TATAAT) region separated by 17 bp with transcription initiation at a purine about 7 bp downstream from the 3'end of the −10 region (Ross et al., 1998). While the −35 and −10 regions show the greatest conservation across promoters and are also the sites of nearly all mutations which affect transcriptional strength, other bases flanking the −35 and −10 regions, in addition to the start point also occur at greater than random frequencies and sometimes affect promoter activity (Bujard et al., 1983; Deuschle et al., 1986; Kammerer et al., 1986). In addition, variations in spacing between the −35 and −10 regions play a role in promoter strength.

Point mutations in the RNA II promoter: A mutation described in (Bert et al., 2000), alters the −10 element in the RNA II promoter from TAATCT to TAATAT in a ColE1-derived plasmid named pXPM. The mutated sequence is a closer match to the consensus −10 element described above, and was therefore predicted to increase the rate of RNA II transcription. Nevertheless, the effect of mutations in the particular context of each plasmid is highly unpredictable. We modified a plasmid with a pUC origin of replication which requires special fermentation condition, and already contains a mutation of a C to a T (located at position +112 of RNA II in the region of stem/loop IV that hybridizes to 5' end of RNA I) that increases plasmid copy number (Lahijani et al., 1996; Lin-Chao et al., 1992). The effectiveness and results of combination of mutations is unpredictable, and can be assessed only by measuring plasmid yield, after the sequence has been synthetically generated.

There are several different approaches that can be utilized for the treatment of chronic conditions, such as cancer, arthritis, renal failure or immune dysfunction. Effective treatment may require the presence of therapeutic agents for extended periods of time. In the case of proteins, this is problematic. Gene therapeutic approaches may offer a solution to this problem. Experimental studies have confirmed the feasibility, efficacy and safety of plasmid-mediated gene supplementation for the treatment of chronic conditions.

Direct plasmid DNA gene transfer is currently the basis of many emerging nucleic acid therapy strategies and does not require viral components or lipid particles (Aihara and Miyazaki, 1998; Muramatsu et al., 2001). Skeletal muscle is target tissue, because muscle fiber has a long life span and can be transduced by circular DNA plasmids that are expressed in immunocompetent hosts (Davis et al., 1993; Tripathy et al., 1996). Plasmid DNA constructs are attractive candidates for direct therapy into the subjects skeletal muscle because the constructs are well-defined entities that are biochemically stable and have been used successfully for many years (Acsadi et al., 1991; Wolff et al., 1990). The relatively low expression levels of an encoded product that are achieved after direct plasmid DNA injection are sometimes sufficient to indicate bio-activity of secreted peptides (Danko and Wolff, 1994; Tsurumi et al., 1996). Previous reports demonstrated that human GHRH cDNA could be delivered to muscle by an injectable myogenic expression vector in mice where it transiently stimulated GH secretion to a modest extent over a period of two weeks (Draghia-Akli et al., 1997).

Efforts have been made to enhance the delivery of plasmid DNA to cells by physical means including electroporation, sonoporation, and pressure. Although not wanting to be bound by theory, the administration of a nucleic acid construct by electroporation involves the application of a pulsed electric field to create transient pores in the cellular membrane without causing permanent damage to the cell, which allows exogenous molecules to enter the cell (Smith and Nordstrom, 2000). By adjusting the electrical pulse generated by an electroporetic system, nucleic acid molecules can travel through passageways or pores in the cell that are created during the procedure. U.S. Pat. No. 5,704,908 titled "Electroporation and iontophoresis catheter with porous balloon," issued on Jan. 6, 1998 with Hofmann et al., listed as inventors describes an electroporation apparatus for delivering molecules to cells at a selected location within a cavity in the body of a patient. Similar pulse voltage injection devices are also described in: U.S. Pat. No. 5,702,359 titled "Needle electrodes for mediated delivery of drugs and genes," issued on Dec. 30, 1997, with Hofmann, et al., listed as inventors; U.S. Pat. No. 5,439,440 titled "Electroporation system with voltage control feedback for clinical applications," issued on Aug. 8, 1995 with Hofmann listed as inventor; PCT application WO/96/12520 titled "Electroporetic Gene and Drug Therapy by Induced Electric Fields," published on May 5, 1996 with Hofmann et al., listed as inventors; PCT application WO/96/12006 titled "Flow Through Electroporation Apparatus and Method," published on Apr. 25, 1996 with Hofmann et al., listed as inventors; PCT application WO/95/19805 titled "Electroporation and Iontophoresis Apparatus and Method For insertion of Drugs and genes into Cells," published on Jul. 27, 1995 with Hofmann listed as inventor; and PCT application WO/97/07826 titled "In Vivo Electroporation of Cells," published on Mar. 6, 1997, with Nicolau et al., listed as inventors, the entire content of each of the above listed references is hereby incorporated by reference.

Recently, significant progress to enhance plasmid delivery in vivo and subsequently to achieve physiological levels of a secreted protein was obtained using the electroporation technique. Electroporation has been used very successfully to transfect tumor cells after injection of plasmid (Lucas et al., 2002; Matsubara et al., 2001)) or to deliver the anti-tumor drug bleomycin to cutaneous and subcutaneous tumors in humans (Gehl et al., 1998; Heller et al., 1996). Electroporation also has been extensively used in mice (Lesbordes et al., 2002; Lucas et al., 2001; Vilquin et al., 2001), rats (Terada et al., 2001; Yasui et al., 2001) and dogs (Fewell et al., 2001) to deliver therapeutic genes that encode for a variety of hormones, cytokines or enzymes. Previous studies using GHRH showed that plasmid therapy with electroporation is scalable and represents a promising approach to induce production and regulated secretion of proteins in large animals and humans (Draghia-Akli et al., 1999; Draghia-Akli et al., 2002c). Electroporation also has been extensively used in rodents and other small animals (Bettan et al., 2000; Yin and Tang, 2001). Intramuscular injection of plasmid followed by electroporation has been used successfully in ruminants for vaccination purposes (Babiuk et al., 2003; Tollefsen et al., 2003). It has been observed that the electrode configuration affects the electric field distribution, and subsequent results (Gehl et al., 1999; Miklavcic et al., 1998). Although not wanting to be bound by theory, needle electrodes give consistently better results than external caliper electrodes in a large animal model.

The ability of electroporation to enhance plasmid uptake into the skeletal muscle has been well documented. Similarly, plasmids formulated with poly-L-glutamate ("PLG") or polyvinylpyrrolidone ("PVP") were observed to have an increase in plasmid transfection, which consequently increased the expression of a desired transgene. For example, plasmids formulated with PLG or PVP were observed to increase gene expression to up to 10 fold in the skeletal muscle of mice, rats, and dogs (Fewell et al., 2001; Mumper et al., 1998). Although not wanting to be bound by theory, the anionic polymer sodium PLG enhances plasmid uptake at low plasmid concentrations and reduces any possible tissue damage caused by the procedure. PLG is a stable compound and it is resistant to relatively high temperatures (Dolnik et al., 1993). PLG has been used to increase stability of anti-cancer drugs (Li et al., 2000) and as "glue" to close wounds or to prevent bleeding from tissues during wound and tissue repair (Otani et al., 1996; Otani et al., 1998). PLG has been used to increase stability in vaccine preparations (Matsuo et al., 1994) without increasing their immunogenicity. PLG also has been used as an anti-toxin after antigen inhalation or exposure to ozone (Fryer and Jacoby, 1993).

Although not wanting to be bound by theory, PLG increases the transfection of the plasmid during the electroporation process, not only by stabilizing the plasmid DNA and facilitating the intracellular transport through the membrane pores, but also through an active mechanism. For example, positively charged surface proteins on the cells could complex the negatively charged PLG linked to plasmid DNA through protein-protein interactions. When an electric field is applied, the surface proteins reverse direction and actively internalize the DNA molecules, a process that substantially increases the transfection efficiency. Furthermore, PLG will prevent the muscle damage associated with in vivo plasmid delivery (Draghia-Akli et al., 2002b) and will increase plasmid stability in vitro prior to injection. There are studies directed to electroporation of eukaryotic cells with linear DNA (McNally et al., 1988; Neumann et al., 1982) (Toneguzzo et al., 1988) (Aratani et al., 1992; Naim et al., 1993; Xie and Tsong, 1993; Yorifuji and Mikawa, 1990), but these examples illustrate transfection into cell suspensions, cell cultures, and the like, and such transfected cells are not present in a somatic tissue.

U.S. Pat. No. 4,956,288 is directed to methods for preparing recombinant host cells containing high copy number of a foreign DNA by electroporating a population of cells in the presence of the foreign DNA, culturing the cells, and killing the cells having a low copy number of the foreign DNA.

Although not wanting to be bound by theory, a GHRH cDNA can be delivered to muscle of mice and humans by an injectable myogenic expression vector where it can transiently stimulate GH secretion over a period of two weeks (Draghia-Akli et al., 1997). This injectable vector system was optimized by incorporating a powerful synthetic muscle promoter (Li et al., 1999) coupled with a novel protease-resistant GHRH molecule with a substantially longer half-life and greater GH secretory activity (pSP-HV-GHRH) (Draghia-Akli et al., 1999). Highly efficient electroporation technology was optimized to deliver the nucleic acid construct to the skeletal muscle of an animal (Draghia-Akli et al., 2002b). Using a skillful combination of vector design and electric pulses plasmid delivery method, the inventors were able to show increased growth and favorably modified body composition in pigs (Draghia-Akli et al., 1999; Draghia-Akli et al., 2003) and rodents (Draghia-Akli et al., 2002c), and improved immune surveillance in dairy cattle (Brown et al., 2004). The modified GHRH nucleic acid constructs increased red blood cell production in companion animals with cancer and cancer treatment-associated anemia (Draghia-Akli et al., 2002a).

Administering novel GHRH analog proteins (U.S. Pat. Nos. 5,847,066; 5,846,936; 5,792,747; 5,776,901; 5,696,089; 5,486,505; 5,137,872; 5,084,442, 5,036,045; 5,023,322; 4,839,344; 4,410,512, RE33,699) or synthetic or naturally occurring peptide fragments of GHRH (U.S. Pat. Nos. 4,833, 166; 4,228,158; 4,228,156; 4,226,857; 4,224,316; 4,223,021; 4,223,020; 4,223,019) for the purpose of increasing release of growth hormone have been reported. A GHRH analog containing the following mutations have been reported (U.S. Pat. No. 5,846,936): Tyr at position 1 to His; Ala at position 2 to Val, Leu, or others; Asn at position 8 to Gln, Ser, or Thr; Gly at position 15 to Ala or Leu; Met at position 27 to Nle or Leu; and Ser at position 28 to Asn. The GHRH analog is the subject of U.S. Pat. No. 6,551,996 titled "Super-active porcine growth hormone releasing hormone analog," issued on Apr. 22, 2003 with Schwartz, et al., listed as inventors ("the '996 patent"), which teaches application of a GHRH analog containing mutations that improve the ability to elicit the release of growth hormone. In addition, the '996 patent application relates to the treatment of growth deficiencies; the improvement of growth performance; the stimulation of production of growth hormone in an animal at a greater level than that associated with normal growth; and the enhancement of growth utilizing the administration of growth hormone releasing hormone analog and is herein incorporated by reference.

In summary, prior art has shown that it is possible to create new plasmids in a limited capacity utilizing existent plasmids or fragments from previously produced plasmids, but these techniques, and the resultant plasmids have some significant drawbacks: numerous CpG islands that can inhibit and reduce expression after treatment in vivo, large plasmid backbones that can accommodate relatively small transgenes, numerous bacterial elements with unknown function in eukaryotic cells, multiple cloning site regions with unknown effect on expression and replication, etc. It has also been taught that nucleic acid expression plasmids that encode recombinant proteins are viable solutions to the problems of frequent injections and high cost of traditional recombinant therapy. However, the nucleic acid expression plasmids also have some drawbacks when injected into a mammalian host. The synthetic plasmids of this invention have reduced components, and have been codon optimized to increase efficacy, and reduce adverse reactions in vivo. The introduction of point mutations in to the encoded recombinant proteins was a significant step forward in producing proteins that are more stable in vivo than the wild-type counterparts. Since there is a need in the art to expanded treatments for subjects with a disease by utilizing nucleic acid expression constructs that are delivered into a subject and express stable therapeutic proteins in vivo, the combination of codon optimization of an encoded therapeutic mammalian gene in an optimized plasmid backbone will further enhance the art of plasmid-mediated gene supplementation. Furthermore, the creation of new, improved optimized plasmids allow for better and more efficient production, with lower manufacturing costs and less time per round of production/purification.

SUMMARY

One aspect of the current invention is an optimized synthetic mammalian expression plasmid with modified origin of replication (e.g. "mut 8"). This new plasmid comprises a therapeutic element, and a replication element. The therapeutic element of the new plasmid comprises a eukaryotic promoter; a 5' untranslated region ("5'UTR"); a codon-optimized-eukaryotic therapeutic gene sequence; and a polyadenylation signal. The therapeutic elements of this plasmid are operatively linked and located in a first operatively-linked arrangement. Additionally, the optimized synthetic mammalian expression plasmid comprises replication elements, wherein the replication elements are operatively linked and located in a second operatively-linked arrangement. The replication elements comprise a selectable marker gene promoter, a ribosomal binding site, and an improved origin of replication. The first-operatively-linked arrangement and the second-operatively-linked arrangement comprise a circular structure of the codon optimized synthetic mammalian expression plasmid.

In preferred embodiments, the synthetic mammalian expression plasmid comprises a pUC-18 prokaryotic origin of replication sequence. However, the origin of replication may also comprise an autonomously replication sequence ("ARS"), or modifications that may improve plasmid yield and time of fermentation. Additionally, the codon-optimized plasmid backbone comprises at least one optimized CpG codon. In a preferred embodiment, the polyadenylation signal ("polyA") comprises a human growth hormone ("hGH") poly (A) signal, and a hGH 5' untranslated region ("5'UTR"). The codon-optimized mammalian therapeutic gene sequence comprises a sequence that encodes a species-specific or modified growth hormone releasing hormone ("GHRH"). In preferred embodiments, the codon-optimized sequence comprises human, porcine, mouse, rat, bovine, ovine, and chicken GHRH, or their analogs.

Another aspect of the current invention is a method for plasmid mediated gene supplementation that comprises delivering a codon-optimized synthetic mammalian expression plasmid into a subject. The codon-optimized synthetic mammalian expression plasmid encodes a growth hormone releasing hormone ("GHRH") or functional biological equivalent in the subject. The method of delivering the codon-optimized synthetic mammalian expression plasmid into the cells of the subject is via direct plasmid injection into the target tissue or organ followed by electroporation. In a preferred embodiment, the cells of the subject can be somatic cells, stem cells, or germ cells. The codon-optimized synthetic mammalian expression plasmids consisting of SEQ ID NO.: 2, SEQ ID NO.: 12, SEQ ID NO.: 13, SEQ ID NO.: 14, SEQ ID NO.: 15 have been contemplated by the inventors. The encoded GHRH is a biologically active polypeptide; and the encoded functional biological equivalent of GHRH is a polypeptide that has been engineered to contain a distinct amino acid sequence while simultaneously having similar or improved biologically activity when compared to the GHRH polypeptide. One result of expressing the encoded GHRH or functional biological equivalent thereof in a subject is the facilitation of growth hormone ("GH") secretion in the subject.

DETAILED DESCRIPTION OF PREFERRED EMBODIMENTS

Figure 1:
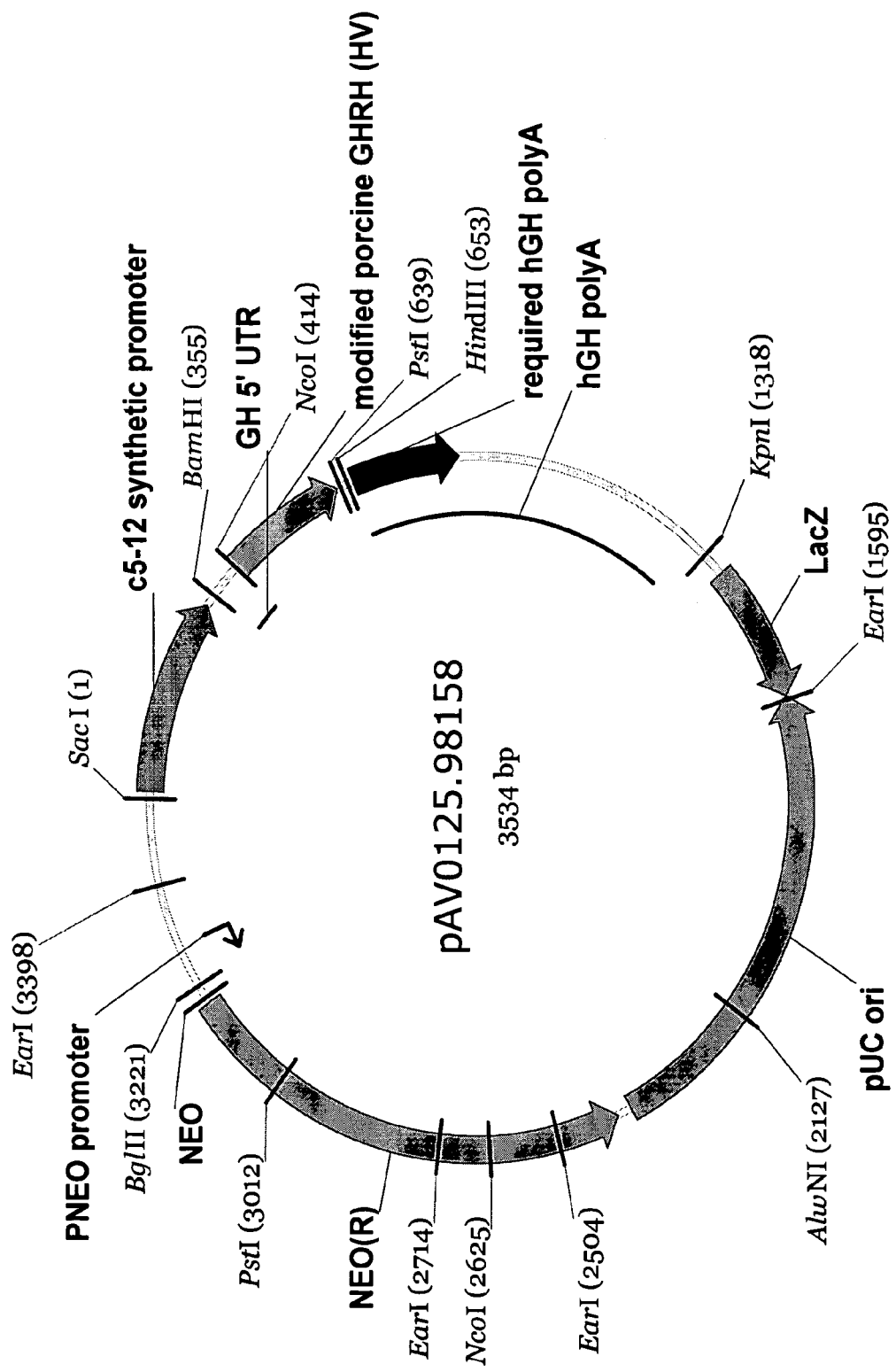
FIG. 1 shows a general map of a plasmid construct (pAV0125, this plasmid contains the porcine modified HV-GHRH sequence) used prior construction of an optimized synthetic plasmid of the current invention.

Terms: It will be readily apparent to one skilled in the art that various substitutions and modifications may be made in the invention disclosed herein without departing from the scope and spirit of the invention.

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "analog" as used herein includes any mutant of GHRH, or synthetic or naturally occurring peptide fragments of GHRH.

The term "cassette" as used herein is defined as one or more transgene expression sequences.

The term "cell-transfecting pulse" as used herein is defined as a transmission of a force which results in transfection of a vector, such as a linear DNA fragment, into a cell. In some embodiments, the force is from electricity, as in electroporation, or the force is from vascular pressure.

The term "coding region" as used herein refers to any portion of the DNA sequence that is transcribed into messenger RNA (mRNA) and then translated into a sequence of amino acids characteristic of a specific polypeptide.

The term "codon" as used herein refers to any group of three consecutive nucleotide bases in a given messenger RNA molecule, or coding strand of DNA that specifies a particular amino-acid, a starting or stopping signal for translation. The term codon also refers to base triplets in a DNA strand.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 15%, more typically less than 5%, and even more typically less than 1%) in an encoded sequence are "conservatively modified variations" where the alterations result in the substitution of an amino acid with a chemically similar amino acid. Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "complementary" means that one nucleic acid molecule has the sequence of the binding partner of another nucleic acid molecule. Thus, the sequence 5'-ATGC-3' is complementary to the sequence 5'-GCAT-3'.

The term "codon" as used herein refers to any group of three consecutive nucleotide bases in a given messenger RNA molecule, or coding strand of DNA that specifies a particular amino-acid, or a starting or stopping signal for translation. The term codon also refers to base triplets in a DNA strand.

The term "coding region" as used herein refers to any portion of the DNA sequence that is transcribed into messenger RNA (mRNA) and then translated into a sequence of amino acids characteristic of a specific polypeptide.

The term "delivery" as used herein is defined as a means of introducing a material into a subject, a cell or any recipient, by means of chemical or biological process, injection, mixing, electroporation, sonoporation, or combination thereof, either under or without pressure.

The term "electroporation" as used herein refers to a method that utilized electric pulses to deliver a nucleic acid sequence into cells.

The terms "electrical pulse" and "electroporation" as used herein refer to the administration of an electrical current to a tissue or cell for the purpose of taking up a nucleic acid molecule into a cell. A skilled artisan recognizes that these terms are associated with the terms "pulsed electric field" "pulsed current device" and "pulse voltage device." A skilled artisan recognizes that the amount and duration of the electrical pulse is dependent on the tissue, size, and overall health of the recipient subject, and furthermore knows how to determine such parameters empirically.

The term "encoded GHRH" as used herein is a biologically active polypeptide.

The term "functional biological equivalent" of GHRH as used herein is a polypeptide that has a distinct amino acid sequence from a wild type GHRH polypeptide while simultaneously having similar or improved biological activity when compared to the GHRH polypeptide. The functional biological equivalent may be naturally occurring or it may be modified by an individual. A skilled artisan recognizes that the similar or improved biological activity as used herein refers to facilitating and/or releasing growth hormone or other pituitary hormones. A skilled artisan recognizes that in some embodiments the encoded functional biological equivalent of GHRH is a polypeptide that has been engineered to contain a distinct amino acid sequence while simultaneously having similar or improved biological activity when compared to the GHRH polypeptide. Methods known in the art to engineer such a sequence include site-directed mutagenesis.

The term "growth hormone" ("GH") as used herein is defined as a hormone that relates to growth and acts as a chemical messenger to exert its action on a target cell. In a specific embodiment, the growth hormone is released by the action of growth hormone releasing hormone.

The term "growth hormone releasing hormone" ("GHRH") as used herein is defined as a hormone that facilitates or stimulates release of growth hormone and in a lesser extent other pituitary hormones, as prolactin.

The term "heterologous nucleic acid sequence" as used herein is defined as a DNA sequence consisting of differing regulatory and expression elements.

The term "identical" in the context of two nucleic acid or polypeptide sequences refers to the residues in the two sequences which are the same when aligned for maximum correspondence. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a fill mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers and Miller, Computer Applic. Biol. Sci., 4: 11-17 (1988); Smith and Waterman (1981) Adv. Appl. Math. 2: 482; Needleman and Wunsch (1970) J. Mol. Biol. 48: 443; Pearson and Lipman (1988) Proc. Natl. Acad. Sci. USA 85: 2444; Higgins and Sharp (1988) Gene, 73: 237-244 and Higgins and Sharp (1989) CABIOS 5: 151-153; Corpet, et al. (1988) Nucleic Acids Research 16, 10881-90; Huang, et al. (1992) Computer Applications in the Biosciences 8, 155-65, and Pearson, et al. (1994) Methods in Molecular Biology 24, 307-31. Alignment is also often performed by inspection and manual alignment.

The term "isolated" as used herein refers to synthetic or recombinant preparation of molecules in a purified, or concentrated, or both, form, substantially free from undesirable properties.

The term "non-optimized codon" as used herein refers to a codon that does not have a match codon frequency in target and host organisms. The non-optimized codons of this invention were determined using Aptagen's Gene Forge® codon optimization and custom gene synthesis platform (Aptagen, Inc., 2190 Fox Mill Rd. Suite 300, Herndon, Va. 20171). Other publicly available databases for optimized codons are available and will work equally as well, which is indicated in FIG. 11.

The term "nucleic acid expression construct" as used herein refers to any type of an isolated genetic construct comprising a nucleic acid coding for a RNA capable of being transcribed. The term "expression vector" can also be used interchangeably herein. In specific embodiments, the isolated nucleic acid expression construct comprises: a promoter; a nucleotide sequence of interest; and a 3' untranslated region; wherein the promoter, the nucleotide sequence of interest, and the 3' untranslated region are operatively linked; and in vivo expression of the nucleotide sequence of interest is regulated by the promoter. The term "DNA fragment" as used herein refers to a substantially double stranded DNA molecule. Although the fragment may be generated by any standard molecular biology means known in the art, in some embodiments the DNA fragment or expression construct is generated by restriction digestion of a parent DNA molecule.

The terms "expression vector," "expression cassette," or "expression plasmid" can also be used interchangeably. Although the parent molecule may be any standard molecular biology DNA reagent, in some embodiments the parent DNA molecule is a plasmid.

The term "operatively linked" as used herein refers to elements or structures in a nucleic acid sequence that are linked by operative ability and not physical location. The elements or structures are capable of, or characterized by accomplishing a desired operation. It is recognized by one of ordinary skill in the art that it is not necessary for elements or structures in a nucleic acid sequence to be in a tandem or adjacent order to be operatively linked.

The term "optimized codon" as used herein refers to a codon that has increased codon frequency in target and host organisms, but does not alter the amino acid sequence of the original translated protein. The optimized codons of this invention were determined using Aptagen's Gene Forge® codon optimization and custom gene synthesis platform (Aptagen, Inc., 2190 Fox Mill Rd. Suite 300, Herndon, Va. 20171). Other publicly available databases for optimized codons as appear below are available and will work equally as well:

KIM, C. H., ET AL., Codon optimization for high-level expression of human erythropoietin (EPO) in mammalian cells, Gene., 1997 Oct. 15; 199(1-2):293-301;

DITTRICH, W., ET AL., Production and secretion of recombinant proteins in Dictyostelium discoideum, Biotechnology (N Y). 1994 June; 12(6):614-8;

KOTULA, L., ET AL., Evaluation of foreign gene codon optimization in yeast: expression of a mouse IG kappa chain, Biotechnology (N Y). 1991 December; 9(12):1386-9;

NAGATA, T., ET AL., Codon optimization effect on translational efficiency of DNA vaccine in mammalian cells: analysis of plasmid DNA encoding a CTL epitope derived from microorganisms, Biochem Biophys Res Commun., 1999 Aug. 2; 261(2):445-51;

UCHIJIMA, M., ET AL., Optimization of codon usage of plasmid DNA vaccine is required for the effective MHC class I-restricted T cell responses against an intracellular bacterium, J Immunol., 1998 Nov. 15; 161(10):5594-9;

MEETEI, A. R., ET AL., Hyperexpression of rat spermatidal protein TP2 in *Escherichia coli* by codon optimization and engineering the vector-encoded 5' UTR, Protein Expr Purif., 1998 July; 13(2):184-90;

ANDRE, S., ET AL., Increased immune response elicited by DNA vaccination with a synthetic gp120 sequence with optimized codon usage, J Virol., 1998 February; 72(2):1497-503;

HALE, R. S., ET AL., Codon optimization of the gene encoding a domain from human type 1 neurofibromin protein results in a threefold improvement in expression level in *Escherichia coli*, Protein Expr Purif., 1998 March; 12(2):185-8;

HUBATSCH, I., ET AL., Human glutathione transferase A4-4: an alpha class enzyme with high catalytic efficiency in the conjugation of 4-hydroxynonenal and other genotoxic products of lipid peroxidation, Biochem J., 1998 Feb. 15; 330 (Pt 1):175-9;

MISRA, R. ET AL., Intermediates in the synthesis of TolC protein include an incomplete peptide stalled at a rare Arg codon, Eur J Biochem. 1985 Oct. 1; 152(1):151-5;

DENG, T., Bacterial expression and purification of biologically active mouse c-Fos proteins by selective codon optimization, FEBS Lett., 1997 Jun. 9; 409(2):269-72;

CORMACK, B. P., ET AL., Yeast-enhanced green fluorescent protein (yEGFP) a reporter of gene expression in *Candida albicans*, Microbiology., 1997 February; 143 (Pt 2):303-11;

PRAPUNWATTANA, P., ET AL., Chemical synthesis of the *Plasmodium falciparum* dihydrofolate reductase-thymidylate synthase gene, Mol Biochem Parasitol., 1996 Dec. 2; 83(1):93-106;

PIKAART, M. J., ET AL., Expression and codon usage optimization of the erythroid-specific transcription factor cGATA-1 in baculoviral and bacterial systems, Protein Expr Purif., 1996 December; 8(4):469-75;

YANG, T. T., ET AL., Optimized codon usage and chromophore mutations provide enhanced sensitivity with the green fluorescent protein, Nucleic Acids Res., 1996 Nov. 15; 24(22):4592-3;

GOUKA, R. J., ET AL., Analysis of heterologous protein production in defined recombinant *Aspergillus awamori* strains, Appl Environ Microbiol., 1996 June; 62(6):1951-7;

ALTMANN, S. W., ET AL., Expression and purification of a synthetic human obese gene product, Protein Expr Purif., 1995 December; 6(6):722-6;

KANE, J. F., Effects of rare codon clusters on high-level expression of heterologous proteins in *Escherichia coli*, Curr Opin Biotechnol., 1995 October; 6(5):494-500;

AIRENNE, K. J., ET AL., Production of recombinant avidin in *Escherichia coli*, Gene, 1994 Jun. 24; 144(1):75-80;

WANG, B. Q., ET AL., Importance of codon preference for production of human RAP74 and reconstitution of the RAP30/74 complex, Protein Expr Purif., 1994 October; 5(5): 476-85;

GERCHMAN, S. E., ET AL., Expression of chicken linker histones in *E. coli*: sources of problems and methods for overcoming some of the difficulties, Protein Expr Purif., 1994 June; 5(3):242-51;

ROBINSON, M., ET AL., Codon usage can affect efficiency of translation of genes in *Escherichia coli*, Nucleic Acids Res. 1984 Sep. 11; 12(17):6663-71;

HOLLER, T. P., ET AL., HIV1 integrase expressed in *Escherichia coli* from a synthetic gene, Gene, 1993 Dec. 22; 136(1-2):323-8;

KANE, J. F., ET AL., Novel in-frame two codon translational hop during synthesis of bovine placental lactogen in a recombinant strain of *Escherichia coli*, Nucleic Acids Res., 1992 Dec. 25; 20(24):6707-12;

PEDERSEN, S., *Escherichia coli* ribosomes translate in vivo with variable rate, EMBO J., 1984 Dec. 1; 3(12):2895-8;

MAKOFF, A. J., ET AL., Expression of tetanus toxin fragment C in *E. coli*: high level expression by removing rare codons, Nucleic Acids Res., 1989 Dec. 25; 17(24):10191-202.

The term "optimized nucleic acid delivery vehicle" as used herein refers to any vector that delivers a nucleic acid into a cell or organism wherein at least one of the codons has been optimized for expression in a host organism. The term "synthetic expression plasmid" can also be used interchangeably with the term optimized nucleic acid delivery vehicle.

The term "plasmid" as used herein refers generally to a construction comprised of extra-chromosomal genetic material, usually of a circular duplex of DNA that can replicate independently of chromosomal DNA. Plasmids, or fragments thereof, may be used as vectors. Plasmids are double-stranded DNA molecule that occur or are derived from bacteria and (rarely) other microorganisms. However, mitochondrial and chloroplast DNA, yeast killer and other cases are commonly excluded.

The term "plasmid backbone" as used herein refers to a sequence of DNA that typically contains a bacterial origin of replication, and a bacterial antibiotic selection gene, which are necessary for the specific growth of only the bacteria that are transformed with the proper plasmid. However, there are plasmids, called mini-circles, that lack both the antibiotic resistance gene and the origin of replication (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is that the plasmid backbone does not contain viral nucleotide sequences, and it is small.

The term "plasmid mediated gene supplementation" as used herein refers a method to allow a subject to have prolonged exposure to a therapeutic range of a therapeutic protein by utilizing a nucleic acid-expression construct in vivo.

The term "poly-L-glutamate ("PLG")" as used herein refers to a biodegradable polymer of L-glutamic acid that is suitable for use as a vector or adjuvant for DNA transfer into cells with or without electroporation.

The term "promoter" as used herein refers to a sequence of DNA that directs the transcription of a gene. A promoter may direct the transcription of a prokaryotic or eukaryotic gene. A promoter may be "inducible", initiating transcription in response to an inducing agent or, in contrast, a promoter may be "constitutive", whereby an inducing agent does not regulate the rate of transcription. A promoter may be regulated in a tissue-specific or tissue-preferred manner, such that it is only active in transcribing the operable linked coding region in a specific tissue type or types.

The term "pulse voltage device," or "pulse voltage injection device" as used herein relates to an apparatus that is capable of causing or causes uptake of nucleic acid molecules into the cells of an organism by emitting a localized pulse of electricity to the cells. The cell membrane then destabilizes, forming passageways or pores. Conventional devices of this type are calibrated to allow one to select or adjust the desired voltage amplitude and the duration of the pulsed voltage. The primary importance of a pulse voltage device is the capability of the device to facilitate delivery of compositions of the invention, particularly new plasmids with optimized expression cassettes and plasmid backbone, into the cells of the organism.

The term "replication element" as used herein comprises nucleic acid sequences that will lead to replication of a plasmid in a specified host. One skilled in the art of molecular biology will recognize that the replication element may include, but is not limited to a selectable marker gene promoter, a ribosomal binding site, a selectable marker gene sequence, and a origin of replication.

The term "secretagogue" as used herein refers to an agent that stimulates secretion. For example, a growth hormone secretagogue is any molecule that stimulates the release of growth hormone from the pituitary when delivered into an animal. Growth hormone releasing hormone is a growth hormone secretagogue.

The terms "subject" or "animal" as used herein refers to any species of the animal kingdom. In preferred embodiments, it refers more specifically to humans and domesticated animals used for: pets (e.g. cats, dogs, etc.); work (e.g. horses, etc.); food (cows, chicken, fish, lambs, pigs, etc); and all others known in the art.

The term "therapeutic element" as used herein comprises nucleic acid sequences that will lead to an in vivo expression of an encoded gene product. One skilled in the art of molecular biology will recognize that the therapeutic element may include, but is not limited to a promoter sequence, a poly(A) sequence, or a 3' or 5' UTR.

The term "tissue" as used herein refers to a collection of similar cells and the intercellular substances surrounding them. A skilled artisan recognizes that a tissue is an aggregation of similarly specialized cells for the performance of a particular function. For the scope of the present invention, the term tissue does not refer to a cell line, a suspension of cells, or a culture of cells. In a specific embodiment, the tissue is electroporated in vivo. In another embodiment, the tissue is not a plant tissue. A skilled artisan recognizes that there are four basic tissues in the body: 1) epithelium; 2) connective tissues, including blood, bone, and cartilage; 3) muscle tissue; and 4) nerve tissue. In a specific embodiment, the methods and compositions are directed to transfer new optimized plasmids into a muscle tissue by electroporation.

The term "transfects" as used herein refers to introduction of a nucleic acid into a eukaryotic cell. In some embodiments, the cell is not a plant tissue or a yeast cell.

The term "vector" as used herein refers to any vehicle that delivers a nucleic acid into a cell or organism. Examples include plasmid vectors, viral vectors, liposomes, or cationic lipids.

The term "viral backbone" as used herein refers to a nucleic acid sequence that does may contain a promoter, a gene, and a 3' poly A signal or an untranslated region, but contain elements including, but not limited at site-specific genomic integration Rep and inverted terminal repeats ("ITRs") or the binding site for the tRNA primer for reverse transcription, or a nucleic acid sequence component that induces a viral immunogenicity response when inserted in vivo, allows integration, affects specificity and activity of tissue specific promoters, causes transcriptional silencing or poses safety risks to the subject.

The new synthetic constructs of the current invention are injected intramuscularly into a correspondent species. For example, the porcine GHRH ("pGHRH") construct in any version is utilized in pigs. Although not wanting to be bound by theory, the porcine GHRH will be produced by the pig muscle fibers, and then secreted into the circulatory system. The circulating hormone will enhance the synthesis and secretion of porcine growth hormone in the anterior pituitary. The new synthetic constructs can promote long-term expression because the new plasmid backbone lacks CpG islands and other bacterial components, as bacterial promoters that alert the immune system of the presence of a foreign antigen. By decreasing the immune response against the plasmid fragment and its products can function in the muscle cells for longer durations of time, which lowers cost of treatment by decreasing the number of treatments. Furthermore, the usage of species-specific transgene will ensure long term expression by the lack of neutralizing antibodies against a foreign GHRH.

Plasmid-mediated supplementation. The delivery of specific genes to somatic tissue in a manner that can correct inborn or acquired deficiencies and imbalances has been demonstrated in prior art. Plasmid-mediated transgene supplementation for therapeutic purposes offers a number of advantages over the administration of recombinant proteins. These advantages include the conservation of native protein structure, improved biological activity, avoidance of systemic toxicities, and avoidance of infectious and toxic impurities. In addition, plasmid-mediated transgene supplementation allows for prolonged exposure to the protein in the therapeutic range, because the newly secreted protein is present continuously in the blood circulation.

Although not wanting to be bound by theory, the primary limitation of using a recombinant protein is the limited availability of protein after each administration. Plasmid mediated gene supplementation using injectable DNA plasmid expression vectors overcomes this drawback, because a single injection into the subject's skeletal muscle permits physiologic expression for extensive periods of time (Brown et al., 2004; Tone et al., 2004). Injection of the plasmids can promote the production of enzymes and hormones in animals in a manner that more closely mimics the natural process. Furthermore, among the non-viral techniques for gene transfer in vivo, the direct injection of plasmid DNA into muscle tissue is simple, inexpensive, and safe.

In a plasmid based expression system, a non-viral transgene vector may be composed of a synthetic gene delivery system in addition to the nucleic acid encoding a therapeutic gene product. In this way, the risks associated with the use of most viral vectors can be avoided. Additionally, no integration of plasmid sequences into host chromosomes has been reported in vivo to date, so that this type of gene transfer should neither activate oncogenes nor inactivate tumor suppressor genes (Ledwith et al., 2000b; Ledwith et al., 2000a). As episomal systems residing outside the chromosomes, plasmids have defined pharmacokinetics and elimination profiles, leading to a finite duration of gene expression in target tissues (Manam et al., 2000).

One aspect of the current invention is a new, versatile, and codon optimized plasmid based mammalian expression system that can be produced at high yields, which can be delivered to the target host and will reduce the adverse effects associated with prokaryotic nucleic acid sequences in mammalian hosts. In addition, this new plasmid will constitute the base of a species-specific library of plasmids for expression of hormones or other proteins for agricultural and companion animal applications. The synthetic expression plasmid of this invention has further reduced components compared to our and other previous applications, and has been optimized to increase efficacy, and reduce adverse reactions in vivo. In addition to a mammalian gene of interest, a typical nucleic acid delivery vehicle or synthetic expression plasmid contains many structural elements useful for the in vitro amplification of the plasmid in a bacterial host. The current invention involves a "synthetic plasmid backbone" ("pAV0201") (SEQ ID NO.: 2) that provides a clean lineage, which is useful for plasmid supplementation therapy in mammals. Furthermore, new plasmid backbones, such as "pAV0224" (SEQ ID NO.: 12), "pAV0225" (SEQ ID NO.: 13), "pAV0237" (SEQ ID NO.: 14), "pAV0242" (SEQ ID NO.: 15), and finally the "mut" family (SEQ ID NO.: 31-35) plasmid backbone family has been optimized for plasmid production, smaller than previous versions, and with optimized origin of replication.

A plasmid based mammalian expression system is minimally composed of a plasmid backbone, a synthetic delivery promoter in addition to the nucleic acid encoding a therapeutic expression product. A plasmid backbone typically contains a bacterial origin of replication, and a bacterial antibiotic selection gene, which are necessary for the specific growth of only the bacteria that are transformed with the proper plasmid. However, there are plasmids that lack both the antibiotic resistance gene and the origin of replication, such plasmids are called mini-circles (Darquet et al., 1997; Darquet et al., 1999; Soubrier et al., 1999). The use of in vitro amplified expression plasmid DNA (i.e. non-viral expression systems) avoids the risks associated with viral vectors. The non-viral expression systems products generally have low toxicity due to the use of "species-specific" components for gene delivery, which minimizes the risks of immunogenicity generally associated with viral vectors. One aspect of the current invention is a new, versatile, and codon optimized plasmid based mammalian expression system, which will constitute the base of a species-specific library of plasmids for expression of hormones or other proteins for agricultural and companion animal applications. For example, optimized synthetic sequences can be produced such that codon frequencies are matched in target and host organisms to ensure proper folding. A bias of GC content can be used to increase mRNA stability or reduce secondary structures. Tandem repeat codons or base runs that may impair the gene can be minimized with codon optimization. Modification of ribosome binding sites and mRNA degradation sites can be utilized. Optimization can also reduce or eliminate problem secondary structures within the transcribed mRNA, as well as optimizing RNAII activity.

Vectors. The term "vector" is used to refer to a carrier nucleic acid molecule into which a nucleic acid sequence can be inserted for introduction into a cell wherein, in some embodiments, it can be replicated. A nucleic acid sequence can be native to the animal, or it can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), linear DNA fragments, and artificial chromosomes (e.g., YACs), although in a preferred embodiment the vector contains substantially no viral sequences. One of skill in the art would be well equipped to construct a vector through standard recombinant techniques.

The term "expression vector" refers to a vector or nucleic acid expression construct containing a nucleic acid sequence coding for at least part of a gene product capable of being transcribed. In a specific embodiment the nucleic acid sequence encodes part or all of GHRH. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

In a preferred embodiment, the nucleic acid construction construct or vector of the present invention is a plasmid which comprises a synthetic myogenic (muscle-specific) promoter, a synthetic nucleotide sequence encoding a species specific growth hormone releasing hormone or its analogs, and a 3' untranslated region. In other alternative embodiments, optimized porcine growth hormone, optimized human growth hormone, optimized mouse growth hormone, optimized rat growth hormone, optimized bovine growth hormone, optimized ovine growth hormone, optimized chicken growth hormone, or skeletal alpha actin 3' untranslated regions are utilized in the vector.

Plasmid vectors. In certain embodiments, a linear DNA fragment from a plasmid vector is contemplated for use to transfect a eukaryotic cell, particularly a mammalian cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. Other plasmids contain genes for kanamycin or neomycin, or have a non-antibiotic selection mechanism. The pBR plasmid, or other microbial plasmid or phage must also contain, or be modified to contain, for example, promoters which can be used by the microbial organism for expression of its own proteins. A skilled artisan recognizes that any plasmid in the art may be modified for use in the methods of the present invention. In a specific embodiment, for example, a GHRH vector used for the therapeutic applications is derived from pBlueScript KS+ and has a kanamycin resistance gene.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S-transferase ("GST") soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB or its derivates. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 hours, the cells are collected by centrifugation and washed to remove residual media.

Promoters and Enhancers. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control" and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. For instance, in the timidine kinase (TK) promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

The distance between the eukaryotic promoter from the expression cassette and prokaryotic elements within plasmid backbone is also critical. In a specific embodiment in this application, we reduced the distance between the eukaryotic promoter SPc5-12 and the kanamycin resistance gene and control elements without impairment of plasmid production.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant, synthetic or heterologous promoter, which refers to a promoter that is not normally associated with a nucleic acid sequence in its natural environment. A recombinant, synthetic or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. Additionally, many Eukaryotic Promoter promoter/enhancer combination that would available to one of ordinary skill in the art could also be used to drive expression.

Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct. While most classic plasmids contain these elements, their usage is not always justified in highly specialized or optimized plasmids.

Tables 1 and 2 list non-limiting examples of elements/promoters that may be employed, in the context of the present invention, to regulate the expression of the eukaryotic RNA. Table 2 provides non-limiting examples of inducible elements, which are regions of a nucleic acid sequence that can be activated in response to a specific stimulus.

TABLE 1

| Promoter and/or Enhancer | |
|---|---|
| Promoter/Enhancer | Relevant References |
| β-Actin | (Kawamoto et al., 1988; Kawamoto et al., 1989) |
| Muscle Creatine Kinase (MCK) | (Horlick and Benfield, 1989; Jaynes et al., 1988) |
| Metallothionein (MTII) | (Inouye et al., 1994; Narum et al., 2001; Skroch et al., 1993) |
| Albumin | (Pinkert et al., 1987; Tronche et al., 1989) |
| β-Globin | (Tronche et al., 1990; Trudel and Costantini, 1987) |
| Insulin | (German et al., 1995; Ohlsson et al., 1991) |
| Rat Growth Hormone | (Larsen et al., 1986) |
| Troponin I (TN I) | (Lin et al., 1991; Yutzey and Konieczny, 1992) |
| Platelet-Derived Growth Factor (PDGF) | (Pech et al., 1989) |
| Duchenne Muscular Dystrophy | (Klamut et al., 1990; Klamut et al., 1996) |
| Cytomegalovirus (CMV) | (Boshart et al., 1985; Dorsch-Hasler et al., 1985) |
| Synthetic muscle specific promoters (c5-12, c1-28) | (Draghia-Akli et al., 1999; Draghia-Akli et al., 2002c; Li et al., 1999) |

TABLE 2

| Element/Inducer | |
|---|---|
| Element | Inducer |
| MT II | Phorbol Ester (TFA) |
| | Heavy metals |
| MMTV (mouse mammary tumor virus) | Glucocorticoids |
| β-Interferon | Poly(rI)x/Poly(rc) |
| Adenovirus 5 E2 | E1A |
| Collagenase | Phorbol Ester (TPA) |
| Stromelysin | Phorbol Ester (TPA) |
| SV40 | Phorbol Ester (TPA) |

TABLE 2-continued

| Element/Inducer | |
|---|---|
| Element | Inducer |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2 κb | Interferon |
| HSP70 | E1A, SV40 Large T Antigen |
| Proliferin | Phorbol Ester-TPA |
| Tumor Necrosis Factor α | PMA |
| Thyroid Stimulating Hormone α Gene | Thyroid Hormone |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Liu et al., 2000; Tsumaki et al., 1998), D1A dopamine receptor gene (Lee et al., 1997), insulin-like growth factor II (Dai et al., 2001; Wu et al., 1997), and human platelet endothelial cell adhesion molecule-1 (Almendro et al., 1996).

In a preferred embodiment, a synthetic muscle promoter is utilized, such as SPc5-12 (Li et al., 1999), which contains a proximal serum response element ("SRE") from skeletal α-actin, multiple MEF-2 sites, MEF-1 sites, and TEF-1 binding sites, and greatly exceeds the transcriptional potencies of natural myogenic promoters. The uniqueness of such a synthetic promoter is a significant improvement over, for instance, issued patents concerning a myogenic promoter and its use (e.g. U.S. Pat. No. 5,374,544) or systems for myogenic expression of a nucleic acid sequence (e.g. U.S. Pat. No. 5,298,422). In a preferred embodiment, the promoter utilized in the invention does not get shut off or reduced in activity significantly by endogenous cellular machinery or factors. Other elements, including trans-acting factor binding sites and enhancers may be used in accordance with this embodiment of the invention. In an alternative embodiment, a natural myogenic promoter is utilized, and a skilled artisan is aware how to obtain such promoter sequences from databases including the National Center for Biotechnology Information ("NCBI") GenBank database or the NCBI PubMed site. A skilled artisan is aware that these databases may be utilized to obtain sequences or relevant literature related to the present invention.

Initiation Signals and Internal Ribosome Binding Sites. A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) (Pelletier and Sonenberg, 1988) have been described, as well IRES from mammalian messages (Lyons and Robertson, 2003; Macejak and Sarnow, 1991; Martineau et al., 2004). IRES elements can be linked to heterologous open reading frames. Multiple open reading frames can be transcribed together, each separated by IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference)

Multiple Cloning Sites. Vectors can include a MCS, which is a nucleic acid region that contains multiple restriction enzyme sites, any of which can be used in conjunction with standard recombinant technology to digest the vector (see, for example, (Carbonelli et al., 1999; Cocea, 1997; Levenson et al., 1998) incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology, used and described herein in "Examples". While the regions are necessary for creating a library of multipurpose plasmids, their excessive presence, through numerous rounds of cloning parts of preexistent plasmids or fragments can potentially generate cryptic transcription initiation sites, stop codons, or other sequences that interfere with plasmid expression or production. Thus, in our new optimized plasmids cloning sites are kept to a necessary minimum.

Restriction Enzymes. In some embodiments of the present invention, a linear DNA fragment is generated by restriction enzyme digestion of a parent DNA molecule. The fragments are then ligated together, or with other newly produced linear DNA fragments, generating new plasmids or DNA fragments. Examples of restriction enzymes are provided below.

| Name | Recognition Sequence |
| --- | --- |
| Aat II | GACGTC |
| Acc65 I | GGTACC |
| Acc I | GTMKAC |
| Aci I | CCGC |
| Acl I | AACGTT |
| Afe I | AGCGCT |
| Afl II | CTTAAG |
| Afl III | ACRYGT |

-continued

| Name | Recognition Sequence |
| --- | --- |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| AnaL I | GTGCAC |
| Ano I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |

| Name | Recognition Sequence |
|---|---|
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp 1286 I | GDGCHC |
| BspD I | ATCGAT |
| BspE I | TCCGGA |
| BspH I | TCATGA |
| BsnM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |

| Name | Recognition Sequence |
|---|---|
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| EcoO109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYRAC |
| Hind III | AAGCTT |
| Hinf I | GANTC |
| HinP1 I | GCGC |
| Hpa I | GTTAAC |
| Hpa II | CCGG |
| Hph I | GGTGA |
| Kas I | GGCGCC |
| Kpn I | GGTACC |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |

-continued

| Name | Recognition Sequence |
|---|---|
| MsnA1 I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| N2oM1 V | GCCGGC |
| Nhe I | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| PleI | GAGTC |
| Pme I | GTTTAAAC |
| Pml I | CACGTG |
| PpuM I | RGGWCCY |
| PshA I | GACNNNNGTC |
| Psi I | TTATAA |
| PsaG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |

-continued

| Name | Recognition Sequence |
|---|---|
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TspR I | CAGTG |
| Tth111 I | GACNNNGTC |
| Xba I | TCTAGA |
| Xcm I | CCANNNNNNNNNTGG |
| Xho I | CTCGAG |
| Xma I | CCCGGG |
| Xmn I | GAANNNNTTC |

The term "restriction enzyme digestion" of DNA as used herein refers to catalytic cleavage of the DNA with an enzyme that acts only at certain locations in the DNA. Such enzymes are called restriction endonucleases and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µL of buffer solution. Appropriate buffers and substrate amounts for particular restriction enzymes are specified by the manufacturer. Restriction enzymes are used to ensure plasmid integrity and correctness. The specific restriction enzymes used in each reaction is given in the "Examples".

Splicing Sites. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see for example (Chandler et al., 1997).

Termination Signals. The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues or "poly(A)" to the 3'end of the transcript. RNA molecules modified with this poly(A) tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

Polyadenylation Signals. In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the bovine or human growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication. In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers. In certain embodiments of the invention, the cells that contain the nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker, such as the antibiotic resistance gene on the plasmid constructs (such as kanamycin, ampicylin, gentamycin, tetracycline, or chloramphenicol).

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Mutagenesis. Where employed, mutagenesis was accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Site-Directed Mutagenesis. Structure-guided site-specific mutagenesis represents a powerful tool for the dissection and engineering of protein-ligand interactions (Zheng and Kyle, 1996). The technique provides for the preparation and testing of sequence variants by introducing one or more nucleotide sequence changes into a selected DNA (Ryu and Nam, 2000).

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as $E.\ Coli$ polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as $E.\ coli$ cells, and clones are selected that include recombinant vectors bearing the mutated sequence arrangement. The shortcoming of this approach is that the logistics of multi-residue saturation mutagenesis are daunting. Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis. Other methods of site-directed mutagenesis are disclosed in U.S. Pat. Nos. 5,220,007; 5,284,760; 5,354,670; 5,366,878; 5,389,514; 5,635,377; and 5,789,166.

Alternatively, newer site-directed mutagenesis techniques can be used, such as "gene-trap mutagenesis". Gene-trap mutagenesis is a technique that randomly generates loss-of-function mutations and reports the expression of many mouse genes (Stanford et al., 2001). Alternatively, PCR can be used for side-directed mutagenesis (Jenkins et al., 1999). The PCR primers will contain the desired mutation, and the resulting fragment can be cloned in the plasmid using standard molecular biology techniques. This method was preferred and used in our "Examples".

Electroporation. A nucleic acid can be introduced into an organelle, a cell, a tissue or an organism via electroporation. Electroporation involves the exposure of a population of cells and DNA to an electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

The underlying phenomenon of electroporation is believed to be the same in all cases, but the exact mechanism responsible for the observed effects has not been elucidated. Although not wanting to be bound by theory, the overt manifestation of the electroporative effect is that cell membranes become transiently permeable to large molecules after the cells have been exposed to electric pulses. There are conduits through cell walls, which under normal circumstances maintain a resting transmembrane potential of circa 90 mV by allowing bi-directional ionic migration.

Although not wanting to be bound by theory, electroporation makes use of the same structures, by forcing a high ionic flux through these structures and opening or enlarging the conduits. In prior art, metallic electrodes are placed in contact with tissues and predetermined voltages, proportional to the distance between the electrodes are imposed on them. The protocols used for electroporation are defined in terms of the resulting field intensities, according to the formula $E=V/d$, where ("E") is the field, ("V") is the imposed voltage and ("d") is the distance between the electrodes.

The electric field intensity E has been a very important value in prior art when formulating electroporation protocols for the delivery of a drug or macromolecule into the cell of the subject. Accordingly, it is possible to calculate any electric field intensity for a variety of protocols by applying a pulse of predetermined voltage that is proportional to the distance between electrodes. However, a caveat is that an electric field can be generated in a tissue with insulated electrodes (i.e. flow of ions is not necessary to create an electric field). Although not wanting to be bound by theory, it is the current that is necessary for successful electroporation not electric field per se.

During electroporation, the heat produced is the product of the inter-electrode impedance, the square of the current, and the pulse duration. The protocols described in the art for electroporation are defined in terms of the resulting field intensities E, which are dependent on short voltage pulses of unknown current. Accordingly, the resistance or heat generated in a tissue cannot be determined, which leads to varied success with different pulsed voltage electroporation protocols with predetermined voltages. The ability to limit heating of cells across electrodes can increase the effectiveness of any given electroporation voltage pulsing protocol. For example, prior art teaches the utilization of an array of six needle electrodes utilizing a predetermined voltage pulse across opposing electrode pairs. This situation sets up a centralized pattern during an electroporation event in an area where congruent and intersecting overlap points develop. Excessive heating of cells and tissue along electroporation path will kill the cells, and limit the effectiveness of the protocol. However, symmetrically arranged needle electrodes without opposing pairs can produce a decentralized pattern during an electroporation event in an area where no congruent electroporation overlap points can develop.

Controlling the current flow between electrodes allows one to determine the relative heating of cells. Thus, it is the current that determines the subsequent effectiveness of any given pulsing protocol and not the voltage across the electrodes. Predetermined voltages do not produce predetermined currents, and prior art does not provide a means to determine the exact dosage of current, which limits the usefulness of the technique. Thus, controlling an maintaining the current in the tissue between two electrodes under a threshold will allow one to vary the pulse conditions, reduce cell heating, create less cell death, and incorporate macromolecules into cells more efficiently when compared to predetermined voltage pulses.

Overcoming the above problem by providing a means to effectively control the dosage of electricity delivered to the cells in the inter-electrode space by precisely controlling the ionic flux that impinges on the conduits in the cell membranes. The precise dosage of electricity to tissues can be calculated as the product of the current level, the pulse length and the number of pulses delivered. Thus, a specific embodiment of the present invention can deliver the electroporative current to a volume of tissue along a plurality of paths without, causing excessive concentration of cumulative current in any one location, thereby avoiding cell death owing to overheating of the tissue.

Although not wanting to be bound by theory, the nature of the voltage pulse to be generated is determine by the nature of tissue, the size of the selected tissue and distance between electrodes. It is desirable that the voltage pulse be as homogenous as possible and of the correct amplitude. Excessive field strength results in the lysing of cells, whereas low field strength results in reduced efficacy of electroporation. Some electroporation devices utilize the distance between electrodes to calculate the electric field strength and predetermined voltage pulses for electroporation. This reliance on knowing the distance between electrodes is a limitation to the design of electrodes. Because the programmable current pulse controller will determine the impedance in a volume of tissue between two electrodes, the distance between electrodes is not a critical factor for determining the appropriate electrical current pulse. Therefore, an alternative embodiment of a needle electrode array design would be one that is non-symmetrical. In addition, one skilled in the art can imagine any number of suitable symmetrical and non-symmetrical needle electrode arrays that do not deviate from the spirit and scope of the invention. The depth of each individual electrode within an array and in the desired tissue could be varied with comparable results. In addition, multiple injection sites for the macromolecules could be added to the needle electrode array.

One example of an electroporation device that may be used to effectively facilitate the introduction of a macromolecule, including optimized plasmids, into cells of a selected tissue of a subject was described in U.S. patent application Ser. No. 10/657,725 filed on Sep. 8, 2003, titled "Constant Current Electroporation Device And Methods Of Use," with Smith et al., listed as inventors, the entirety of which is hereby incorporated by reference. The electroporation device comprises an electro-kinetic device ("EKD") whose operation is specified by software or firmware. The EKD produces a series of programmable constant-current pulse patterns between electrodes in an array based on user control and input of the pulse parameters and allows the storage and acquisition of current waveform data. The electroporation device also comprises a replaceable electrode disk having an array of needle electrodes, a central injection channel for an injection needle, and a removable guide disk.

Without being bound to the theory, the combination of a well-designed plasmid vector with an efficacious delivery method can ensure long-lasting plasmid expression after in vivo treatment with proteins expressed at therapeutic levels.

The invention may be better understood with reference to the following examples which are representative of some of the embodiments of the invention, and are not intended to limit the invention.

Example 1

Optimized Plasmid Backbone "pAV0201"

One aspect of the current invention is the optimized plasmid backbone. The new synthetic plasmids presented below contain eukaryotic sequences that are synthetically optimized for species-specific mammalian transcription. Each of the following examples described a step of optimization, each resulting in a new and improved family of plasmids.

Figure 2:
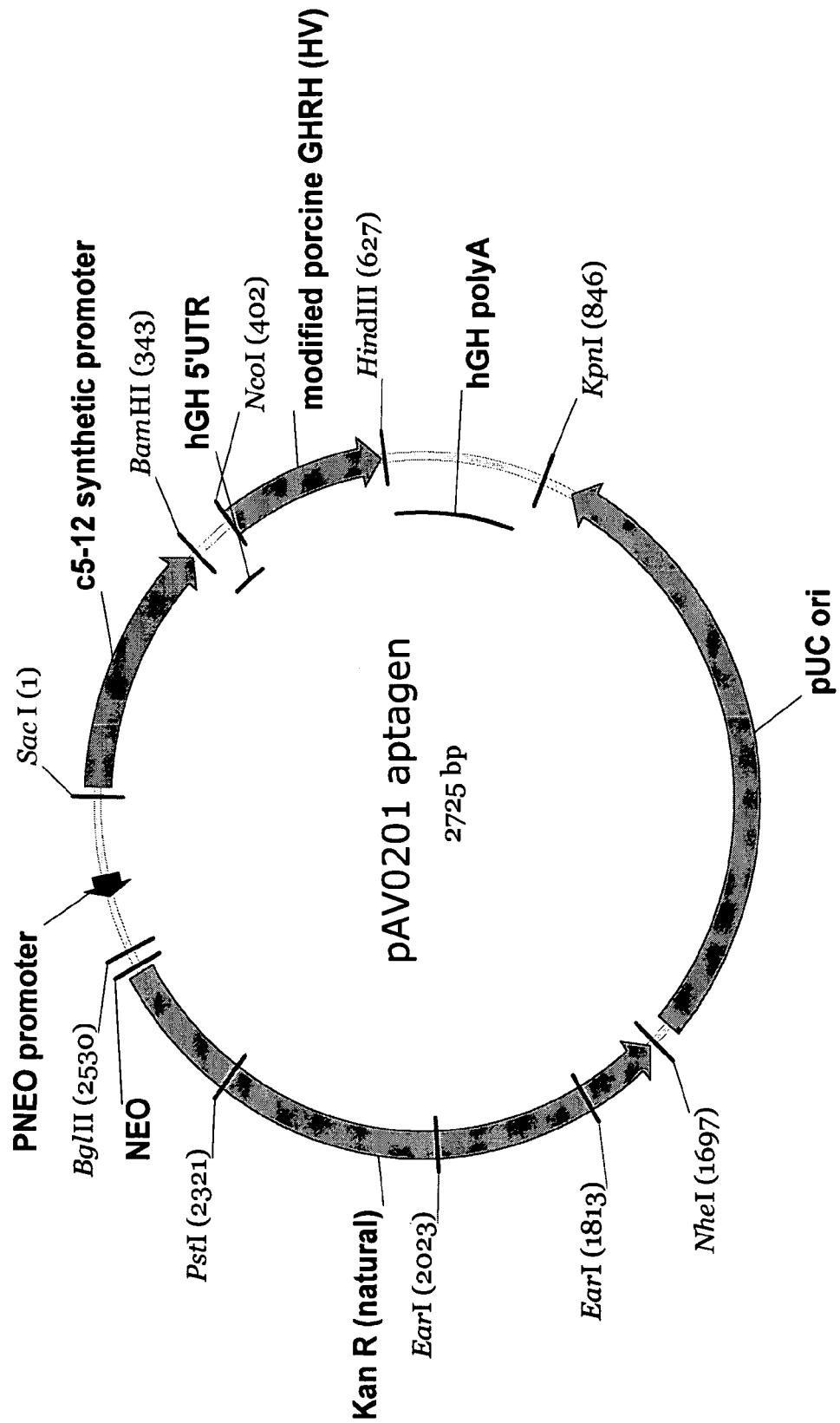
FIG. 2 shows a general map of a synthetic plasmid construct "pAV0201"; this construct contains the porcine modified GHRH called HV-GHRH of the current invention, which contains codon-optimization.
Figure 3:
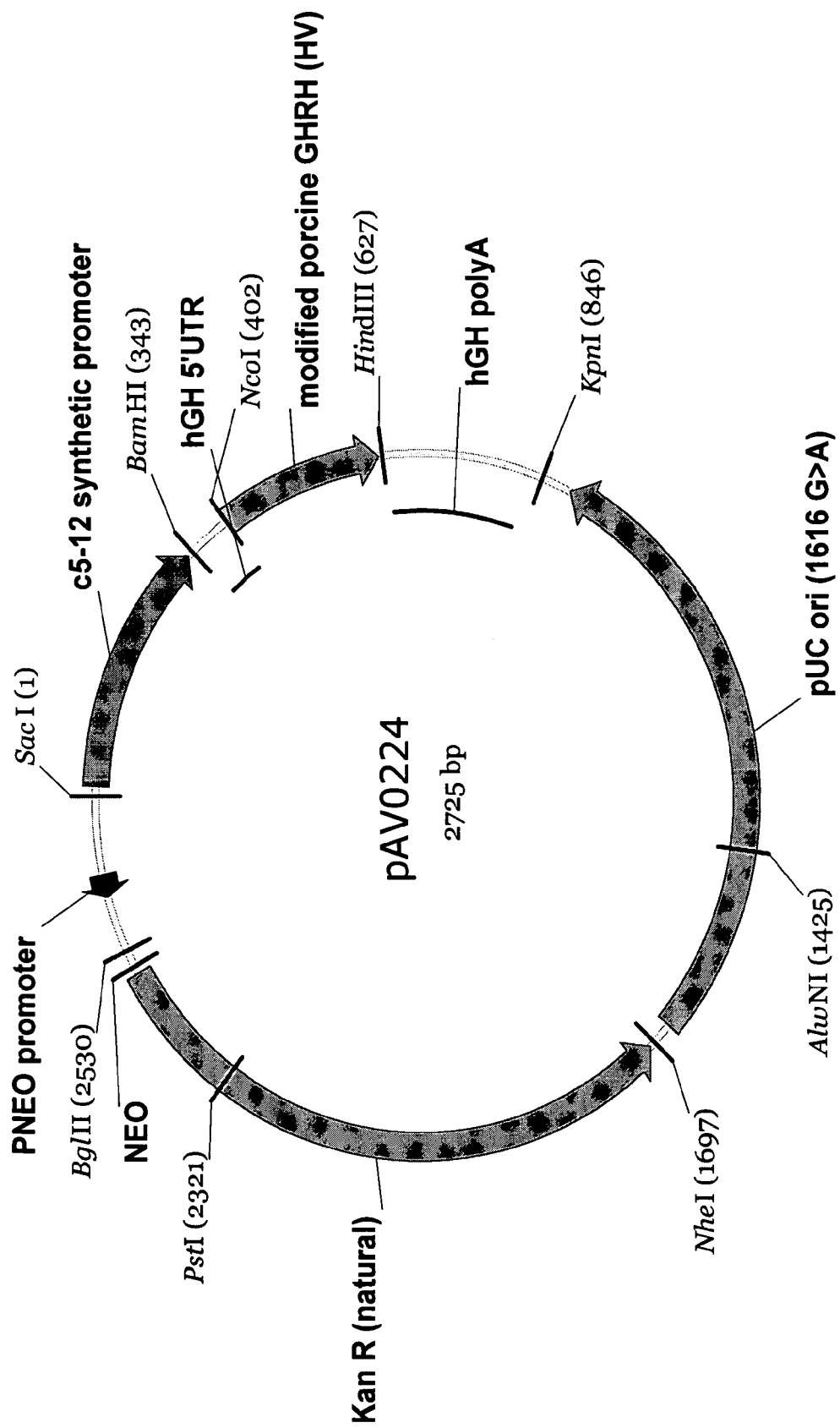
FIG. 3 shows a general map of a synthetic plasmid construct "pAV0224"; this construct contains the porcine modified GHRH called HV-GHRH of the current invention, which contains codon-optimization, and improved origin of replication.
Figure 4:
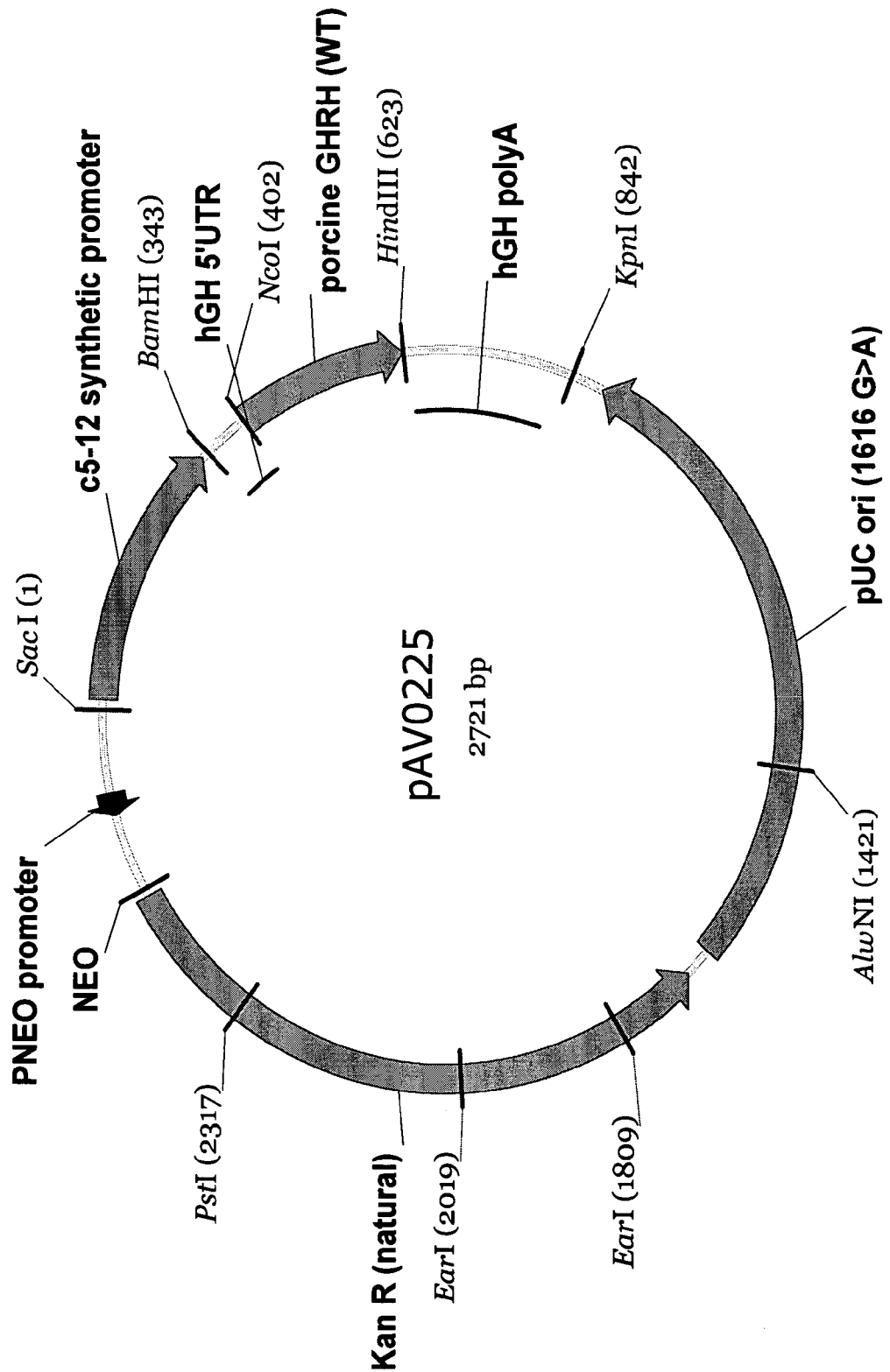
FIG. 4 shows a general map of a synthetic plasmid construct "pAV0225"; this construct contains the porcine wild-type GHRH called wt-GHRH of the current invention, which contains codon-optimization, and improved origin of replication.
Figure 5:
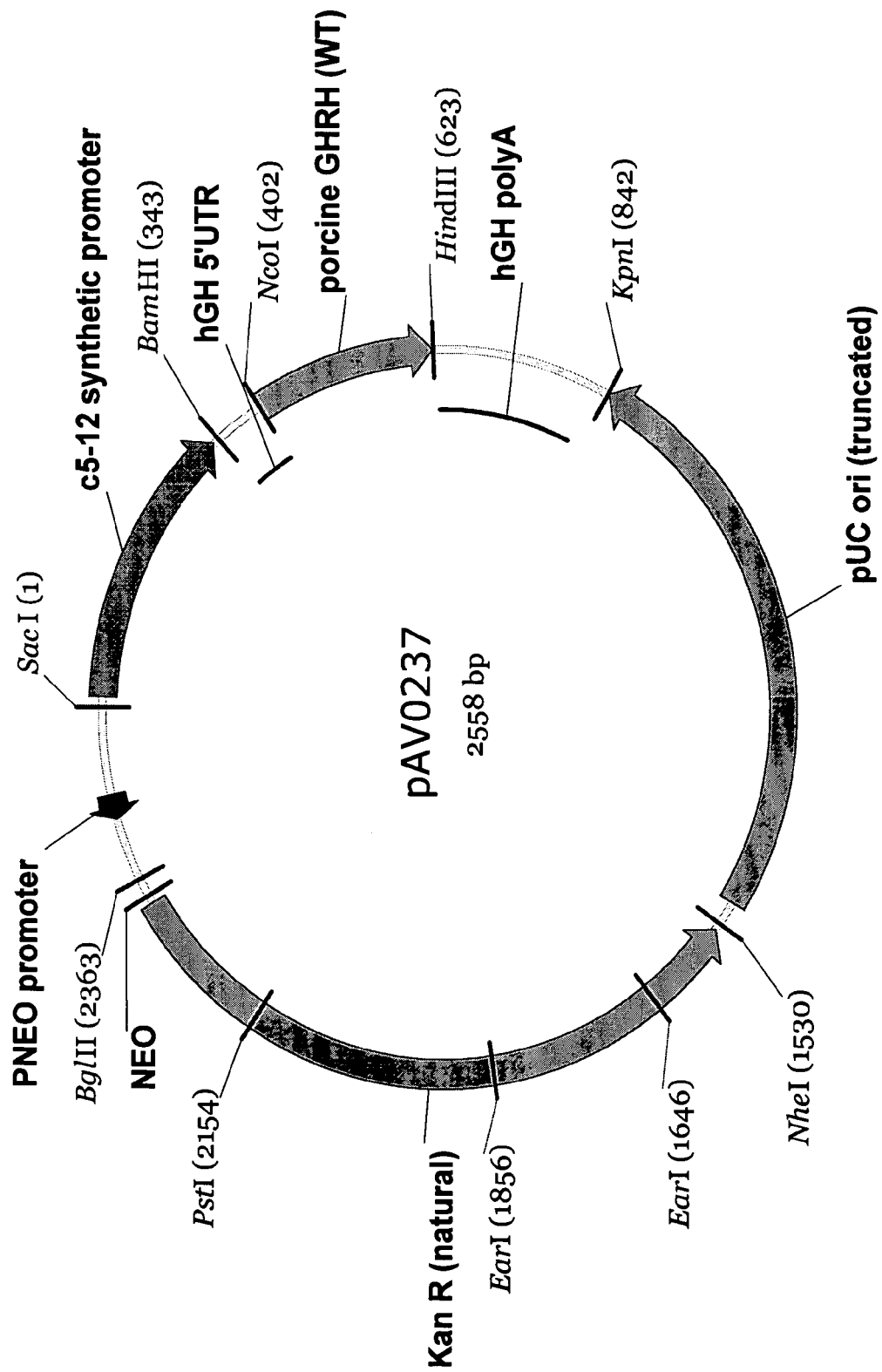
FIG. 5 shows a general map of a synthetic plasmid construct "pAV0237"; this construct contains the porcine wild-type GHRH called wt-GHRH of the current invention, which contains codon-optimization, and improved origin of replication, including deletions in the 3'end of "ori"
Figure 6:
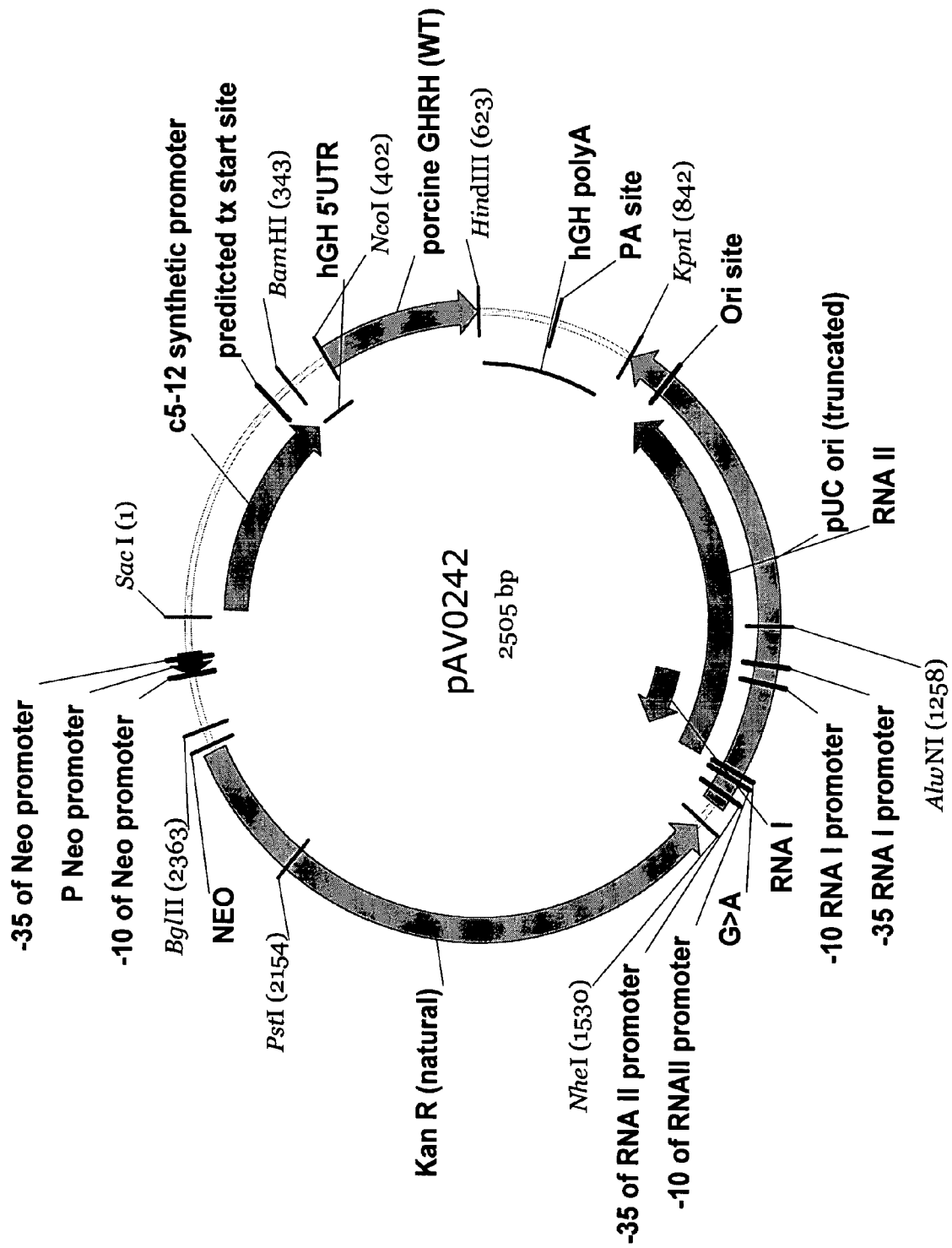
FIG. 6 shows a general map of a synthetic plasmid construct "pAV0242"; this construct contains the porcine wild-type GHRH called wt-GHRH of the current invention, which contains codon-optimization, and improved origin of replication, including deletions in the 3'end of "ori" and in regions located between the eukaryotic expression cassette and the kanamycin resistance gene.

An existing pSP-HV-GHRH plasmid ("pAV0125") (SEQ ID NO.: 1), as shown in FIG. 1 was synthetically optimized to form a new plasmid ("pAV0201")(SEQ ID NO.: 2), as shown in FIG. 2. The plasmid pAV0125 was described in U.S. patent application Ser. No. 09/624,268 filed on Jul. 24, 2000 and entitled "Super Active Porcine Growth Hormone Releasing Hormone Analog" with Schwartz, et al., listed as inventors, ("the Schwartz '268 application"). This 3,534 bp plasmid pAV0125 (SEQ ID NO.: 1) contains a plasmid backbone with various component from different commercially available plasmids, for example, a synthetic promoter SPc5-12 (SEQ ID NO.: 3), a modified porcine GHRH sequence (SEQ ID NO.: 4), and a 3'end of human growth hormone (SEQ ID NO.: 5).

The new optimized synthetic expression vector "pAV0201" described in U.S. patent application Ser. No. 10/619,939 filed on Jul. 15, 2003 and entitled "Codon-optimized synthetic plasmids" with Draghia-Akli et al. listed as inventors (the '939 application), consists of 2,713 bp and is shown in FIG. 2. The therapeutic encoded gene for the optimized plasmid in FIG. 2 may also include optimized nucleic acid sequences that encode the following modified GHRH molecules:

| ENCLODED GHRH AMINO ACID SEQUENCE | | |
|---|---|---|
| Wt-pig-GHRH | YADAIFTNSYRKVLGQLSARKLLQDIMSRQQGERNQEQGA-OH | (SEQ ID NO.: 17) |
| HV-GHRH | HVDAIFTNSYRKVLAQLSARKLLQDILNRQQGERNQEQGA-OH | (SEQ ID NO.: 18) |
| TI-GHRH | YIDAIFTNSYRKVLAQLSARKLLQDILNRQQGERNQEQGA-OH | (SEQ ID NO.: 19) |
| TV-GHRH | YVDAIFTNSYRKVLAQLSARKLLQDILNRQQGERNQEQGA-OH | (SEQ ID NO.: 20) |
| 15/27/28-GHRH | YADAIFTNSYRKVLAQLSARKLLQDILNRQQGERNQEQGA-OH | (SEQ ID NO.: 21) |
| Bovine-GHRH | YADAIFTNSYRKVLGQLSARKLLQDIMNRQQGERNQEQGA-OH | (SEQ ID NO.: 22) |
| Dog-GHRH | YADAIFTNSYRKVLGQLSARKLLQDIMSRQQGERNREQGA-OH | (SEQ ID NO.: 23) |
| Cat-GHRH | YADAIFTNSYRKVLGQLSARKLLQDIMSRQQGERNQEQGA-OH | (SEQ ID NO.: 24) |
| Ovine-GHRH | YADAIFTNSYRKILGQLSARKLLQDIMNRQQGERNQEQGA-OH | (SEQ ID NO.: 25) |
| Chicken-GHRH | HADGIFSKAYRKLLGQLSARNYLHSLMAKRVGSGLGDEAEPLS-OH | (SEQ ID NO.: 26) |

-continued

| ENCLODED GHRH AMINO ACID SEQUENCE | | |
|---|---|---|
| Horse-GHRH (partial) | -ADAIFTNNYRKVLGQLSARKILQDIMSR-----------OH | (SEQ ID NO.: 27) |
| Human-GHRH(1-40)OH | YADAIFTNSYRKVLGQLSARKLLQDIMSRQQGESNQERGA-OH | (SEQ ID NO.: 28) |
| Human-GHRH(1-44)NH2 | YADAIFTNSYRKVLGQLSARKLLQDIMSRQQGESNQERGARARL-NH$_2$ | (SEQ ID NO.: 29) |

In general, the encoded GHRH or functional biological equivalent thereof is of formula:

(SEQ ID NO.: 30)
-$X_1$-$X_2$-DAIFTNSYRKVL-$X_3$-QLSARKLLQDI-$X_4$-$X_5$-RQQGE-$X_6$-N-$X_7$-E-$X_8$-GA-OH wherein: $X_1$ is a D- or L-isomer of an amino acid selected from the group consisting of tyrosine ("Y"), or histidine ("H"); $X_2$ is a D- or L-isomer of an amino acid selected from the group consisting of alanine ("A"), valine ("V"), or isoleucine ("I"); $X_3$ is a D- or L-isomer of an amino acid selected from the group consisting of alanine ("A") or glycine ("G"); $X_4$ is a D- or L-isomer of an amino acid selected from the group consisting of methionine ("M"), or leucine ("L"); $X_5$ is a D- or L-isomer of an amino acid selected from the group consisting of serine ("S") or asparagines ("N"); $X_6$ is a D- or L-isomer of an amino acid selected from the group consisting of arginine ("R"), or serine ("S"); $X_7$ is a D- or L-isomer of an amino acid selected from the group consisting of arginine ("R"), or glutamine ("Q"); and $X_8$ is a D- or L-isomer of an amino acid selected from the group consisting of arginine ("R"), or glutamine ("Q").

An example of this new optimized synthetic expression vector was denoted as pAV0201 (SEQ ID NO.: 2). In order to construct pAV0201 (SEQ ID NO.: 2), some unwanted sequences from the pAV0125 (SEQ ID NO.: 1) were initially removed. A software program called Vector NTI (version 7.0) was used to generate and match sequences that could be compared and were known to be extraneous (e.g. LacZ promoter). There are many programs such as Vector NTI (version 7.0) that are known in the art and could have been used with similar results to compare and identify specific nucleic acid sequences. Once the extraneous DNA sequences were identified in the pAV0125 plasmid, they were removed by from the plasmid creating a truncated-pAV0125 plasmid. The Gene Forge® optimized synthetic sequences were used to produced codon frequencies that were matched in target and host organisms to ensure proper folding. Gene Forge® was also used to identify and correct a number of deleterious structural elements in the relevant nucleic acid sequences. For example, a bias of GC content can be used to increase mRNA stability or reduce secondary structures; tandem repeat codons or base runs that may impair the gene can be minimized with codon optimization; modification of ribosome binding sites and mRNA degradation sites can be utilized; codon optimization can also reduce or eliminate problem secondary structures within the transcribed mRNA. Although Gene Forge® is a proprietary product of Aptagen that speeds codon optimization analysis, publicly available databases are available that allow a person with average skill in the art to replicate codon optimization protocol.

The pAV0125 plasmid contained a human growth hormone polyadenylation region (SEQ ID NO.: 5) that was approximately 618 bp. The original 618 bp region contained multiple polyadenylation sites and was reduced to only one. As a result over 400 bp were removed to an optimized length of 190 bp (SEQ ID NO.: 10). The origin of replication (SEQ ID NO.: 11) was not altered.

A summary of the changes made to the pAV0125 plasmid backbone changes are as follows:

1. Although not wanting to be bound by theory, CpG islands are known to enhance immune responses, and are used to bust immune responses in vaccines (Manders and Thomas, 2000; McCluskie et al., 2000; Scheule, 2000). The Gene Forge® system identified and removed as many CpG island as possible without changing the translated amino acid sequence. A Nco I site was removed from the kanamycin sequence without altering the amino acid sequence. Currently the NcoI became a unique site, which makes the plasmid backbone more versatile.

2. The lacZ promoter region that was located downstream of the hGH polyA site was determined to be unnecessary, and it was subsequently removed.

3. A portion of the hGH poly(A) region was removed to produce a more compact plasmid that is able to accommodate longer DNA fragments or transgenes.

4. A 118 bp portion of the lacZ coding sequence that was located between the kanamycin resistance gene and the C5-12 synthetic promoter was determined to be unnecessary, and it was subsequently removed.

As a result of the above modifications to the plasmid backbone, a new synthetic plasmid as shown in FIG. 2 was constructed. The pAV0201 optimized plasmid comprises a 2,713 bp circular plasmid. The pAV0201 plasmid contains at least one eukaryotic coding region, and at least one prokaryotic coding sequence, wherein it has been contemplated that the eukaryotic coding region contains a modified growth hormone releasing hormone ("GHRH"). The pAV0201 plasmid also contains a poly(A) signal, wherein the human growth hormone poly(A) has been utilized. The pAV0201 plasmid also contains a eukaryotic promoter, and it has been contemplated that the c5-12 synthetic eukaryotic promoter will be used, although other may be equally useful. The pAV0201 also contains a prokaryotic promoter. The prokaryotic promoter is PNEO, and a 19-47 bp sequence of transposon fragment ("Tn5") with GenBank accession number V00618. Additionally one NEO ribosome binding site ("RBS") is present in the pAV0201 plasmid. A complementary origin of replication sequence ("pUC ori") from the pUC18 plasmid (e.g. 685-1466 bp of pUC18). A 5' untranslated region ("5'UTR") was inserted into the pAV0201 plasmid. The 5'UTR is from human growth hormone hGH 5' UTR (i.e. 504-557 bp) GenBank accession number M13438.

Example 2

Optimized Plasmid Backbones "pAV0224" and "pAV0237"

The plasmid "pAV0201" was found to have a mutation at position 1581, which changed one nucleotide, "A" present in the wild-type origin of replication with a "G". The mutation was considered to potentially diminish the plasmid yield compared to the theoretical calculated plasmid yield. Thus, this mutation was corrected by mutagenesis and the newly created plasmid was called "pAV0224" (SEQ ID NO.: 12). The plasmid contained the plasmid backbone, and the expression cassette with the synthetic promoter SPc5-12, the cDNA encoding for the HV-GHRH analog and the 3'UTR and poly (A) signal of GH.

Site specific mutagenesis was performed by overlap extension PCR. Two rounds of PCR were performed to yield the final product. The upper and lower primers contained the base pair changes (A to G sense).

```
                                         (SEQ ID NO: 43)
Upper primer:
5'GGTAGCTCTTGATCCGGCAAACAAACCACCGCTGG3'

(SEQ ID NO: 44)
Lower primer:
5'CCAGCGGTGGTTTGTTTGCCGGATCAAGAGCTACC3'

(SEQ ID NO: 45)
NheI primer:
5'CGAGTTCTTCTGAGCGCTAGCTGAG3'

(SEQ ID NO: 46)
AlwNI primer:
5'CACTGGCAGCAGCCACTGGTAACAG3'
```

Initial PCR reactions were performed with the "upper" and NheI 3' primers and the "lower" and AlwNI 5'primers. The PCR reaction mix was as following: pAV0201 template—21 ng, 50 ng of each primer, Ready Mix Taq Polymerase with MgCl$_2$ (Sigma, St. Louis, Mo.), sterile water to 50 μL total volume. The initial PCR cycling parameters were: a heat start at 95° C. for 8 minutes, followed by 30 cycles of 94° C. for 30 seconds, 55° C. for 30 seconds, 72° C. for 40 seconds, and finished with a cycle ay 72° C. for 5 minutes. The PCR reaction was performed in a PE Applied Biosystems Gene Amp PCR System 9700.

Gel purifies PCR products were used as template in second round of PCR to generate the final 307 bp product containing the A to G single point mutation. The PCR reaction mix for this second round of amplification was: product from initial PCR used as template –30-50 ng of each purified fragment, 50 ng of each primer, Ready Mix Taq Polymerase with MgCl$_2$ (Sigma, St. Louis, Mo.), sterile water to 50 μL total volume. PCR cycling parameters were: a heat start at 95° C. for 8 minutes, followed by 30 cycles of 94° C. for 30 seconds, 55° C. for 30 seconds, 72° C. for 40 seconds, and finished with a cycle ay 72° C. for 5 minutes. The final fragment with the correct A to G mutation was cloned into pCR4Blunt-TOPO vector (Invitrogen, Carlsbad, Calif.) and sequenced prior to cloning into pAV0201 vector via TaKara DNA Ligation protocol. The final plasmid was 2725 bp and included the expression cassette.

During construction of this plasmid, a new mutation at position 1620 bp which changed a "G" to an "A" was introduced in the origin of replication, affecting RNA II polymerase activity. This particular mutation boosted the plasmid yield by 28% versus the parental backbone, 4.1 mg/L versus 3.2 mg/L of culture.

The newly built plasmid backbone is multifunctional and was further used clone in the cDNA of the porcine wild-type GHRH, to generate plasmid "pAV0225". Briefly, the porcine wild-type GHRH cDNA was inserted into the NcoI/HindIII site of the pAV0224 backbone, replacing the NcoI/HindIII fragment of HV-GHRH, to generate pAV0225 (SEQ ID NO.: 13). This new plasmid was 2721 bp in length.

In an effort to further render the plasmid backbone smaller, we used the "sir_graph" web application by Stewart and Zuker to predict the RNA II polymerase folding in the context of our plasmid (Zuker, 2003). We identified that a 163 bp fragment at the 3'end of the origin of replication could be deleted, without negatively impacting the functionality of the origin of replication. From pAV0225, we deleted the AflIII/Acc65I region of the pUC ori 3'end which also contains the T3 promoter, to generate the new plasmid described as "pAV0237" (SEQ ID NO.: 14). This newly produced plasmid was only 2558 bp, while fully functional.

Example 3

New Versatile Optimized Plasmid Backbone "pAV0242"

A 53 bp deletion was made between the BglII and SacI sites of the pAV0237 plasmid to yield the new "pAV0242" (SEQ ID NO.: 15) plasmid that is 2505 bp while still including the GHRH coding sequence. The region deleted contained extraneous bacterial nucleotide sequence from the T7 promoter and some E. coli LacZ coding region. Removal of these sequences resulted in a plasmid 30% smaller than pAV0125, and 8% smaller than pAV0201, thus having the capacity to accommodate larger transgenes or cDNA fragments, while increasing plasmid yields and integrity.

Methods—Plasmid Construct—The plasmid "pAV0242" was synthesized by cloning in a synthetic 145 bp fragment into the BglII/SacI sites of pAV0237, while deleting the existing fragment. The synthetic BglII/SacI fragment had the 53 bp deletion (SEQ ID NO.: 16). The remainder of the plasmid was unchanged—SPc5-12 synthetic promoter, human 5' untranslated (5'UTR) region followed by porcine GHRH coding sequence and the 3' untranslated region and poly(A) signal of the human GH gene.

Example 4

RNA II Promoter Mutations and Origin of Replication Optimization

RNA II is stimulating replication of ColE1-derived plasmids which is inhibited by RNA I. Increasing the RNA II to RNA I ratio should increase the frequency of DNA replication initiation events, which should yield higher plasmid copy number. The danger is the production of levels of RNA II that are so elevated that they would lead to "runaway" plasmid replication. Thus, strict control of the relative potency of these sequences is necessary. By introducing targeted substitutions in the bacterial origin of replication, one can increase plasmid yield and decrease fermentation time, thus increasing productivity.

Two rounds of PCR were used to generate the mutations in the RNA II promoter regions. The initial PCR primers contain the desired mutations in both the forward and reverse sequence. All primers were synthesized by Sigma Aldrich, The Woodlands, Tex. The forward (upper) primers (included below) were run with the NheI primer to generate an approximate 90 bp band. The reverse (lower) primers were run with the AlwNI primer to generate an approximate 250 bp band. The PCR reaction mix was separated by electrophoresis and the 90 bp and 250 bp bands were gel purified using the StrataPrep DNA Gel Extraction Kit (Stratagene, La Jolla, Calif.) and the product used as template in the second PCR.

AlwNI and NheI primers were used in the second round of PCR to generate a final 272 bp fragment. These fragments were cloned to replace the existing fragment in the origin of replication, and generate the "ori" high yield mutants. In all cases 44 ng of template were used for the second PCR reaction. Only mutations that had at least the same growth characteristics as the parental pAV0242 were included in this application. While a larger number of mutants were screened, some mutations resulted in plasmids that could not grow under standard conditions, proving that some mutations in the origin of replication can be detrimental.

Wild-Type

Gtttttttgtttacaagcagcagat-tacgcgcagaaaaaaaggatctcaagaagatcctttgatcttttc (SEQ ID NO: 47) —this sequence is contained within the origin of replication sequence (SEQ ID NO.: 11). An example of this sequence in a plasmid can be found in the Ori of (SEQ ID NOs.: 12, 13, 14, and 15).

Mutant 1 gtttttttgtttacaagcagcatat-tacgcgcagaaaaaaaggatctcaagaagatcctttgatcttttc (SEQ ID NO: 48) —this sequence is contained within the origin of replication designated as "mut 1" (SEQ ID NO.: 37). An example of this sequence in a plasmid can be found in the Ori of (SEQ ID NO.: 31).

Mutant 2

Gtttttttgtttacaagcagcagtt-tacgcgcagaaaaaaaggatctcaagaagatcctttgatcttttc (SEQ ID NO: 49) —this sequence is contained within the origin of replication designated as "mut 2" (SEQ ID NO.: 38). An example of this sequence in a plasmid can be found in the Ori of (SEQ ID NO.: 32)

Mutant 3

Gtttttttttgtttacaagcagca-gaatacgcgcagaaaaaaaggatctcaagaagatcctttgatcttttc (SEQ ID NO: 50) —this sequence is contained within the origin of replication designated as "mut 3" (SEQ ID NO.: 39). An example of this sequence in a plasmid can be found in the Ori of (SEQ ID NO.: 33)

Mutant 8 gtttttttgtttacaagcagcattt-tacgcgcagaaaaaaaggatctcaagaagatcctttgatcttttc (SEQ ID NO: 51) —this sequence is contained within the origin of replication designated as "mut 8" (SEQ ID NO.: 40). An example of this sequence in a plasmid can be found in the Ori of (SEQ ID NO.: 34)

Mutant 9 gtttttttgtttacaagcagcat-aatacgcgcagaaaaaaaggatctcaagaagatcctttgatcttttc (SEQ ID NO: 52) —this sequence is contained within the origin of replication designated as "mut 9" (SEQ ID NO.: 41). An example of this sequence in a plasmid can be found in the Ori of (SEQ ID NO.: 35)

Primer sequence: Mutation 1—to generate this G to T mutation at position −9 in the RNAII promoter the following set of primers was used: forward 5'GCAGCATATTACGCGCAG 3' (SEQ ID NO: 53) and reverse 5'CTGCGCGTAATATGCTGC 3' (SEQ ID NO: 54). The initial PCR cycling parameters were: a heat start at 95° C. for 8 minutes, followed by 30 cycles of 94° C. for 30 seconds, 53° C. for 30 seconds, 72° C. for 40 seconds, and finished with a cycle ay 72° C. for 5 minutes. The second PCR parameters were: a heat start at 95° C. for 8 minutes followed by 30 cycles of 94° C. for 30 seconds, 55° C. for 30 seconds, 72° C. for 40 seconds, and finished with a cycle ay 72° C. for 5 minutes.

Primer sequence: Mutation 2—to generate this A to T mutation at −10 in the RNAII promoter the following set of primers was used: forward 5'GCAGCAGTTTACGCGCAG 3' (SEQ ID NO: 55) and reverse 5'GCGCGTAAACTGCTGCTTG 3' SEQ ID NO: 56). The initial PCR cycling parameters were: a heat start at 95° C. for 8 minutes, followed by 30 cycles of 94° C. for 30 seconds, 64° C. for 30 seconds, 72° C. for 40 seconds, and finished with a cycle ay 72° C. for 5 minutes. The second PCR parameters were: a heat start at 95° C. for 8 minutes followed by 30 cycles of 94° C. for 30 seconds, 55° C. for 30 seconds, 72° C. for 40 seconds, and finished with a cycle ay 72° C. for 5 minutes.

Primer sequence: Mutation 3—to generate this T to A mutation at −11 in the RNAII promoter the following set of primers was used: forward 5'GCAGCAGAATACGCGCAG 3' (SEQ ID NO: 57) and reverse 5'GCGCGTATTCTGCTGCTTG 3'(SEQ ID NO: 58). The initial PCR cycling parameters were: a heat start at 95° C. for 8 minutes, followed by 30 cycles of 94° C. for 30 seconds, 64° C. for 30 seconds, 72° C. for 40 seconds, and finished with a cycle ay 72° C. for 5 minutes. The second PCR parameters were: a heat start at 95° C. for 8 minutes followed by 30 cycles of 94° C. for 30 seconds, 55° C. for 30 seconds, 72° C. for 40 seconds, and finished with a cycle ay 72° C. for 5 minutes.

Primer sequence: Mutation 8—to generate this G to T mutation at −9 and A to T mutation at −10 in the RNAII promoter the following set of primers was used: forward 5'CAAGCAGCATTTTACGCGCAG3' (SEQ ID NO: 59) and reverse 5'CTGCGCGTAAAATGCTGCTTG3' (SEQ ID NO: 60). The initial PCR cycling parameters were: a heat start at 95° C. for 8 minutes, followed by 30 cycles of 94° C. for 30 seconds, 56° C. for 30 seconds, 72° C. for 40 seconds, and finished with a cycle ay 72° C. for 5 minutes. The second PCR parameters were: a heat start at 95° C. for 8 minutes followed by 30 cycles of 94° C. for 30 seconds, 55° C. for 30 seconds, 72° C. for 40 seconds, and finished with a cycle ay 72° C. for 5 minutes.

Primer sequence: Mutation 9- to generate this G to T mutation at −9 and T to A mutation at −11 in the RNAII promoter the following set of primers was used: forward 5'CAAGCAGCATAATACGCGCAG3' (SEQ ID NO: 61) and reverse 5'CTGCGCGTATTATGCTGCTTG3' (SEQ ID NO: 62). The initial PCR cycling parameters were: a heat start at 95° C. for 8 minutes, followed by 30 cycles of 94° C. for 30 seconds, 56° C. for 30 seconds, 72° C. for 40 seconds, and finished with a cycle ay 72° C. for 5 minutes. The second PCR parameters were: a heat start at 95° C. for 8 minutes followed by 30 cycles of 94° C. for 30 seconds, 55° C. for 30 seconds, 72° C. for 40 seconds, and finished with a cycle ay 72° C. for 5 minutes.

Primer sequence: AlwNI universal forward primer had the following sequence: 5'GCAGCAGCCACTGGTAACAGGATTAG3' (SEQ ID NO: 63)

Primer sequence: NheI universal reverse primer had the following sequence: 5'CGAGTTCTTCTGAGCGCTAGCTGAG3' (SEQ ID NO: 64)

Fragments determined to have the correct sequence were cloned into the AlwNI/Nhe site of pAV0242 to generate the new family of plasmids "mut". Briefly, the pAV0242 plasmid and correct mini-prep DNA were digested with AlwNI and Nhe I enzymes (NEB, Beverly, Mass.) to generate the vector and insert fragments for ligation. The fragments were gel purified with StrataPrep DNA Gel Extraction Kit (Stratagene, La Jolla, Calif.). The vector was dephosphorylated with Antarctic Phosphatase (NEB, Beverly, Mass.) and the ligation was carried out with TaKara's DNA Ligation Kit (TaKara Mirus Bio. Inc., Madison, Wis.).

Figure 7:
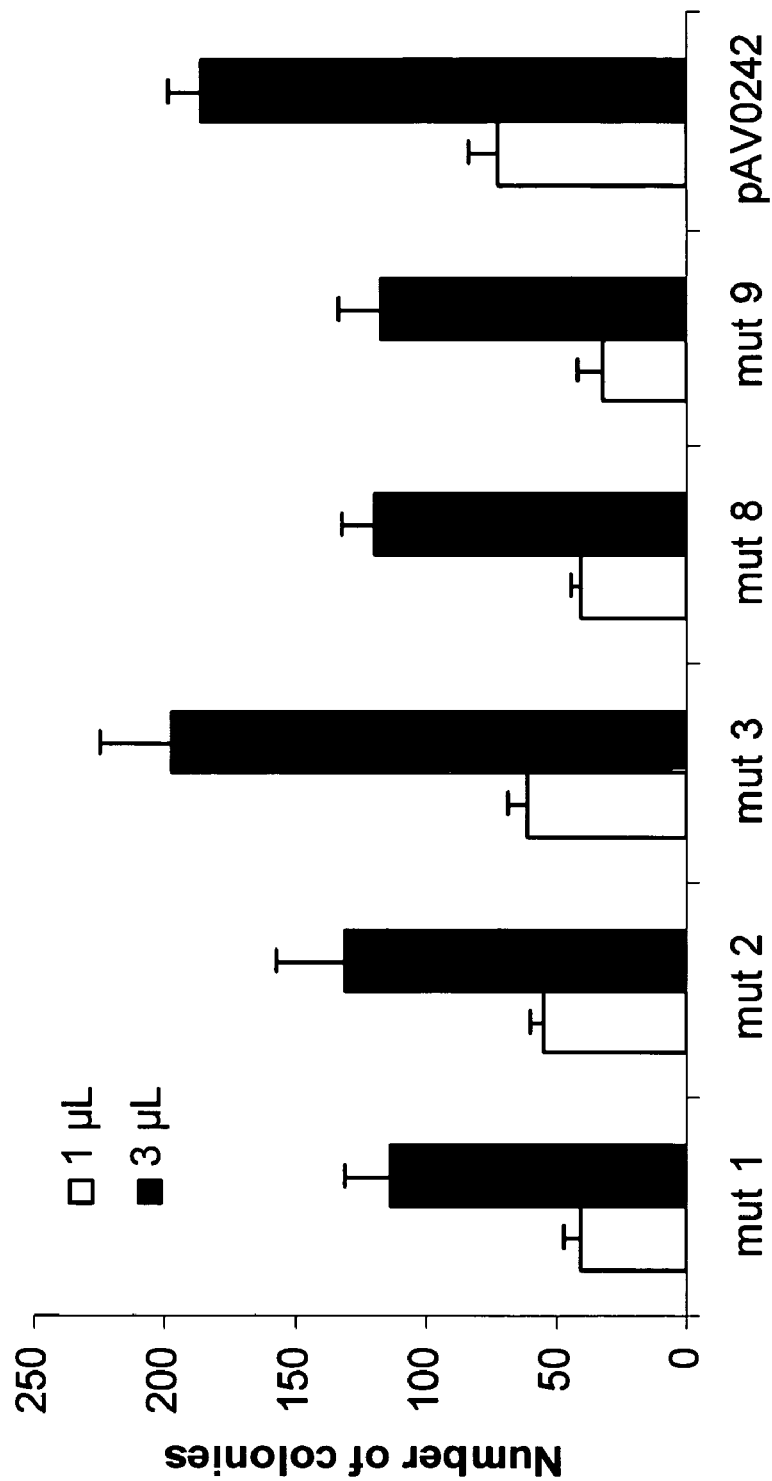
FIG. 7 shows the number of colonies obtained after transformation of origin of replication mutants: mut1, mut 2, mut 3, mut 8 and mut 9, compared to the number of colonies obtained after transformation of the newly produced plasmid "pAV0242".

Aliquots of 1 or 3 µL of each ligation was plated on at least three different LB/agar plates with 50 µg/mL kanamycin, and incubated over-night at 37° C. The number of colonies on each plate was counted the next day, and the average number of colonies is given (FIG. 7). The number of colonies generated was similar between all groups, with the exception of mutant 1 that had significantly lowed average number of colonies per plate, indicator of poor growth and performance under selection conditions.

The effectiveness and results of combination of mutations was unpredictable, and was assessed only after the sequence was synthetically generated and tested. As a proof, we have designed and tested some 10 other mutants that would have changed the −35 sequence present in the pUC plasmids "TTGAGA" to the consensus sequence "TTGACA" described in numerous other plasmids. In all this cases, 0 to 3 colonies were obtained on each plate, and no growth of the transformed bacteria was observed under selection conditions. We thus concluded that under the sequence/structure present in our plasmids, changes to the −35 element are detrimental.

Figure 8:
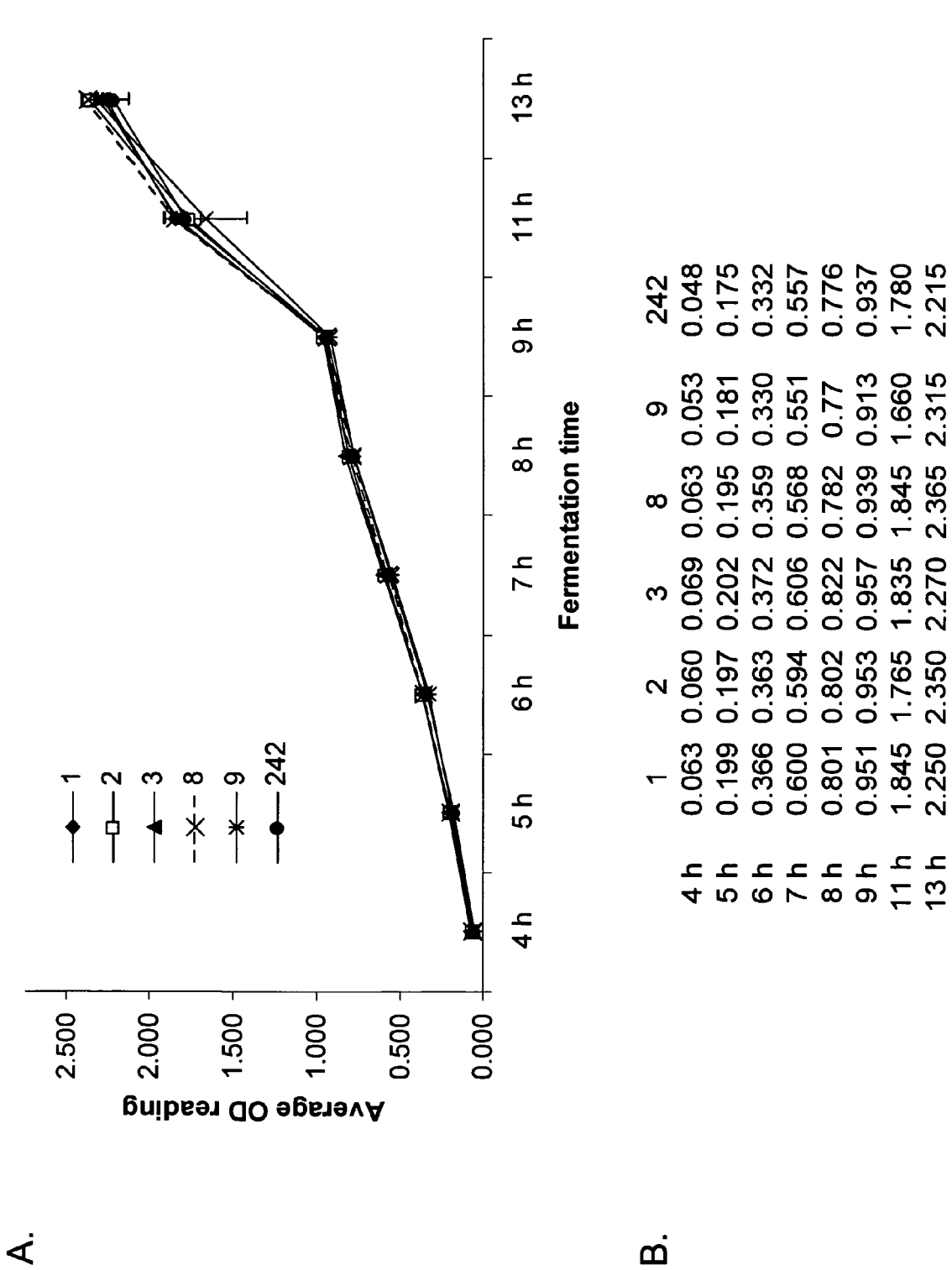
FIG. 8 shows the average optic density (OD) readings obtained during fermentation of plasmids containing the origin of replication mutants: mut1, mut 2, mut 3, mut 8 and mut 9, compared to the optic density (OD) readings obtained during fermentation of the newly produced plasmid "pAV0242".

Growth studies were performed to determine plasmid yields. All 5 plasmids with mutations in the RNAII promote were diluted to 10 ng/µL. Equal amounts were used to transform competent E. coli DH5α's. Different amounts of the transformation reaction were plated in triplicate and colony counts were done on each plate to give an average number of colonies per plasmid. From these plates, colonies were picked for overnight cultures in 5 mL of growth media. From these cultures, 100 mL of LB broth/kanamycin was inoculated with 100 µL of overnight culture, in duplicate. Timed optical density readings were taken at 4, 5, 6, 7, 8, 9, 11 and 13 hours to generate a growth curve (see FIG. 8). As depicted in FIGS. 8A and 8B, all the mutants had better growth patterns after 13 hours of fermentation than the pAV0242, the parental backbone.

Figure 9:
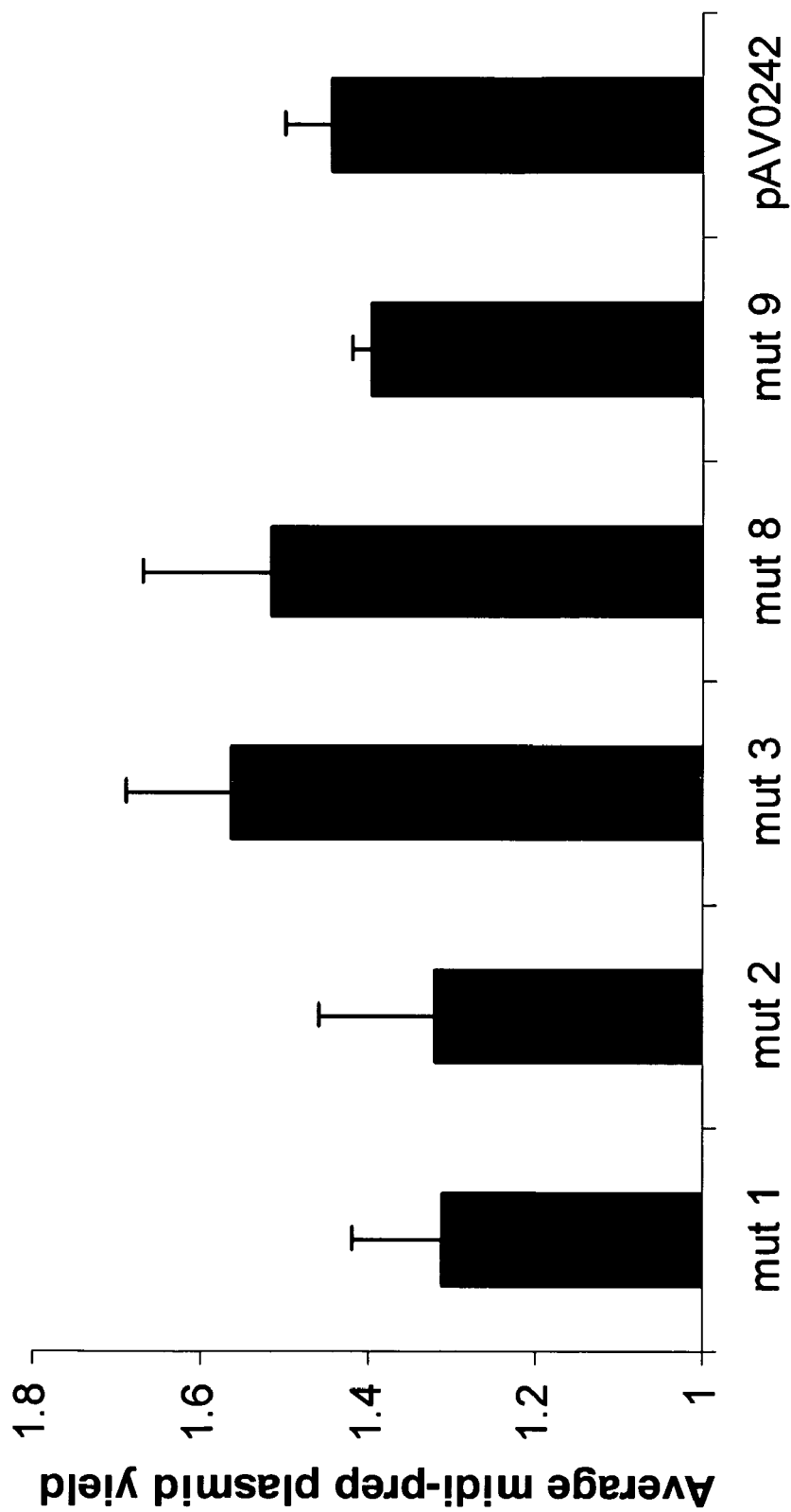
FIG. 9 shows the average midi-prep plasmid yields obtained after fermentation of plasmids containing the origin of replication mutants: mut1, mut 2, mut 3, mut 8 and mut 9, compared average midi-prep plasmid yields obtained after fermentation of the newly produced plasmid "pAV0242".
Figure 10:
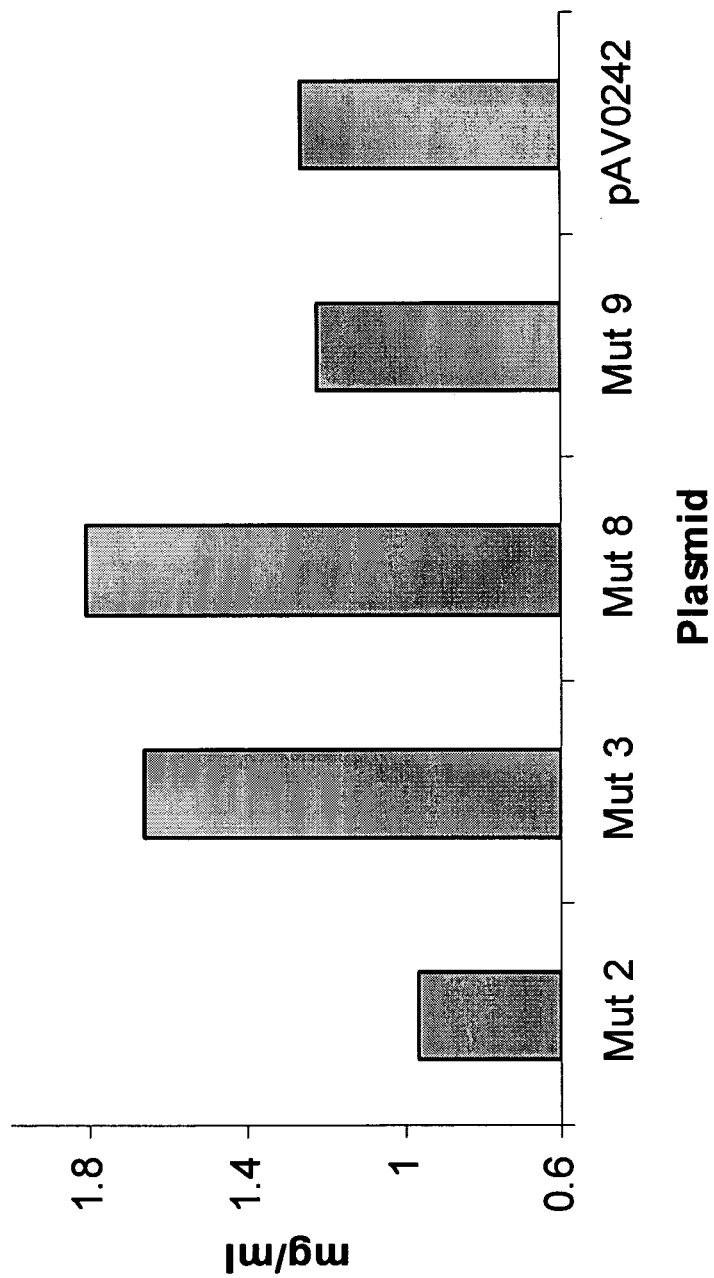
FIG. 10 shows the average giga-prep plasmid yields obtained after fermentation of plasmids containing the origin of replication mutants: mut1, mut 2, mut 3, mut 8 and mut 9, compared average giga-prep plasmid yields obtained after fermentation of the newly produced plasmid "pAV0242".

The remaining culture volume was used to isolate plasmid DNA to determine estimates for plasmid yield using procedures described in the manufacturer's manual for Stratagene mini-prep kit (Stratagene, La Jolla, Calif.) (3 mL culture volume) or Qiagen midi-prep kit (Qiagen, Valencia, Calif.) (45 mL culture volume). Average plasmid yield from the midi-prep purifications are given in FIG. 9. As shown, plasmids containing origin of replication with mutations 3 and 8 gave better plasmids yield (8.3 and 5%, respectively) when compared to the parental backbone pAV0242. FIG. 10 shows similar results when giga-preps (similar to large-scale fermentation) are employed—plasmids containing the origin of replication "mut 3" gave a 30% increase in plasmid yield, while plasmids containing the origin of replication "mut 8" gave a 42% increase in plasmid yield.

The above optimized plasmid constructs can be administered to a mammalian host for various therapeutic effects. One skilled in the art recognizes that different methods of delivery may be utilized to administer an optimized synthetic expression vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or a transporter molecule.

Accordingly, the present invention provides a method of creating plasmids with small optimized backbones capable of accommodating large transgenes, with increased plasmid yields and decreased fermentation times, which ultimately can be transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These compositions and methods described herein are by no means all-inclusive, and further methods to suit the specific application will be apparent to the ordinary skilled artisan. Moreover, the effective amount of the compositions can be further approximated through analogy to compounds known to exert the desired effect.

REFERENCES CITED

The entire content of each of the following U.S. patent, foreign patent and publication documents is incorporated by reference herein.

Australian Patent 772,752 titled "SUPER PORCINE GROWTH HORMONE RELEASING HORMONE ANALOG," issued on Aug. 20, 2004.

Australian Patent 770,982 titled "IGF-1 EXPRESSION SYSTEM AND METHODS OF USE," issued on Jun. 24, 2004

U.S. Pat. No. 6,551,996 titled "SUPER-ACTIVE PORCINE GROWTH HORMONE RELEASING HORMONE ANALOG," issued on Apr. 22, 2003.

U.S. Pat. No. 5,374,544 titled "MUTATED SKELETAL ACTIN PROMOTER," issued on Dec. 20, 1994.

U.S. Pat. No. 6,423,693 titled "GROWTH HORMONE RELEASING HORMONE EXPRESSION SYSTEM AND METHODS OF USE, INCLUDING USE IN ANIMALS, issued on Jul. 23, 2002

U.S. Pat. No. 6,410,228 titled "METHOD FOR THE IDENTIFICATION OF SYNTHETIC CELL-OR-TISSUE-SPECIFIC TRANSCRIPTIONAL REGULATORY REGIONS," issued on Jun. 25, 2002.

U.S. Pat. No. 5,298,422, titled "MYOGENIC VECTOR SYSTEMS," issued on Mar. 29, 1994.

U.S. Pat. No. 5,756,264, titled "MYOGENIC VECTOR SYSTEMS," issued on May 26, 1998.

U.S. Pat. No. 5,925,564 titled "MYOGENIC VECTOR SYSTEMS," issued on Jul. 20, 1999.

U.S. Pat. No. 5,364,791 titled "PROGESTERONE RECEPTOR HAVING C. TERMINAL HORMONE BINDING DOMAIN TRUNCATIONS," issued on Nov. 15, 1994.

U.S. Pat. No. 5,874,534 titled "PROGESTERONE RECEPTOR HAVING C. TERMINAL HORMONE BINDING DOMAIN TRUNCATIONS," issued on Feb. 23, 1999.

U.S. Pat. No. 5,935,934 titled "PROGESTERONE RECEPTOR HAVING C. TERMINAL HORMONE BINDING DOMAIN TRUNCATIONS," issued on Aug. 10, 1999.

U.S. Pat. No. 6,040,295 titled "FORMULATED NUCLEIC ACID COMPOSITIONS AND METHODS OF ADMINISTERING THE SAME FOR GENE THERAPY," issued on Mar. 21, 2000.

U.S. Pat. No. 4,822,470 titled "METHOD OF AND APPARATUS FOR CELL PORATION AND CELL FUSION USING RADIOFREQUENCY ELECTRICAL PULSES," issued on Apr. 18, 1989.

U.S. Pat. No. 4,970,154 titled "METHOD OF AND APPARATUS FOR CELL PORATION AND CELL FUSION USING RADIOFREQUENCY ELECTRICAL PULSES," issued on Nov. 13, 1990.

U.S. Pat. No. 5,304,486 titled "METHOD OF AND APPARATUS FOR CELL PORATION AND CELL FUSION USING RADIOFREQUENCY ELECTRICAL PULSES," issued on Apr. 19, 1994.

U.S. Pat. No. 6,551,996 issued on Apr. 23, 2003 and titled "SUPER ACTIVE PORCINE GROWTH HORMONE RELEASING HORMONE ANALOG," with Schwartz, et al., listed as inventors.

U.S. Pat. No. 6,114,148 issued on Sep. 5, 2000 and titled "HIGH LEVEL EXPRESSION OF PROTEINS," with Seed, et al., listed as inventors.

U.S. Pat. No. 5,292,721 issued on Mar. 8, 1994 and titled "USE OF GROWTH HORMONE TO ENHANCE PORCINE FETAL ENERGY AND SOW LACTATION PERFORMANCE," with Boyd, et al., listed as inventors.

U.S. Pat. No. 5,134,120 issued on Jul. 28, 1992 and titled "USE OF GROWTH HORMONE TO ENHANCE PORCINE WEIGHT GAIN," with Boyd, et al., listed as inventors.

U.S. Pat. No. 5,061,690 issued on Oct. 29, 1991 and titled "METHOD FOR INCREASING MILK PRODUCTION IN MAMMALS AND/OR INCREASING THE BIRTH WEIGHT OF THEIR NEWBORN AND IMPROVING POSTNATAL GROWTH," with Kann, et al., listed as inventors.

U.S. patent application Ser. No. 10/237,146 Titled "LINEAR DNA FRAGMENTS FOR GENE EXPRESSION" filed on Sep. 6, 2002.

U.S. patent application Ser. No. 10/021,403 Titled "ADMINISTRATION OF NUCLEIC ACID SEQUENCE TO FEMALE ANIMAL TO ENHANCE GROWTH IN OFFSPRING," filed on Dec. 12, 2001.

U.S. patent application Ser. No. 10/281,067 titled "A COMPOSITION AND METHOD TO ALTER LEAN BODY MASS AND BONE PROPERTIES IN A SUBJECT," filed on Oct. 25, 2002.

U.S. patent application Ser. No. 10/315,907 titled "PLASMID MEDIATED SUPPLEMENTATION FOR TREATING CHRONICALLY ILL SUBJECTS," filed on Dec. 10, 2002.

U.S. patent application Ser. No. 10/359,919 titled "MODIFIED PITUITARY GLAND DEVELOPMENT IN OFFSPRING FROM EXPECTANT MOTHER ANIMALS TREATED WITH GROWTH HORMONE RELEASING HORMONE THERAPY," filed on Feb. 6, 2003.

U.S. patent application Ser. No. 10/360,768 titled "ELECTRODE ASSEMBLY FOR CONSTANT-CURRENT ELECTROPORATION AND USE," filed on Mar. 7, 2002.

U.S. patent application Ser. No. 10/657,725 titled "ELECTRODE ASSEMBLY FOR CONSTANT-CURRENT ELECTROPORATION AND USE," filed on Sep. 8, 2003.

U.S. patent application Ser. No. 10/395,709 titled "INCREASED DELIVERY OF A NUCLEIC ACID CONSTRUCT IN VIVO BY THE POLY-L-GLUTAMATE ("PLG") SYSTEM," filed on Mar. 24, 2003.

U.S. patent application Ser. No. 10/619,939 titled "CODON OPTIMIZED SYNTHETIC PLASMIDS," filed on Jul. 15, 2003.

U.S. patent application Ser. No. 10/166,356 titled "PROTEASE RESISTANT TI-GROWTH HORMONE RELEASING HORMONE ("GHRH")," filed on Aug. 21, 2002.

U.S. patent application Ser. No. 10/699,597 titled "SYNTHETIC MUSCLE PROMOTERS WITH ACTIVITIES EXCEEDING NATURALLY OCCURRING REGULATORY SEQUENCES IN CARDIAC CELLS," filed on Oct. 30, 2003.

U.S. patent application Ser. No. 10/764,818 titled "REDUCING CULLING IN HERD ANIMALS GROWTH HORMONE RELEASING HORMONE (GHRH)," filed on Jan. 26, 2004.

U.S. patent application Ser. No. 10/798,896 titled "INSULIN-LIKE GROWTH FACTOR (IGF-1) PLASMID-MEDIATED SUPPLEMENTATION FOR THERAPEUTIC APPLICATIONS," filed on Mar. 11, 2004.

U.S. patent application Ser. No. 10/827,918, titled "PLASMID MEDIATED GHRH SUPPLEMENTATION FOR RENAL FAILURES," filed on Apr. 20, 2004.

U.S. patent application Ser. No. 10/857,439 titled "DEVICES AND METHODS FOR BIOMATERIAL PRODUCTION," filed on May 27, 2004.

U.S. patent application Ser. No. 10/894,644 titled "CANINE-SPECIFIC GROWTH HORMONE RELEASING HORMONE," filed on Jul. 20, 2004.

U.S. patent application Ser. No. 11/015,935 titled "REDUCING ARTHRITIS AND LAMENESS IN SUBJECTS BY GROWTH HORMONE RELEASING HORMONE ("GHRH") SUPPLEMENTATION," filed on Dec. 17, 2004.

United States Patent Application TBA, titled "ENHANCED SECRETION/RETENTION OF GROWTH HORMONE RELEASING HORMONE (GHRH) FROM MUSCLE CELLS BY SPECIES-SPECIFIC SIGNAL PEPTIDE, Attorney Docket Number (108328.0249).

U.S. Patent Application 60/590,739 Titled "GROWTH HORMONE RELEASING HORMONE ENHANCES VACCINATION RESPONSE, filed on Jul. 23, 2004.

NON-PATENT REFERENCE LIST

Acsadi, G., G. Dickson, D. R. Love, A. Jani, F. S. Walsh, A. Gurusinghe, Wolff, J A, and K. E. Davies. 1991. Human dystrophin expression in mdx mice after intramuscular injection of DNA constructs. Nature 352:815-818.

Aihara, H. and J. Miyazaki. 1998. Gene transfer into muscle by electroporation in vivo. Nat. Biotechnol. 16:867-870.

Almendro, N., T. Bellon, C. Rius, P. Lastres, C. Langa, A. Corbi, and C. Bemabeu. 1996. Cloning of the human platelet endothelial cell adhesion molecule-1 promoter and its tissue-specific expression. Structural and functional characterization. J. Immunol. 157:5411-5421.

Aratani, Y., R. Okazaki, and H. Koyama. 1992. End extension repair of introduced targeting vectors mediated by homologous recombination in mammalian cells. Nucleic Acids Res. 20:4795-4801.

Babiuk, L. A., R. Pontarollo, S. Babiuk, B. Loehr, and van Drunen Littel-van den Hurk. 2003. Induction of immune responses by DNA vaccines in large animals. Vaccine 21:649-658.

Bert, A. G., J. Burrows, C. S. Osborne, and P. N. Cockerill. 2000. Generation of an improved luciferase reporter gene plasmid that employs a novel mechanism for high-copy replication. Plasmid 44:173-182.

Bettan, M., F. Emmanuel, R. Darteil, J. M. Caillaud, F. Soubrier, P. Delaere, D. Branelec, A. Mahfoudi, N. Duverger, and D. Scherman. 2000. High-level protein secretion into blood circulation after electric pulse-mediated gene transfer into skeletal muscle. Mol. Ther. 2:204-210.

Boshart, M., F. Weber, G. Jahn, K. Dorsch-Hasler, B. Fleckenstein, and W. Schaffner. 1985. A very strong enhancer is located upstream of an immediate early gene of human cytomegalovirus. Cell 41:521-530.

Brown, P. A., W. C. Davis, and R. Draghia-Akli. 2004. Immune enhancing effects of growth hormone releasing hormone delivered by plasmid injection and electroporation. Molecular Therapy 10:644-651.

Bujard, H., C. Baldari, M. Brunner, U. Deuschle, R. Gentz, J. Hughes, W. Kammerer, and D. Stuber. 1983. Integration of efficient promoters of the *E. coli* system into plasmid vectors. Gene Amplif. Anal. 3:65-87.:65-87.

Carbonelli, D. L., E. Corley, M. Seigelchifer, and J. Zorzopulos. 1999. A plasmid vector for isolation of strong promoters in *Escherichia coli*. FEMS Microbiol. Lett. 177:75-82.

Chandler, S. D., A. Mayeda, J. M. Yeakley, A. R. Krainer, and X. D. Fu. 1997. RNA splicing specificity determined by the coordinated action of RNA recognition motifs in SR proteins. Proc. Natl. Acad. Sci. U.S.A 94:3596-3601.

Cocea, L. 1997. Duplication of a region in the multiple cloning site of a plasmid vector to enhance cloning-mediated addition of restriction sites to a DNA fragment. Biotechniques 23:814-816.

Dai, B., H. Wu, E. Holthuizen, and P. Singh. 2001. Identification of a novel cis element required for cell density-dependent down-regulation of insulin-like growth factor-2 P3 promoter activity in Caco2 cells. J. Biol. Chem. 276: 6937-6944.

Danko, I. and J. A. Wolff. 1994. Direct gene transfer into muscle. [Review]. Vaccine 12:1499-1502.

Darquet, A. M., B. Cameron, P. Wils, D. Scherman, and J. Crouzet. 1997. A new DNA vehicle for nonviral gene delivery: supercoiled minicircle. Gene Ther. 4:1341-1349.

Darquet, A. M., R. Rangara, P. Kreiss, B. Schwartz, S. Naimi, P. Delaere, J. Crouzet, and D. Scherman. 1999. Minicircle: an improved DNA molecule for in vitro and in vivo gene transfer. Gene Ther. 6:209-218.

Dasgupta, S., H. Masukata, and J. Tomizawa. 1987. Multiple mechanisms for initiation of ColE1 DNA replication: DNA synthesis in the presence and absence of ribonuclease H. Cell 51:1113-1122.

Davis, H. L., R. G. Whalen, and B. A. Demeneix. 1993. Direct gene transfer into skeletal muscle in vivo: factors affecting efficiency of transfer and stability of expression. Human Gene Therapy 4:151-159.

Deuschle, U., W. Kammerer, R. Gentz, and H. Bujard. 1986. Promoters of *Escherichia coli*: a hierarchy of in vivo strength indicates alternate structures. EMBO J. 5:2987-2994.

Dolnik, V., M. Novotny, and J. Chmelik. 1993. Electromigration behavior of poly-(L-glutamate) conformers in concentrated polyacrylamide gels. Biopolymers 33:1299-1306.

Dorsch-Hasler, K., G. M. Keil, F. Weber, M. Jasin, W. Schaffner, and U. H. Koszinowski. 1985. A long and complex enhancer activates transcription of the gene coding for the highly abundant immediate early mRNA in murine cytomegalovirus. Proc. Natl. Acad. Sci. U.S.A 82:8325-8329.

Draghia-Akli, R., K. M. Ellis, L. A. Hill, P. B. Malone, and M. L. Fiorotto. 2003. High-efficiency growth hormone releasing hormone plasmid vector administration into skeletal muscle mediated by electroporation in pigs. FASEB J 17:526-528.

Draghia-Akli, R., M. L. Fiorotto, L. A. Hill, P. B. Malone, D. R. Deaver, and R. J. Schwartz. 1999. Myogenic expression of an injectable protease-resistant growth hormone-releasing hormone augments long-term growth in pigs. Nat. Biotechnol. 17:1179-1183.

Draghia-Akli, R., K. A. Hahn, G. K. King, K. Cummings, and R. H. Carpenter. 2002a. Effects Of Plasmid Mediated Growth Hormone Releasing Hormone In Severely Debilitated Dogs With Cancer. Molecular Therapy 6:830-836.

Draghia-Akli, R., A. S. Khan, K. K. Cummings, D. Parghi, R. H. Carpenter, and P. A. Brown. 2002b. Electrical Enhancement of Formulated Plasmid Delivery in Animals. Technology in Cancer Research & Treatment 1:365-371.

Draghia-Akli, R., X. G. Li, and R. J. Schwartz. 1997. Enhanced growth by ectopic expression of growth hormone releasing hormone using an injectable myogenic vector. Nat. Biotechnol. 15:1285-1289.

Draghia-Akli, R., P. B. Malone, L. A. Hill, K. M. Ellis, R. J. Schwartz, and J. L. Nordstrom. 2002c. Enhanced animal growth via ligand-regulated GHRH myogenic-injectable vectors. FASEB J. 16:426-428.

Fewell, J. G., F. MacLaughlin, V. Mehta, M. Gondo, F. Nicol, E. Wilson, and L. C. Smith. 2001. Gene therapy for the treatment of hemophilia B using PINC-formulated plasmid delivered to muscle with electroporation. Mol. Ther. 3:574-583.

Frederickson, R. M., B. J. Carter, and A. M. Pilaro. 2003. Nonclinical Toxicology in Support of Licensure of Gene Therapies. Mol. Ther. 8:8-10.

Fryer, A. D. and D. B. Jacoby. 1993. Effect of inflammatory cell mediators on M2 muscarinic receptors in the lungs. Life Sci. 52:529-536.

Gayle, R. B., III, P. S. Vermersch, and G. N. Bennett. 1986. Construction and characterization of pBR322-derived plasmids with deletions of the RNA I region. Gene 41:281-288.

Gehl, J., T. Skovsgaard, and L. M. Mir. 1998. Enhancement of cytotoxicity by electropermeabilization: an improved method for screening drugs. Anticancer Drugs 9:319-325.

Gehl, J., T. H. Sorensen, K. Nielsen, P. Raskmark, S. L. Nielsen, T. Skovsgaard, and L. M. Mir. 1999. In vivo electroporation of skeletal muscle: threshold, efficacy and relation to electric field distribution. Biochim. Biophys. Acta 1428:233-240.

German, M., S. Ashcroft, K. Docherty, H. Edlund, T. Edlund, S. Goodison, H. Imura, G. Kennedy, O. Madsen, D. Melloul, and 1995. The insulin gene promoter. A simplified nomenclature. Diabetes 44:1002-1004.

Harley, C. B. and R. P. Reynolds. 1987. Analysis of *E. coli* promoter sequences. Nucleic Acids Res. 15:2343-2361.

Heller, R., M. J. Jaroszeski, L. F. Glass, J. L. Messina, D. P. Rapaport, R. C. DeConti, N. A. Fenske, R. A. Gilbert, L. M. Mir, and D. S. Reintgen. 1996. Phase I/II trial for the treatment of cutaneous and subcutaneous tumors using electrochemotherapy. Cancer 77:964-971.

Horlick, R. A. and P. A. Benfield. 1989. The upstream muscle-specific enhancer of the rat muscle creatine kinase gene is composed of multiple elements. Mol. Cell Biol. 9:2396-2413.

Inouye, C., P. Remondelli, M. Karin, and S. Elledge. 1994. Isolation of a cDNA encoding a metal response element binding protein using a novel expression cloning procedure: the one hybrid system. DNA Cell Biol. 13:731-742.

Inouye, S., A. Nakazawa, and T. Nakazawa. 1985. Determination of the transcription initiation site and identification of the protein product of the regulatory gene xylR for xyl operons on the TOL plasmid. J. Bacteriol. 163:863-869.

Jaynes, J. B., J. E. Johnson, J. N. Buskin, C. L. Gartside, and S. D. Hauschka. 1988. The muscle creatine kinase gene is regulated by multiple upstream elements, including a muscle-specific enhancer. Mol. Cell Biol. 8:62-70.

Jenkins, G. J., H. S. Suzen, R. A. Sueiro, and J. M. Parry. 1999. The restriction site mutation assay: a review of the methodology development and the current status of the technique. Mutagenesis 14:439-448.

Kammerer, W., U. Deuschle, R. Gentz, and H. Bujard. 1986. Functional dissection of *Escherichia coli* promoters: information in the transcribed region is involved in late steps of the overall process. EMBO J. 5:2995-3000.

Kawamoto, T., K. Makino, H. Niwa, H. Sugiyama, S. Kimura, M. Amemura, A. Nakata, and T. Kakunaga. 1988. Identification of the human beta-actin enhancer and its binding factor. Mol. Cell Biol. 8:267-272.

Kawamoto, T., K. Makino, S. Orita, A. Nakata, and T. Kakunaga. 1989. DNA bending and binding factors of the human beta-actin promoter. Nucleic Acids Res. 17:523-537.

Klamut, H. J., L. O. Bosnoyan-Collins, R. G. Worton, P. N. Ray, and H. L. Davis. 1996. Identification of a transcriptional enhancer within muscle intron I of the human dystrophin gene. Hum. Mol. Genet. 5:1599-1606.

Klamut, H. J., S. B. Gangopadhyay, R. G. Worton, and P. N. Ray. 1990. Molecular and functional analysis of the muscle-specific promoter region of the Duchenne muscular dystrophy gene. Mol. Cell Biol. 10:193-205.

Kraus, J., M. Woltje, N. Schonwetter, and V. Hollt. 1998. Alternative promoter usage and tissue specific expression of the mouse somatostatin receptor 2 gene. FEBS Lett. 428:165-170.

Lahijani, R., G. Hulley, G. Soriano, N. A. Horn, and M. Marquet. 1996. High-yield production of pBR322-derived plasmids intended for human gene therapy by employing a temperature-controllable point mutation. Hum. Gene Ther. % 20; 7: 1971-1980.

Lareyre, J. J., T. Z. Thomas, W. L. Zheng, S. Kasper, D. E. Ong, M. C. Orgebin-Crist, and R. J. Matusik. 1999. A 5-kilobase pair promoter fragment of the murine epididymal retinoic acid-binding protein gene drives the tissue-specific, cell-specific, and androgen-regulated expression of a foreign gene in the epididymis of transgenic mice. J. Biol. Chem. 274:8282-8290.

Larsen, P. R., J. W. Harney, and D. D. Moore. 1986. Sequences required for cell-type specific thyroid hormone regulation of rat growth hormone promoter activity. J. Biol. Chem. 261:14373-14376.

Ledwith, B. J., S. Manam, P. J. Troilo, A. B. Barnum, C. J. Pauley, T. G. Griffiths, L. B. Harper, C. M. Beare, W. J. Bagdon, and W. W. Nichols. 2000a. Plasmid DNA vaccines: investigation of integration into host cellular DNA following intramuscular injection in mice. Intervirology 43:258-272.

Ledwith, B. J., S. Manam, P. J. Troilo, A. B. Barnum, C. J. Pauley, T. G. Griffiths, L. B. Harper, H. B. Schock, H. Zhang, J. E. Faris, P. A. Way, C. M. Beare, W. J. Bagdon, and W. W. Nichols. 2000b. Plasmid DNA vaccines: assay for integration into host genomic DNA. Dev. Biol. (Basel) 104:33-43.:33-43.

Lee, S. H., W. Wang, S. Yajima, P. A. Jose, and M. M. Mouradian. 1997. Tissue-specific promoter usage in the D1A dopamine receptor gene in brain and kidney. DNA Cell Biol. 16:1267-1275.

Lesbordes, J. C., T. Bordet, G. Haase, L. Castelnau-Ptakhine, S. Rouhani, H. Gilgenkrantz, and A. Kahn. 2002. In vivo electrotransfer of the cardiotrophin-1 gene into skeletal muscle slows down progression of motor neuron degeneration in pmn mice. Hum. Mol. Genet. 11:1615-1625.

Levenson, V. V., E. D. Transue, and I. B. Roninson. 1998. Internal ribosomal entry site-containing retroviral vectors with green fluorescent protein and drug resistance markers. Hum. Gene Ther. 9:1233-1236.

Li, C., S. Ke, Q. P. Wu, W. Tansey, N. Hunter, L. M. Buchmiller, L. Milas, C. Charnsangavej, and S. Wallace. 2000. Tumor irradiation enhances the tumor-specific distribution of poly(L-glutamic acid)-conjugated paclitaxel and its antitumor efficacy. Clin. Cancer Res. 6:2829-2834.

Li, X., E. M. Eastman, R. J. Schwartz, and R. Draghia-Akli. 1999. Synthetic muscle promoters: activities exceeding naturally occurring regulatory sequences. Nat. Biotechnol. 17:241-245.

Lin, H., K. E. Yutzey, and S. F. Konieczny. 1991. Muscle-specific expression of the troponin I gene requires interactions between helix-loop-helix muscle regulatory factors and ubiquitous transcription factors. Mol. Cell Biol. 11:267-280.

Lin-Chao, S., W. T. Chen, and T. T. Wong. 1992. High copy number of the pUC plasmid results from a Rom/Rop-suppressible point mutation in RNA II. Mol. Microbiol. 6:3385-3393.

Liu, Y., H. Li, K. Tanaka, N. Tsumaki, and Y. Yamada. 2000. Identification of an enhancer sequence within the first intron required for cartilage-specific transcription of the alpha2(XI) collagen gene. J. Biol. Chem. 275:12712-12718.

Lucas, M. L., L. Heller, D. Coppola, and R. Heller. 2002. IL-12 plasmid delivery by in vivo electroporation for the successful treatment of established subcutaneous B16.F10 melanoma. Mol. Ther. 5:668-675.

Lucas, M. L., M. J. Jaroszeski, R. Gilbert, and R. Heller. 2001. In vivo electroporation using an exponentially enhanced pulse: a new waveform. DNA Cell Biol. 20:183-188.

Lyons, A. J. and H. D. Robertson. 2003. Detection of tRNA-like structure through RNase P cleavage of viral internal ribosome entry site RNAs near the AUG start triplet. J. Biol. Chem. 278:26844-26850.

Macejak, D. G. and P. Sarnow. 1991. Internal initiation of translation mediated by the 5' leader of a cellular mRNA. Nature 353:90-94.

Manam, S., B. J. Ledwith, A. B. Barnum, P. J. Troilo, C. J. Pauley, L. B. Harper, T. G. Griffiths, Z. Niu, L. Denisova, T. T. Follmer, S. J. Pacchione, Z. Wang, C. M. Beare, W. J. Bagdon, and W. W. Nichols. 2000. Plasmid DNA vaccines: tissue distribution and effects of DNA sequence, adjuvants and delivery method on integration into host DNA. Intervirology 43:273-281.

Manders, P. and R. Thomas. 2000. Immunology of DNA vaccines: CpG motifs and antigen presentation. Inflamm. Res. 49:199-205.

Martineau, Y., C. Le Bec, L. Monbrun, V. Allo, I. M. Chiu, O. Danos, H. Moine, H. Prats, and A. C. Prats. 2004. Internal ribosome entry site structural motifs conserved among mammalian fibroblast growth factor 1 alternatively spliced mRNAs. Mol. Cell Biol. 24:7622-7635.

Matsubara, H., Y. Gunji, T. Maeda, K. Tasaki, Y. Koide, T. Asano, T. Ochiai, S. Sakiyama, and M. Tagawa. 2001.

Electroporation-mediated transfer of cytokine genes into human esophageal tumors produces anti-tumor effects in mice. Anticancer Res. 21:2501-2503.

Matsuo, A., I. Tooyama, S. Isobe, Y. Oomura, I. Akiguchi, K. Hanai, J. Kimura, and H. Kimura. 1994. Immunohistochemical localization in the rat brain of an epitope corresponding to the fibroblast growth factor receptor-1. Neuroscience 60:49-66.

McCluskie, M. J., R. D. Weeratna, and H. L. Davis. 2000. The role of CpG in DNA vaccines. Springer Semin. Immunopathol. 22:125-132.

McNally, M. A., J. S. Lebkowski, T. B. Okarma, and L. B. Lerch. 1988. Optimizing electroporation parameters for a variety of human hematopoietic cell lines. Biotechniques 6:882-886.

Miklavcic, D., K. Beravs, D. Semrov, M. Cemazar, F. Demsar, and G. Sersa. 1998. The importance of electric field distribution for effective in vivo electroporation of tissues. Biophys. J 74:2152-2158.

Mumper, R. J., J. Wang, S. L. Klakamp, H. Nitta, K. Anwer, F. Tagliaferri, and A. P. Rolland. 1998. Protective interactive noncondensing (PINC) polymers for enhanced plasmid distribution and expression in rat skeletal muscle. J. Control Release 52:191-203.

Muramatsu, T., S. Arakawa, K. Fukazawa, Y. Fujiwara, T. Yoshida, R. Sasaki, S. Masuda, and H. M. Park. 2001. In vivo gene electroporation in skeletal muscle with special reference to the duration of gene expression. Int. J. Mol. Med. 7:3742.

Nairn, R. S., G. M. Adair, T. Porter, S. L. Pennington, D. G. Smith, J. H. Wilson, and M. M. Seidman. 1993. Targeting vector configuration and method of gene transfer influence targeted correction of the APRT gene in Chinese hamster ovary cells. Somat. Cell Mol. Genet. 19:363-375.

Narum, D. L., S. Kumar, W. O. Rogers, S. R. Fuhrmann, H. Liang, M. Oakley, A. Taye, B. K. Sim, and S. L. Hoffman. 2001. Codon optimization of gene fragments encoding *Plasmodium falciparum* merzoite proteins enhances DNA vaccine protein expression and immunogenicity in mice. Infect. Immun. 69:7250-7253.

Neumann, E., M. Schaefer-Ridder, Y. Wang, and P. H. Hofschneider. 1982. Gene transfer into mouse lyoma cells by electroporation in high electric fields. EMBO J. 1:841-845.

Nomoto, S., Y. Tatematsu, T. Takahashi, and H. Osada. 1999. Cloning and characterization of the alternative promoter regions of the human LIMK2 gene responsible for alternative transcripts with tissue-specific expression. Gene 236:259-271.

Ohlsson, H., S. Thor, and T. Edlund. 1991. Novel insulin promoter- and enhancer-binding proteins that discriminate between pancreatic alpha- and beta-cells. Mol. Endocrinol. 5:897-904.

Otani, Y., Y. Tabata, and Y. Ikada. 1996. Rapidly curable biological glue composed of gelatin and poly(L-glutamic acid). Biomaterials 17:1387-1391.

Otani, Y., Y. Tabata, and Y. Ikada. 1998. Hemostatic capability of rapidly curable glues from gelatin, poly(L-glutamic acid), and carbodiimide. Biomaterials 19:2091-2098.

Pech, M., C. D. Rao, K. C. Robbins, and S. A. Aaronson. 1989. Functional identification of regulatory elements within the promoter region of platelet-derived growth factor 2. Mol. Cell Biol. 9:396-405.

Pelletier, J. and N. Sonenberg. 1988. Internal initiation of translation of eukaryotic mRNA directed by a sequence derived from poliovirus RNA. Nature 334:320-325.

Pinkert, C. A., D. M. Omitz, R. L. Brinster, and R. D. Palmiter. 1987. An albumin enhancer located 10 kb upstream functions along with its promoter to direct efficient, liver-specific expression in transgenic mice. Genes Dev. 1:268-276.

Potter, H., L. Weir, and P. Leder. 1984. Enhancer-dependent expression of human kappa immunoglobulin genes introduced into mouse pre-B lymphocytes by electroporation. Proc. Natl. Acad. Sci. U.S. A 81:7161-7165.

Ross, W., S. E. Aiyar, J. Salomon, and R. L. Gourse. 1998. *Escherichia coli* promoters with UP elements of different strengths: modular structure of bacterial promoters. J. Bacteriol. 180:5375-5383.

Ryu, D. D. and D. H. Nam. 2000. Recent progress in biomolecular engineering. Biotechnol. Prog. 16:2-16.

Scheule, R. K. 2000. The role of CpG motifs in immunostimulation and gene therapy. Adv. Drug Deliv. Rev. 44:119-134.

Shi, H., P. S. Yan, C. M. Chen, F. Rahmatpanah, C. Lofton-Day, C. W. Caldwell, and T. H. Huang. 2002. Expressed CpG island sequence tag microarray for dual screening of DNA hypermethylation and gene silencing in cancer cells. Cancer Res. 62:3214-3220.

Shiraishi, M., A. Sekiguchi, M. J. Terry, A. J. Oates, Y. Miyamoto, Y. H. Chuu, M. Munakata, and T. Sekiya. 2002. A comprehensive catalog of CpG islands methylated in human lung adenocarcinomas for the identification of tumor suppressor genes. Oncogene 21:3804-3813.

Skroch, P., C. Buchman, and M. Karin. 1993. Regulation of human and yeast metallothionein gene transcription by heavy metal ions. Prog. Clin. Biol. Res. 380:113-28.:113-128.

Smith, L. C. and J. L. Nordstrom. 2000. Advances in plasmid gene delivery and expression in skeletal muscle. Curr. Opin. Mol. Ther. 2:150-154.

Soubrier, F., B. Cameron, B. Manse, S. Somarriba, C. Dubertret, G. Jaslin, G. Jung, C. L. Caer, D. Dang, J. M. Mouvault, D. Scherman, J. F. Mayaux, and J. Crouzet. 1999. pCOR: a new design of plasmid vectors for nonviral gene therapy. Gene Ther. 6:1482-1488.

Stanford, W. L., J. B. Cohn, and S. P. Cordes. 2001. Gene-trap mutagenesis: past, present and beyond. Nat. Rev. Genet. 2:756-768.

Terada, Y., H. Tanaka, T. Okado, S. Inoshita, M. Kuwahara, T. Akiba, S. Sasaki, and F. Marumo. 2001. Efficient and ligand-dependent regulated erythropoietin production by naked dna injection and in vivo electroporation. Am. J. Kidney Dis. 38:S50-S53.

Tollefsen, S., M. Vordermeier, I. Olsen, A. K. Storset, L. J. Reitan, D. Clifford, D. B. Lowrie, H. G. Wiker, K. Huygen, G. Hewinson, I. Mathiesen, and T. E. Tjelle. 2003. DNA injection in combination with electroporation: a novel method for vaccination of farmed ruminants. Scand. J. Immunol. 57:229-238.

Tone, C. M., D. M. Cardoza, R. H. Carpenter, and R. Draghia-Akli. 2004. Long-term effects of plasmid-mediated growth hormone releasing hormone in dogs. Cancer Gene Ther. 11:389-396.

Toneguzzo, F., A. Keating, S. Glynn, and K. McDonald. 1988. Electric field-mediated gene transfer: characterization of DNA transfer and patterns of integration in lymphoid cells. Nucleic Acids Res. 16:5515-5532.

Tripathy, S. K., E. C. Svensson, H. B. Black, E. Goldwasser, M. Margalith, Hobart, P M, and J. M. Leiden. 1996. Long-term expression of erythropoietin in the systemic circulation of mice after intramuscular injection of a plasmid DNA vector. Proc. Natl. Acad. Sci. USA 93:10876-10880.

Tronche, F., A. Rollier, I. Bach, M. C. Weiss, and M. Yaniv. 1989. The rat albumin promoter: cooperation with upstream elements is required when binding of APF/HNF1 to the proximal element is partially impaired by mutation or bacterial methylation. Mol. Cell Biol. 9:4759-4766.

Tronche, F., A. Rollier, P. Herbomel, I. Bach, S. Cereghini, M. Weiss, and M. Yaniv. 1990. Anatomy of the rat albumin promoter. Mol. Biol. Med. 7:173-185.

Trudel, M. and F. Costantini. 1987. A 3' enhancer contributes to the stage-specific expression of the human beta-globin gene. Genes Dev. 1:954-961.

Tsumaki, N., T. Kimura, K. Tanaka, J. H. Kimura, T. Ochi, and Y. Yamada. 1998. Modular arrangement of cartilage- and neural tissue-specific cis-elements in the mouse alpha2 (XI) collagen promoter. J. Biol. Chem. 273:22861-22864.

Tsurumi, Y., S. Takeshita, D. Chen, M. Kearney, S. T. Rossow, J. Passeri, J. R. Horowitz, J. F. Symes, and J. M. Isner. 1996. Direct intramuscular gene transfer of naked DNA encoding vascular endothelial growth factor augments collateral development and tissue perfusion [see comments]. Circulation 94:3281-3290.

Tur-Kaspa, R., L. Teicher, B. J. Levine, A. I. Skoultchi, and D. A. Shafritz. 1986. Use of electroporation to introduce biologically active foreign genes into primary rat hepatocytes. Mol. Cell Biol. 6:716-718.

Vilquin, J. T., P. F. Kennel, M. Patumeau-Jouas, P. Chapdelaine, N. Boissel, P. Delaere, J. P. Tremblay, D. Scherman, M. Y. Fiszman, and K. Schwartz. 2001. Electrotransfer of naked DNA in the skeletal muscles of animal models of muscular dystrophies. Gene Ther. 8:1097-1107.

Wolff, J. A., R. W. Malone, P. Williams, W. Chong, G. Acsadi, A. Jani, Felgner, and P L. 1990. Direct gene transfer into mouse muscle in vivo. Science 247:1465-1468.

Wu, H. K., J. A. Squire, Q. Song, and R. Weksberg. 1997. Promoter-dependent tissue-specific expressive nature of imprinting gene, insulin-like growth factor II, in human tissues. Biochem. Biophys. Res. Commun. 233:221-226.

Xie, T. D. and T. Y. Tsong. 1993. Study of mechanisms of electric field-induced DNA transfection. V. Effects of DNA topology on surface binding, cell uptake, expression, and integration into host chromosomes of DNA in the mammalian cell. Biophys. J. 65:1684-1689.

Yasui, A., K. Oda, H. Usunomiya, K. Kakudo, T. Suzuki, T. Yoshida, H. M. Park, K. Fukazawa, and T. Muramatsu. 2001. Elevated gastrin secretion by in vivo gene electroporation in skeletal muscle. Int. J Mol. Med. 8:489-494.

Yin, D. and J. G. Tang. 2001. Gene therapy for streptozotocin-induced diabetic mice by electroporational transfer of naked human insulin precursor DNA into skeletal muscle in vivo. FEBS Lett. 495:16-20.

Yorifuji, T. and H. Mikawa. 1990. Co-transfer of restriction endonucleases and plasmid DNA into mammalian cells by electroporation: effects on stable transformation. Mutat. Res. 243:121-126.

Yutzey, K. E. and S. F. Konieczny. 1992. Different E-box regulatory sequences are functionally distinct when placed within the context of the troponin I enhancer. Nucleic Acids Res. 20:5105-5113.

Zhao-Emonet, J. C., O. Boyer, J. L. Cohen, and D. Klatzmann. 1998. Deletional and mutational analyses of the human CD4 gene promoter: characterization of a minimal tissue-specific promoter. Biochim. Biophys. Acta 1442: 109-119.

Zheng, Q. and D. J. Kyle. 1996. Computational screening of combinatorial libraries. Bioorg. Med. Chem. 4:631-638.

Zuker, M. 2003. Mfold web server for nucleic acid folding and hybridization prediction. Nucleic Acids Res. 31:3406-3415.

The Eukaryotic Promoter Data Base EPDB

---

What is claimed is:

1. A synthetic mammalian expression plasmid comprising:
   (a) a synthetic or eukaryotic promoter;
   (b) codon-optimized, eukaryotic therapeutic gene sequence;
   (c) a poly adenylation signal;
   (d) a selectable marker gene sequence operably linked to a selectable marker gene promoter;
   (e) a ribosomal binding site; and
   (f) an origin of replication comprising a sequence that is SEQ ID No.: 40;
   wherein elements (a)-(c), above, are operatively linked and located in a first operatively-linked arrangement; and elements (d)-(f), above, are operatively linked and located in a second operatively-linked arrangement.

2. An isolated nucleic acid having an origin of replication comprising SEQ ID No.: 40.

* * * * *

SEQUENCE LISTING

```
<160> NUMBER OF SEQ ID NOS: 64

<210> SEQ ID NO 1
<211> LENGTH: 3534
<212> TYPE: DNA
<213> ORGANISM: Artificial Sequence
<220> FEATURE:
<223> OTHER INFORMATION: Plasmid Vector having an analog HV-GHRH
      sequence.

<400> SEQUENCE: 1
ccaccgcggt ggcggccgtc cgccctcggc accatcctca cgacacccaa atatggcgac      60
gggtgaggaa tggtggggag ttatttttag agcggtgagg aaggtgggca ggcagcaggt     120
gttggcgctc taaaataac tcccgggagt tatttttaga gcggaggaat ggtggacacc      180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag ctctagaact agtggatccc     360
aaggcccaac tccccgaacc actcagggtc ctgtggacag ctcacctagc tgccatggtg     420
ctctgggtgt tcttctttgt gatcctcacc ctcagcaaca gctcccactg ctcccacct     480 cccccttga ccctcaggat gcggcggcac gtagatgcca tcttcaccaa cagctaccgg     540
aaggtgctgg cccagctgtc cgcccgcaag ctgctccagg acatcctgaa caggcagcag    600
```

-continued

```
ggagagagga accaagagca aggagcataa tgactgcagg aattcgatat caagcttatc    660
ggggtggcat ccctgtgacc cctccccagt gcctctcctg gccctggaag ttgccactcc    720
agtgcccacc agccttgtcc taataaaatt aagttgcatc attttgtctg actaggtgtc    780
cttctataat attatggggt ggaggggggt ggtatggagc aaggggcaag ttgggaagac    840
aacctgtagg gcctgcgggg tctattggga accaagctgg agtgcagtgg cacaatcttg    900
gctcactgca atctccgcct cctggttcaa gcgattctc ctgcctcagc ctcccgagtt     960
gttgggattc caggcatgca tgaccaggct cagctaattt ttgtttttt ggtagagacg    1020
gggtttcacc atattggcca ggctggtctc caactcctaa tctcaggtga tctacccacc   1080
ttggcctccc aaattgctgg gattacaggc gtgaaccact gctcccttcc ctgtccttct   1140
gattttaaaa taactatacc agcaggagga cgtccagaca cagcataggc tacctggcca   1200
tgcccaaccg gtgggacatt tgagttgctt gcttggcact gtcctctcat gcgttgggtc   1260
cactcagtag atgcctgttg aattcgatac cgtcgacctc gagggggggc ccggtaccag   1320
cttttgttcc ctttagtgag ggttaatttc gagcttggcg taatcatggt catagctgtt   1380
tcctgtgtga aattgttatc cgctcacaat tccacacaac atacgagccg aagcataaa    1440
gtgtaaagcc tggggtgcct aatgagtgag ctaactcaca ttaattgcgt tgcgctcact   1500
gcccgctttc cagtcgggaa acctgtcgtg ccagctgcat taatgaatcg ccaacgcgc    1560
ggggagaggc ggtttgcgta ttgggcgctc ttccgcttcc tcgctcactg actcgctgcg   1620
ctcggtcgtt cggctgcggc gagcggtatc agctcactca aaggcggtaa tacggttatc   1680
cacagaatca ggggataacg caggaaagaa catgtgagca aaaggccagc aaaaggccag   1740
gaaccgtaaa aaggccgcgt tgctggcgtt tttccatagg ctccgccccc ctgacgagca   1800
tcacaaaaat cgacgctcaa gtcagaggtg gcgaaacccg acaggactat aaagatacca   1860
ggcgtttccc cctggaagct ccctcgtgcg ctctcctgtt ccgaccctgc cgcttaccgg   1920
atacctgtcc gcctttctcc cttcgggaag cgtggcgctt tctcatagct cacgctgtag   1980
gtatctcagt tcggtgtagg tcgttcgctc caagctgggc tgtgtgcacg aaccccccgt   2040
tcagcccgac cgctgcgcct tatccggtaa ctatcgtctt gagtccaacc cggtaagaca   2100
cgacttatcg ccactggcag cagccactgg taacaggatt agcagagcga ggtatgtagg   2160
cggtgctaca gagttcttga agtggtggcc taactacggc tacactagaa gaacagtatt   2220
tggtatctgc gctctgctga agccagttac cttcggaaaa agagttggta gctcttgatc   2280
cggcaaacaa accaccgctg gtagcggtgg tttttttgtt tgcaagcagc agattacgcg   2340
cagaaaaaaa ggatctcaag aagatccttt gatcttttct acggggtctg acgctcagaa   2400
gaactcgtca agaaggcgat agaaggcgat gcgctgcgaa tcgggagcgg cgataccgta   2460
aagcacgagg aagcggtcag cccattcgcc gccaagctct tcagcaatat cacgggtagc   2520
caacgctatg tcctgatagc ggtccgccac acccagccgg ccacagtcga tgaatccaga   2580
aaagcggcca ttttccacca tgatattcgg caagcaggca tcgccatggg tcacgacgag   2640
atcctcgccg tcgggcatgc gcgccttgag cctggcgaac agttcggctg cgcgagccc    2700
ctgatgctct tcgtccagat catcctgatc gacaagaccg gcttccatcc gagtacgtgc   2760
tcgctcgatg cgatgtttcg cttggtggtc gaatgggcag gtagccggat caagcgtatg   2820
cagccgccgc attgcatcag ccatgatgga ctttctcg gcaggagcaa ggtgagatga    2880
caggagatct tgccccggca cttcgcccaa tagcagccag tccttcccg cttcagtgac    2940
aacgtcgagc acagctgcgc aaggaacgcc cgtcgtggcc agccacgata gccgcgctgc   3000
```

| | |
|---|---|
| ctcgtcctgc agttcattca gggcaccgga caggtcggtc ttgacaaaaa gaaccgggcg | 3060 |
| cccctgcgct gacagccgga acacggcggc atcagagcag ccgattgtct gttgtgccca | 3120 |
| gtcatagccg aatagcctct ccacccaagc ggccggagaa cctgcgtgca atccatcttg | 3180 |
| ttcaatcatg cgaaacgatc ctcatcctgt ctcttgatca gatcttgatc ccctgcgcca | 3240 |
| tcagatcctt ggcggcaaga aagccatcca gtttactttg cagggcttcc caaccttacc | 3300 |
| agagggcgcc ccagctggca attccggttc gcttgctgtc cataaaaccg cccagtctag | 3360 |
| caactgttgg gaagggcgat cggtgcgggc ctcttcgcta ttacgccagc tggcgaaagg | 3420 |
| gggatgtgct gcaaggcgat taagttgggt aacgccaggg ttttcccagt cacgacgttg | 3480 |
| taaaacgacg gccagtgaat tgtaatacga ctcactatag gcgaattgg agct | 3534 |

<210> SEQ ID NO 2
<211> LENGTH: 2725
<212> TYPE: DNA
<213> ORGANISM: Artificial Sequence
<220> FEATURE:
<223> OTHER INFORMATION: Codon optimized HV-GHRH with nat Kan expression
      plasmid pAV0201

<400> SEQUENCE: 2

| | |
|---|---|
| ccaccgcggt ggcggccgtc cgccctcggc accatcctca cgacacccaa atatggcgac | 60 |
| gggtgaggaa tggtggggag ttattttag agcggtgagg aaggtgggca ggcagcaggt | 120 |
| gttggcgctc taaaataac tcccgggagt tattttaga gcggaggaat ggtggacacc | 180 |
| caaatatggc gacggttcct caccgtcgc catatttggg tgtccgccct cggccggggc | 240 |
| cgcattcctg ggggccgggc ggtgctcccg ccgcctcga taaaggctc cggggccggc | 300 |
| ggcggcccac gagctacccg gaggagcggg aggcgccaag cggatcccaa gcccaactc | 360 |
| cccgaaccac tcagggtcct gtggacagct cacctagctg ccatggtgct ctgggtgttc | 420 |
| ttctttgtga tcctcaccct cagcaacagc tcccactgct ccccacctcc ccctttgacc | 480 |
| ctcaggatgc ggcggcacgt agatgccatc ttcaccaaca gctaccggaa ggtgctggcc | 540 |
| cagctgtccg cccgcaagct gctccaggac atcctgaaca ggcagcaggg agagaggaac | 600 |
| caagagcaag gagcataatg acatcaagct tatcggggtg catccctgt gacccctccc | 660 |
| cagtgcctct cctggccctg gaagttgcca ctccagtgcc accagccttt gtcctaataa | 720 |
| aattaagttg catcatttg tctgactagg tgtccttcta taatattatg ggtggaggg | 780 |
| gggtggtatg gagcaagggg caagttggga agacaacctg tagggctcga gggggggccc | 840 |
| ggtaccagct tttgttccct ttagtgaggg ttaatttcga gcttggtctt ccgcttcctc | 900 |
| gctcactgac tcgctgcgct cggtcgttcg gctgcggcga gcggtatcag ctcactcaaa | 960 |
| ggcggtaata cggttatcca cagaatcagg ggataacgca ggaaagaaca tgtgagcaaa | 1020 |
| aggccagcaa aaggccagga accgtaaaaa ggccgcgttg ctggcgtttt tccataggct | 1080 |
| ccgcccccct gacgagcatc acaaaaatcg acgctcaagt cagaggtggc gaaacccgac | 1140 |
| aggactataa agataccagg cgtttcccc tggaagctcc ctcgtgcgct ctcctgttcc | 1200 |
| gaccctgccg cttaccggat acctgtccgc ctttctccct tcgggaagcg tggcgctttc | 1260 |
| tcatagctca cgctgtaggt atctcagttc ggtgtaggtc gttcgctcca agctgggctg | 1320 |
| tgtgcacgaa ccccccgttc agcccgaccg ctgcgcctta ccggtaact atcgtcttga | 1380 |
| gtccaacccg gtaagacacg acttatcgcc actggcagca gccactggta acaggattag | 1440 |
| cagagcgagg tatgtaggcg gtgctacaga gttcttgaag tggtggccta actacggcta | 1500 |

```
cactagaaga acagtatttg gtatctgcgc tctgctgaag ccagttacct tcggaaaaag   1560
agttggtagc tcttgatccg gcaaacaaac caccgctggt agcggtggtt ttttttgttta  1620 caagcagcag attacgcgca gaaaaaaagg atctcaagaa gatcctttga tctttttctac  1680 ggggtctgac gctcagctag cgctcagaag aactcgtcaa gaaggcgata gaaggcgatg   1740
cgctgcgaat cgggagcggc gataccgtaa agcacgagga agcggtcagc ccattcgccg   1800
ccaagctctt cagcaatatc acgggtagcc aacgctatgt cctgatagcg gtccgccaca   1860
cccagccggc cacagtcgat gaatccagaa aagcggccat tttccaccat gatattcggc   1920
aagcaggcat cgccatgagt cacgacgaga tcctcgccgt cgggcatgcg cgccttgagc   1980
ctggcgaaca gttcggctgg cgcgagcccc tgatgctctt cgtccagatc atcctgatcg   2040
acaagaccgg cttccatccg agtacgtgct cgctcgatgc gatgtttcgc ttggtggtcg   2100
aatgggcagg tagccggatc aagcgtatgc agccgccgca ttgcatcagc catgatggat   2160
actttctcgg caggagcaag gtgagatgac aggagatcct gccccggcac ttcgcccaat   2220
agcagccagt cccttcccgc ttcagtgaca acgtcgagca cagctgcgca aggaacgccc   2280
gtcgtggcca gccacgatag ccgcgctgcc tcgtcctgca gttcattcag ggcaccggac   2340
aggtcggtct tgacaaaaag aaccgggcgc ccctgcgctg acagccggaa cacggcggca   2400
tcagagcagc cgattgtctg ttgtgcccag tcatagccga atagcctctc cacccaagcg   2460
gccggagaac ctgcgtgcaa tccatcttgt tcaatcatgc gaaacgatcc tcatcctgtc   2520
tcttgatcag atcttgatcc cctgcgccat cagatccttg gcggcaagaa agccatccag   2580
tttactttgc agggcttccc aaccttacca gagggcgccc cagctggcaa ttccggttcg   2640
cttgctgtcc ataaaaccgc ccagtctagc aactgttggg aagggcgatc gtgtaatacg   2700
actcactata gggcgaattg gagct                                          2725

<210> SEQ ID NO 3
<211> LENGTH: 323
<212> TYPE: DNA
<213> ORGANISM: Artificial Sequence
<220> FEATURE:
<223> OTHER INFORMATION: Nucleic Acid sequence of a eukaryotic promoter
      c5-12.

<400> SEQUENCE: 3
cggccgtccg ccctcggcac catcctcacg acacccaaat atggcgacgg gtgaggaatg    60
gtggggagtt attttagag cggtgaggaa ggtgggcagg cagcaggtgt tggcgctcta   120
aaaataactc ccgggagtta ttttagagc ggaggaatgg tggacaccca aatatggcga   180
cggttcctca cccgtcgcca tatttgggtg tccgccctcg gccggggccg cattcctggg   240
ggccgggcgg tgctcccgcc cgcctcgata aaaggctccg gggccggcgg cggcccacga   300
gctacccgga ggagcgggag gcg                                           323

<210> SEQ ID NO 4
<211> LENGTH: 219
<212> TYPE: DNA
<213> ORGANISM: Artificial Sequence
<220> FEATURE:
<223> OTHER INFORMATION: Nucleic acid sequence for GHRH (HV)

<400> SEQUENCE: 4
atggtgctct gggtgttctt ctttgtgatc ctcaccctca gcaacagctc ccactgctcc    60
ccacctcccc ctttgacccc caggatgcgg cggcacgtag atgccatctt caccaacagc   120
```

-continued

```
taccggaagg tgctggccca gctgtccgcc cgcaagctgc tccaggacat cctgaacagg      180
cagcagggag agaggaacca agagcaagga gcataatga                             219
```

<210> SEQ ID NO 5
<211> LENGTH: 618
<212> TYPE: DNA
<213> ORGANISM: Artificial Sequence
<220> FEATURE:
<223> OTHER INFORMATION: Nucleic acid sequence for 3' human GH poly A.

<400> SEQUENCE: 5

```
gggtggcatc cctgtgaccc ctccccagtg cctctcctgg ccctggaagt tgccactcca       60
gtgcccacca gccttgtcct aataaaatta agttgcatca ttttgtctga ctaggtgtcc      120
ttctataata ttatggggtg gaggggggtg gtatggagca aggggcaagt tgggaagaca      180
acctgtaggg cctgcggggt ctattgggaa ccaagctgga gtgcagtggc acaatcttgg      240
ctcactgcaa tctccgcctc ctgggttcaa gcgattctcc tgcctcagcc tcccgagttg      300
ttgggattcc aggcatgcat gaccaggctc agctaatttt tgtttttttg gtagagacgg      360
ggtttcacca tattggccag gctggtctcc aactcctaat ctcaggtgat ctacccacct      420
tggcctccca aattgctggg attacaggcg tgaaccactg ctcccttccc tgtccttctg      480
attttaaaat aactatacca gcaggaggac gtccagacac agcataggct acctggccat      540
gcccaaccgg tgggacattt gagttgcttg cttggcactg tcctctcatg cgttgggtcc      600
actcagtaga tgcctgtt                                                   618
```

<210> SEQ ID NO 6
<211> LENGTH: 219
<212> TYPE: DNA
<213> ORGANISM: Artificial Sequence
<220> FEATURE:
<223> OTHER INFORMATION: Porcine GHRH (wt).

<400> SEQUENCE: 6

```
atggtgctct gggtgttctt ctttgtgatc ctcaccctca gcaacagctc ccactgctcc       60
ccacctcccc ctttgaccct caggatgcgg cggtatgcag atgccatctt caccaacagc      120
taccggaagg tgctgggcca gctgtccgcc cgcaagctgc tccaggacat catgagcagg      180
cagcagggag agaggaacca agagcaagga gcataatga                             219
```

<210> SEQ ID NO 7
<211> LENGTH: 219
<212> TYPE: DNA
<213> ORGANISM: Artificial Sequence
<220> FEATURE:
<223> OTHER INFORMATION: Nucleotide sequence analog of procine GHRH
      (TI).

<400> SEQUENCE: 7

```
atggtgctct gggtgttctt ctttgtgatc ctcaccctca gcaacagctc ccactgctcc       60
ccacctcccc ctttgaccct caggatgcgg cggtatatcg atgccatctt caccaacagc      120
taccggaagg tgctggccca gctgtccgcc cgcaagctgc tccaggacat cctgaacagg      180
cagcagggag agaggaacca agagcaagga gcataatga                             219
```

<210> SEQ ID NO 8
<211> LENGTH: 219
<212> TYPE: DNA
<213> ORGANISM: Artificial Sequence

```
<220> FEATURE:
<223> OTHER INFORMATION: Nucleotide sequence analog of procine GHRH
      (TV).

<400> SEQUENCE: 8
atggtgctct gggtgttctt ctttgtgatc ctcaccctca gcaacagctc ccactgctcc      60
ccacctcccc ctttgaccct caggatgcgg cggtatgtag atgccatctt caccaacagc    120
taccggaagg tgctggccca gctgtccgcc cgcaagctgc tccaggacat cctgaacagg    180
cagcagggag agaggaacca agagcaagga gcataatga                            219

<210> SEQ ID NO 9
<211> LENGTH: 219
<212> TYPE: DNA
<213> ORGANISM: Artificial Sequence
<220> FEATURE:
<223> OTHER INFORMATION: Nucleotide sequence of analog of porcine GHRH
      (TA) 15/27/28.

<400> SEQUENCE: 9
atggtgctct gggtgttctt ctttgtgatc ctcaccctca gcaacagctc ccactgctcc      60
ccacctcccc ctttgaccct caggatgcgg cggtatgcag atgccatctt caccaacagc    120
taccggaagg tgctggccca gctgtccgcc cgcaagctgc tccaggacat cctgaacagg    180
cagcagggag agaggaacca agagcaagga gcataatga                            219

<210> SEQ ID NO 10
<211> LENGTH: 190
<212> TYPE: DNA
<213> ORGANISM: Artificial Sequence
<220> FEATURE:
<223> OTHER INFORMATION: Modified nucleotide sequence of 3' human GH in
      pAV0201.

<400> SEQUENCE: 10
gggtggcatc cctgtgaccc ctccccagtg cctctcctgg ccctggaagt tgccactcca      60
gtgcccacca gccttgtcct aataaaatta agttgcatca ttttgtctga ctaggtgtcc    120
ttctataata ttatggggtg agggggggtg gtatggagca aggggcaagt tgggaagaca    180
acctgtaggg                                                            190

<210> SEQ ID NO 11
<211> LENGTH: 782
<212> TYPE: DNA
<213> ORGANISM: Artificial Sequence
<220> FEATURE:
<223> OTHER INFORMATION: Nucleotide sequence for origin of replication
      in pAV0201.

<400> SEQUENCE: 11
tcttccgctt cctcgctcac tgactcgctg cgctcggtcg ttcggctgcg gcgagcggta      60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc ccctggaagc tccctcgtg    300 cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
```

```
aactatcgtc ttgagtccaa cccggtaaga cacgacttat cgccactggc agcagccact      540
ggtaacagga ttagcagagc gaggtatgta ggcggtgcta cagagttctt gaagtggtgg      600
cctaactacg gctacactag aagaacagta tttggtatct gcgctctgct gaagccagtt      660
accttcggaa aaagagttgg tagctcttga tccgacaaac aaaccaccgc tggtagcggt      720
ggtttttttg tttgcaagca gcagattacg cgcagaaaaa aaggatctca agaagatcct      780
tt                                                                    782
```

```
<210> SEQ ID NO 12
<211> LENGTH: 2725
<212> TYPE: DNA
<213> ORGANISM: Artificial Sequence
<220> FEATURE:
<223> OTHER INFORMATION: GHRH expression plasmid pAV0224.

<400> SEQUENCE: 12
```

```
ccaccgcggt ggcggccgtc cgccctcggc accatcctca cgacacccaa atatggcgac       60
gggtgaggaa tggtggggag ttattttag agcggtgagg aaggtgggca ggcagcaggt      120
gttggcgctc taaaaataac tcccgggagt tattttaga gcggaggaat ggtggacacc      180
caaatatggc gacggttcct cacccgtcgc catatttggg tgtccgccct cggccggggc      240
cgcattcctg ggggccgggc ggtgctcccg cccgcctcga taaaaggctc cggggccggc      300
ggcggcccac gagctacccg gaggagcggg aggcgccaag cggatcccaa ggcccaactc      360
cccgaaccac tcagggtcct gtggacagct cacctagctg ccatggtgct ctgggtgttc      420
ttctttgtga tcctcaccct cagcaacagc tcccactgct ccccacctcc ccctttgacc      480
ctcaggatgc ggcggcacgt agatgccatc ttcaccaaca gctaccggaa ggtgctggcc      540
cagctgtccg cccgcaagct gctccaggac atcctgaaca ggcagcaggg agagaggaac      600
caagagcaag gagcataatg acatcaagct tatcggggtg catccctgt gacccctccc      660 cagtgcctct cctggccctg gaagttgcca ctccagtgcc caccagcctt gtcctaataa      720
aattaagttg catcattttg tctgactagg tgtccttcta taatattatg gggtggaggg      780
gggtggtatg gagcaagggg caagttggga agacaacctg tagggctcga ggggggccc      840 ggtaccagct tttgttccct ttagtgaggg ttaatttcga gcttggtctt ccgcttcctc      900
gctcactgac tcgctgcgct cggtcgttcg gctgcggcga gcggtatcag ctcactcaaa      960
ggcggtaata cggttatcca cagaatcagg ggataacgca ggaaagaaca tgtgagcaaa     1020
aggccagcaa aaggccagga accgtaaaaa ggccgcgttg ctggcgtttt tccataggct     1080
ccgcccccct gacgagcatc acaaaaatcg acgctcaagt cagaggtggc gaaacccgac     1140
aggactataa agataccagg cgtttccccc tggaagctcc ctcgtgcgct ctcctgttcc     1200
gaccctgccg cttaccggat acctgtccgc ctttctccct cgggaagcg tggcgctttc     1260 tcatagctca cgctgtaggt atctcagttc ggtgtaggtc gttcgctcca agctgggctg     1320
tgtgcacgaa ccccccgttc agcccgaccg ctgcgcctta ccggtaact atcgtcttga     1380 gtccaacccg gtaagacacg acttatcgcc actggcagca gccactggta acaggattag     1440
cagagcgagg tatgtaggcg gtgctacaga gttcttgaag tggtggccta actacggcta     1500
cactagaaga acagtatttg gtatctgcgc tctgctgaag ccagttacct tcggaaaaag     1560
agttggtagc tcttgatccg gcaaacaaac caccgctggt agcggtggtt ttttgttta     1620 caagcagcag attacgcgca gaaaaaaagg atctcaagaa gatcctttga tcttttctac     1680
ggggtctgac gctcagctag cgctcagaag aactcgtcaa gaaggcgata gaaggcgatg     1740
```

-continued

```
cgctgcgaat cgggagcggc gataccgtaa agcacgagga agcggtcagc ccattcgccg    1800
ccaagctctt cagcaatatc acgggtagcc aacgctatgt cctgatagcg gtccgccaca    1860
cccagccggc cacagtcgat gaatccgaaa agcggccat  tttccaccat gatattcggc    1920
aagcaggcat cgccatgagt cacgacgaga tcctcgccgt cgggcatgcg cgccttgagc    1980
ctggcgaaca gttcggctgg cgcgagcccc tgatgctctt cgtccagatc atcctgatcg    2040
acaagaccgg cttccatccg agtacgtgct cgctcgatgc gatgtttcgc ttggtggtcg    2100
aatgggcagg tagccggatc aagcgtatgc agccgccgca ttgcatcagc catgatggat    2160
actttctcgg caggagcaag gtgagatgac aggagatcct gccccggcac ttcgcccaat    2220
agcagccagt cccttcccgc ttcagtgaca acgtcgagca gctgcgcaag gaacgcccc    2280 gtcgtggcca gccacgatag ccgcgctgcc tcgtcctgca gttcattcag ggcaccggac    2340
aggtcggtct tgacaaaaag aaccgggcgc ccctgcgctg acagccgaa  cacggcggca    2400 tcagagcagc cgattgtctg ttgtgcccag tcatagccga atagcctctc cacccaagcg    2460
gccggagaac ctgcgtgcaa tccatcttgt tcaatcatgc gaaacgatcc tcatcctgtc    2520
tcttgatcag atcttgatcc cctgcgccat cagatccttg gcggcaagaa agccatccag    2580
tttactttgc agggcttccc aaccttacca gagggcgccc cagctggcaa ttccggttcg    2640
cttgctgtcc ataaaaccgc ccagtctagc aactgttggg aagggcgatc gtgtaatacg    2700
actcactata gggcgaattg gagct                                           2725
```

<210> SEQ ID NO 13
<211> LENGTH: 2721
<212> TYPE: DNA
<213> ORGANISM: Artificial Sequence
<220> FEATURE:
<223> OTHER INFORMATION: pAV0225 GHRH expression plasmid.

<400> SEQUENCE: 13

```
ccaccgcggt ggcggccgtc cgccctcggc accatcctca cgacacccaa atatggcgac      60
gggtgaggaa tggtggggag ttattttag  agcggtgagg aaggtgggca ggcagcaggt     120
gttggcgctc taaaaataac tcccgggagt tattttaga  gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgcaag  cggatcccaa ggcccaactc     360
cccgaaccac tcagggtcct gtggacagct cacctagctg ccatggtgct ctgggtgttc     420
ttctttgtga tcctcaccct cagcaacagc tcccactgct ccccacctcc ccttttgacc     480
ctcaggatgc ggcggtatgc agatgccatc ttcaccaaca gctaccggaa ggtgctgggc     540
cagctgtccg cccgcaagct gctccaggac atcatgagca ggcagcaggg agagaggaac     600
caagagcaag gagcataatg aaagcttatc ggggtggcat ccctgtgacc cctccccagt     660
gcctctcctg gccctggaag ttgccactcc agtgccacc  agccttgtcc taataaaatt     720
aagttgcatc attttgtctg actaggtgtc cttctataat attatggggt ggaggggggt     780
ggtatggagc aaggggcaag ttgggaagac aacctgtagg gctcgagggg gggcccggta     840
ccagcttttg ttccctttag tgagggttaa tttcgagctt ggtcttccgc ttcctcgctc     900
actgactcgc tgcgctcggt cgttcggctg cggcgagcgg tatcagctca ctcaaaggcg     960
gtaatacggt tatccacaga atcaggggat aacgcaggaa agaacatgtg agcaaaaggc    1020
```

| | | | |
|---|---|---|---|
| cagcaaaagg | ccaggaaccg | taaaaaggcc | gcgttgctgg cgttttttcca taggctccgc | 1080 |
| cccccctgacg | agcatcacaa | aaatcgacgc | tcaagtcaga ggtggcgaaa cccgacagga | 1140 |
| ctataaagat | accaggcgtt | tccccctgga | agctccctcg tgcgctctcc tgttccgacc | 1200 |
| ctgccgctta | ccggatacct | gtccgccttt | ctcccttcgg aagcgtggc gctttctcat | 1260 |
| agctcacgct | gtaggtatct | cagttcggtg | taggtcgttc gctccaagct gggctgtgtg | 1320 |
| cacgaacccc | ccgttcagcc | cgaccgctgc | gccttatccg gtaactatcg tcttgagtcc | 1380 |
| aacccggtaa | gacacgactt | atcgccactg | gcagcagcca ctggtaacag gattagcaga | 1440 |
| gcgaggtatg | taggcggtgc | tacagagttc | ttgaagtggt ggcctaacta cggctacact | 1500 |
| agaagaacag | tatttggtat | ctgcgctctg | ctgaagccag ttaccttcgg aaaaagagtt | 1560 |
| ggtagctctt | gatccggcaa | acaaaccacc | gctggtagcg tggtttttt tgtttacaag | 1620 |
| cagcagatta | cgcgcagaaa | aaaggatct | caagaagatc ctttgatctt ttctacgggg | 1680 |
| tctgacgctc | agctagcgct | cagaagaact | cgtcaagaag gcgatagaag gcgatgcgct | 1740 |
| gcgaatcggg | agcggcgata | ccgtaaagca | cgaggaagcg gtcagcccat tcgccgccaa | 1800 |
| gctcttcagc | aatatcacgg | gtagccaacg | ctatgtcctg atagcggtcc gccacaccca | 1860 |
| gccggccaca | gtcgatgaat | ccagaaaagc | ggccattttc caccatgata ttcggcaagc | 1920 |
| aggcatcgcc | atgagtcacg | acgagatcct | cgccgtcggg catgcgcgcc ttgagcctgg | 1980 |
| cgaacagttc | ggctggcgcg | agcccctgat | gctcttcgtc cagatcatcc tgatcgacaa | 2040 |
| gaccggcttc | catccgagta | cgtgctcgct | cgatgcgatg tttcgcttgg tggtcgaatg | 2100 |
| ggcaggtagc | cggatcaagc | gtatgcagcc | gccgcattgc atcagccatg atggatactt | 2160 |
| tctcggcagg | agcaaggtga | gatgacagga | gatcctgccc cggcacttcg cccaatagca | 2220 |
| gccagtccct | tcccgcttca | gtgacaacgt | cgagcacagc tgcgcaagga acgcccgtcg | 2280 |
| tggccagcca | cgatagccgc | gctgcctcgt | cctgcagttc attcagggca ccggacaggt | 2340 |
| cggtcttgac | aaaaagaacc | gggcgcccct | gcgctgacag ccggaacacg gcggcatcag | 2400 |
| agcagccgat | tgtctgttgt | gcccagtcat | agccgaatag cctctccacc caagcggccg | 2460 |
| gagaacctgc | gtgcaatcca | tcttgttcaa | tcatgcgaaa cgatcctcat cctgtctctt | 2520 |
| gatcagatct | tgatccctg | cgccatcaga | tccttggcgg caagaaagcc atccagttta | 2580 |
| ctttgcaggg | cttcccaacc | ttaccagagg | gcgccccagc tggcaattcc ggttcgcttg | 2640 |
| ctgtccataa | aaccgcccag | tctagcaact | gttgggaagg gcgatcgtgt aatacgactc | 2700 |
| actatagggc | gaattggagc | t | | 2721 |

<210> SEQ ID NO 14
<211> LENGTH: 2558
<212> TYPE: DNA
<213> ORGANISM: Artificial Sequence
<220> FEATURE:
<223> OTHER INFORMATION: pAV0237 GHRH expression plasmid.

<400> SEQUENCE: 14

| | | | |
|---|---|---|---|
| ccaccgcggt | ggcggccgtc | cgccctcggc | accatcctca cgacacccaa atatggcgac | 60 |
| gggtgaggaa | tggtggggag | ttattttag | agcggtgagg aaggtgggca ggcagcaggt | 120 |
| gttggcgctc | taaaataac | tcccgggagt | tatttttaga gcgaggaat ggtggacacc | 180 |
| caaatatggc | gacggttcct | cacccgtcgc | catatttggg tgtccgccct cggccggggc | 240 |
| cgcattcctg | ggggccgggc | ggtgctcccg | cccgcctcga taaaaggctc cggggccggc | 300 |
| ggcggcccac | gagctacccg | gaggagcggg | aggcgccaag cggatcccaa ggcccaactc | 360 |

```
cccgaaccac tcagggtcct gtggacagct cacctagctg ccatggtgct ctgggtgttc      420
ttctttgtga tcctcaccct cagcaacagc tcccactgct ccccacctcc ccctttgacc      480
ctcaggatgc ggcggtatgc agatgccatc ttcaccaaca gctaccggaa ggtgctgggc      540
cagctgtccg cccgcaagct gctccaggac atcatgagca ggcagcaggg agagaggaac      600
caagagcaag gagcataatg aaagcttatc ggggtggcat ccctgtgacc cctccccagt      660
gcctctcctg gccctggaag ttgccactcc agtgcccacc agccttgtcc taataaaatt      720
aagttgcatc attttgtctg actaggtgtc cttctataat attatggggt ggaggggggt      780
ggtatggagc aaggggcaag ttgggaagac aacctgtagg gctcgagggg gggcccggta      840
ccatgtgagc aaaaggccag caaaaggcca ggaaccgtaa aaaggccgcg ttgctggcgt      900
ttttccatag gctccgcccc cctgacgagc atcacaaaaa tcgacgctca agtcagaggt      960
ggcgaaaccc gacaggacta taaagatacc aggcgtttcc ccctggaagc tccctcgtgc     1020
gctctcctgt tccgaccctg ccgcttaccg gatacctgtc cgcctttctc ccttcgggaa     1080
gcgtggcgct ttctcatagc tcacgctgta ggtatctcag ttcggtgtag tcgttcgct     1140 ccaagctggg ctgtgtgcac gaaccccccg ttcagcccga ccgctgcgcc ttatccggta     1200
actatcgtct tgagtccaac ccggtaagac acgacttatc gccactggca gcagccactg     1260
gtaacaggat tagcagagcg aggtatgtag gcggtgctac agagttcttg aagtggtggc     1320
ctaactacgg ctacactaga agaacagtat ttggtatctg cgctctgctg aagccagtta     1380
ccttcggaaa aagagttggt agctcttgat ccggcaaaca aaccaccgct ggtagcggtg     1440
gtttttttgt ttacaagcag cagattacgc gcagaaaaaa aggatctcaa gaagatcctt     1500
tgatcttttc tacggggtct gacgctcagc tagcgctcag aagaactcgt caagaaggcg     1560
atagaaggcg atgcgctgcg aatcgggagc ggcgataccg taaagcacga ggaagcggtc     1620
agcccattcg ccgccaagct cttcagcaat atcacgggta gccaacgcta tgtcctgata     1680
gcggtccgcc acacccagcc ggccacagtc gatgaatcca gaaaagcggc cattttccac     1740
catgatattc ggcaagcagg catcgccatg agtcacgacg agatcctcgc cgtcgggcat     1800
gcgcgccttg agcctggcga acagttcggc tggcgcgagc ccctgatgct cttcgtccag     1860
atcatcctga tcgacaagac cggcttccat ccgagtacgt gctcgctcga tgcgatgttt     1920
cgcttggtgg tcgaatgggc aggtagccgg atcaagcgta tgcagccgcc gcattgcatc     1980
agccatgatg gatactttct cggcaggagc aaggtgagat gacaggagat cctgccccgg     2040
cacttcgccc aatagcagcc agtcccttcc cgcttcagtg acaacgtcga gcacagctgc     2100
gcaaggaacg cccgtcgtgg ccagccacga tagccgcgct gcctcgtcct gcagttcatt     2160
cagggcaccg gacaggtcgg tcttgacaaa aagaaccggg cgccctgcg ctgacagccg     2220 gaacacggcg gcatcagagc agccgattgt ctgttgtgcc cagtcatagc cgaatagcct     2280
ctccacccaa gcggccggag aacctgcgtg caatccatct tgttcaatca tgcgaaacga     2340
tcctcatcct gtctcttgat cagatcttga tccctgcgc catcagatcc ttggcggcaa     2400
gaaagccatc cagtttactt tgcagggctt cccaacctta ccagagggcg ccccagctgg     2460
caattccggt tcgcttgctg tccataaaac cgcccagtct agcaactgtt gggaagggcg     2520
atcgtgtaat acgactcact atagggcgaa ttggagct                            2558

<210> SEQ ID NO 15
<211> LENGTH: 2505
<212> TYPE: DNA
```

<213> ORGANISM: Artificial Sequence
<220> FEATURE:
<223> OTHER INFORMATION: pAV0242 GHRH expression plasmid.

<400> SEQUENCE: 15

| | | | | | |
|---|---|---|---|---|---|
| ccaccgcggt | ggcggccgtc | cgccctcggc | accatcctca | cgacacccaa | atatggcgac | 60 |
| gggtgaggaa | tggtggggag | ttattttag | agcggtgagg | aaggtgggca | ggcagcaggt | 120 |
| gttggcgctc | taaaaataac | tcccgggagt | tattttaga | gcggaggaat | ggtggacacc | 180 |
| caaatatggc | gacggttcct | cacccgtcgc | catatttggg | tgtccgccct | cggccggggc | 240 |
| cgcattcctg | ggggccgggc | ggtgctcccg | cccgcctcga | taaaaggctc | cggggccggc | 300 |
| ggcggcccac | gagctacccg | gaggagcggg | aggcgccaag | cggatcccaa | ggcccaactc | 360 |
| cccgaaccac | tcagggtcct | gtggacagct | cacctagctg | ccatggtgct | ctgggtgttc | 420 |
| ttctttgtga | tcctcaccct | cagcaacagc | tcccactgct | ccccacctcc | ccctttgacc | 480 |
| ctcaggatgc | ggcggtatgc | agatgccatc | ttcaccaaca | gctaccggaa | ggtgctgggc | 540 |
| cagctgtccg | cccgcaagct | gctccaggac | atcatgagca | ggcagcaggg | agagaggaac | 600 |
| caagagcaag | gagcataatg | aaagcttatc | ggggtggcat | ccctgtgacc | cctccccagt | 660 |
| gcctctcctg | gccctggaag | ttgccactcc | agtgcccacc | agccttgtcc | taataaaatt | 720 |
| aagttgcatc | attttgtctg | actaggtgtc | cttctataat | attatggggt | ggaggggggt | 780 |
| ggtatggagc | aaggggcaag | ttgggaagac | aacctgtagg | gctcgagggg | gggcccggta | 840 |
| ccatgtgagc | aaaaggccag | caaaaggcca | ggaaccgtaa | aaaggccgcg | ttgctggcgt | 900 |
| ttttccatag | gctccgcccc | cctgacgagc | atcacaaaaa | tcgacgctca | agtcagaggt | 960 |
| ggcgaaaccc | gacaggacta | taaagatacc | aggcgtttcc | ccctggaagc | tccctcgtgc | 1020 |
| gctctcctgt | tccgaccctg | ccgcttaccg | gatacctgtc | cgcctttctc | ccttcgggaa | 1080 |
| gcgtggcgct | ttctcatagc | tcacgctgta | ggtatctcag | ttcggtgtag | gtcgttcgct | 1140 |
| ccaagctggg | ctgtgtgcac | gaaccccccg | ttcagcccga | ccgctgcgcc | ttatccggta | 1200 |
| actatcgtct | tgagtccaac | ccggtaagac | acgacttatc | gccactggca | gcagccactg | 1260 |
| gtaacaggat | tagcagagcg | aggtatgtag | gcggtgctac | agagttcttg | aagtggtggc | 1320 |
| ctaactacgg | ctacactaga | agaacagtat | ttggtatctg | cgctctgctg | aagccagtta | 1380 |
| ccttcggaaa | aagagttggt | agctcttgat | ccggcaaaca | aaccaccgct | ggtagcggtg | 1440 |
| gttttttgt | ttacaagcag | cagattacgc | gcagaaaaaa | aggatctcaa | gaagatcctt | 1500 |
| tgatcttttc | tacgggtct | gacgctcagc | tagcgctcag | aagaactcgt | caagaaggcg | 1560 |
| atagaaggcg | atgcgctgcg | aatcgggagc | ggcgataccg | taaagcacga | ggaagcggtc | 1620 |
| agcccattcg | ccgccaagct | cttcagcaat | atcacgggta | gccaacgcta | tgtcctgata | 1680 |
| gcggtccgcc | acacccagcc | ggccacagtc | gatgaatcca | gaaaagcggc | cattttccac | 1740 |
| catgatattc | ggcaagcagg | catcgccatg | agtcacgacg | agatcctcgc | cgtcgggcat | 1800 |
| gcgcgccttg | agcctggcga | acagttcggc | tggcgcgagc | cctgatgct | cttcgtccag | 1860 |
| atcatcctga | tcgacaagac | cggcttccat | ccgagtacgt | gctcgctcga | tgcgatgttt | 1920 |
| cgcttggtgg | tcgaatgggc | aggtagccgg | atcaagcgta | tgcagccgcc | gcattgcatc | 1980 |
| agccatgatg | gatactttct | cggcaggagc | aaggtgagat | gacaggagat | cctgccccgg | 2040 |
| cacttcgccc | aatagcagcc | agtcccttcc | cgcttcagtg | acaacgtcga | gcacagctgc | 2100 |
| gcaaggaacg | cccgtcgtgg | ccagccacga | tagccgcgct | gcctcgtcct | gcagttcatt | 2160 |
| cagggcaccg | gacaggtcgg | tcttgacaaa | aagaaccggg | cgcccctgcg | ctgacagccg | 2220 |

-continued

```
gaacacggcg gcatcagagc agccgattgt ctgttgtgcc cagtcatagc cgaatagcct    2280
ctccacccaa gcggccggag aacctgcgtg caatccatct tgttcaatca tgcgaaacga    2340
tcctcatcct gtctcttgat cagatcttga tccctgcgc catcagatcc ttggcggcaa     2400
gaaagccatc cagtttactt tgcagggctt cccaacctta ccagagggcg ccccagctgg    2460
caattccggt tcgcttgctg tccataaaac cgcccagtct gagct                    2505
```

<210> SEQ ID NO 16
<211> LENGTH: 144
<212> TYPE: DNA
<213> ORGANISM: Artificial Sequence
<220> FEATURE:
<223> OTHER INFORMATION: BglII/SacI Synthetic Fragment

<400> SEQUENCE: 16

```
agatcttgat ccctgcgcc atcagatcct tggcggcaag aaagccatcc agtttacttt     60
gcagggcttc ccaaccttac cagagggcgc cccagctggc aattccggtt cgcttgctgt   120
ccataaaacc gcccagtctg agct                                          144
```

<210> SEQ ID NO 17
<211> LENGTH: 40
<212> TYPE: PRT
<213> ORGANISM: Artificial Sequence
<220> FEATURE:
<223> OTHER INFORMATION: Amino acid sequence for porcine GHRH.

<400> SEQUENCE: 17

```
Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40
```

<210> SEQ ID NO 18
<211> LENGTH: 40
<212> TYPE: PRT
<213> ORGANISM: Artificial Sequence
<220> FEATURE:
<223> OTHER INFORMATION: HV-growth hormone releasing hormone ("GHRH")
       analog.

<400> SEQUENCE: 18

```
His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40
```

<210> SEQ ID NO 19
<211> LENGTH: 40
<212> TYPE: PRT
<213> ORGANISM: Artificial Sequence
<220> FEATURE:
<223> OTHER INFORMATION: TI-growth hormone releasing hormone ("GHRH")
       analog.

<400> SEQUENCE: 19

```
Tyr Ile Asp Ala Ile Phe Thr Asn Ser Tyr Arg Lys Val Leu Ala Gln
1               5                   10                  15
```

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 20
<211> LENGTH: 40
<212> TYPE: PRT
<213> ORGANISM: Artificial Sequence
<220> FEATURE:
<223> OTHER INFORMATION: TV-growth hormone releasing hormone ("GHRH")
      analog.

<400> SEQUENCE: 20

Tyr Val Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 21
<211> LENGTH: 40
<212> TYPE: PRT
<213> ORGANISM: Artificial Sequence
<220> FEATURE:
<223> OTHER INFORMATION: TA-growth hormone releasing hormone ("GHRH")
      analog.

<400> SEQUENCE: 21

Tyr Ala Asp Ala Ile Phe Thr Asn Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

Glu Arg Asn Gln Glu Gln Gly Ala
        35                  40

<210> SEQ ID NO 22
<211> LENGTH: 40
<212> TYPE: PRT
<213> ORGANISM: Artificial Sequence
<220> FEATURE:
<223> OTHER INFORMATION: Amino acid sequence for Bovine-GHRH.

<400> SEQUENCE: 22

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 23
<211> LENGTH: 40
<212> TYPE: PRT
<213> ORGANISM: Artificial Sequence
<220> FEATURE:
<223> OTHER INFORMATION: Amino acid sequence for Dog-GHRH.

<400> SEQUENCE: 23

Tyr Ala Asp Ala Ile Phe Thr Asn Ser Tyr Arg Lys Val Leu Gly Gln
1               5                   10                  15

```
Leu Ser Ala Arg Lys Leu Leu Gln Asp Ile Met Ser Arg Gln Gln Gly
            20                  25                  30

Glu Arg Asn Arg Glu Gln Gly Ala
        35                  40

<210> SEQ ID NO 24
<211> LENGTH: 40
<212> TYPE: PRT
<213> ORGANISM: Artificial Sequence
<220> FEATURE:
<223> OTHER INFORMATION: Amino acid sequence for Cat-GHRH.

<400> SEQUENCE: 24

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Arg Asn Gln Glu Gln Gly Ala
        35                  40

<210> SEQ ID NO 25
<211> LENGTH: 40
<212> TYPE: PRT
<213> ORGANISM: Artificial Sequence
<220> FEATURE:
<223> OTHER INFORMATION: Amino acid sequence for Ovine-GHRH.

<400> SEQUENCE: 25

Tyr Ala Asp Ala Ile Phe Thr Asn Ser Tyr Arg Lys Ile Leu Gly Gln
1               5                   10                  15

Leu Ser Ala Arg Lys Leu Leu Gln Asp Ile Met Asn Arg Gln Gln Gly
            20                  25                  30

Glu Arg Asn Gln Glu Gln Gly Ala
        35                  40

<210> SEQ ID NO 26
<211> LENGTH: 43
<212> TYPE: PRT
<213> ORGANISM: Artificial Sequence
<220> FEATURE:
<223> OTHER INFORMATION: Amino acid sequence for Chicken-GHRH.

<400> SEQUENCE: 26

His Ala Asp Gly Ile Phe Ser Lys Ala Tyr Arg Lys Leu Leu Gly Gln
1               5                   10                  15

Leu Ser Ala Arg Asn Tyr Leu His Ser Leu Met Ala Lys Arg Val Gly
            20                  25                  30

Ser Gly Leu Gly Asp Glu Ala Glu Pro Leu Ser
        35                  40

<210> SEQ ID NO 27
<211> LENGTH: 40
<212> TYPE: PRT
<213> ORGANISM: Artificial Sequence
<220> FEATURE:
<223> OTHER INFORMATION: Amino acid sequence for Horse GHRH.
<220> FEATURE:
<221> NAME/KEY: MISC_FEATURE
<222> LOCATION: (1)..(1)
<223> OTHER INFORMATION: "Xaa" can be any AA sequence
<220> FEATURE:
<221> NAME/KEY: MISC_FEATURE
<222> LOCATION: (30)..(40)
<223> OTHER INFORMATION: "Xaa" can be any AA sequence
```

```
<400> SEQUENCE: 27

Xaa Ala Asp Ala Ile Phe Thr Asn Asn Tyr Arg Lys Val Leu Gly Gln
1               5                   10                  15

Leu Ser Ala Arg Lys Ile Leu Gln Asp Ile Met Ser Arg Xaa Xaa Xaa
            20                  25                  30

Xaa Xaa Xaa Xaa Xaa Xaa Xaa Xaa
        35                  40

<210> SEQ ID NO 28
<211> LENGTH: 40
<212> TYPE: PRT
<213> ORGANISM: Artificial Sequence
<220> FEATURE:
<223> OTHER INFORMATION: Amino acid sequence for human (1-40)-GHRH.

<400> SEQUENCE: 28

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Human (1-44) growth hormone releasing hormone
      ("GHRH").

<400> SEQUENCE: 29

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 30
<211> LENGTH: 40
<212> TYPE: PRT
<213> ORGANISM: Artificial Sequence
<220> FEATURE:
<223> OTHER INFORMATION: GHRH (1-40)OH.
<220> FEATURE:
<221> NAME/KEY: MISC_FEATURE
<222> LOCATION: (1)..(1)
<223> OTHER INFORMATION: Xaa at position 1 may be tyrosine, or
      histidine.
<220> FEATURE:
<221> NAME/KEY: MISC_FEATURE
<222> LOCATION: (2)..(2)
<223> OTHER INFORMATION: Xaa at position 2 may be alanine, valine, or
      isoleucine.
<220> FEATURE:
<221> NAME/KEY: MISC_FEATURE
<222> LOCATION: (15)..(15)
<223> OTHER INFORMATION: Xaa at position 15 may be alanine, valine, or
      isoleucine.
<220> FEATURE:
<221> NAME/KEY: MISC_FEATURE
<222> LOCATION: (27)..(27)
<223> OTHER INFORMATION: Xaa at position 27 may be methionine, or
      leucine.
<220> FEATURE:
<221> NAME/KEY: MISC_FEATURE
```

```
<222> LOCATION: (28)..(28)
<223> OTHER INFORMATION: Xaa at position 28 may be serine or asparagine.
<220> FEATURE:
<221> NAME/KEY: MISC_FEATURE
<222> LOCATION: (34)..(34)
<223> OTHER INFORMATION: Xaa at position 34 may be arginine or serine.
<220> FEATURE:
<221> NAME/KEY: MISC_FEATURE
<222> LOCATION: (36)..(36)
<223> OTHER INFORMATION: Xaa at position 36 may be arginine or
      glutamine.
<220> FEATURE:
<221> NAME/KEY: MISC_FEATURE
<222> LOCATION: (38)..(38)
<223> OTHER INFORMATION: Xaa at position 38 may be arginine or
      glutamine.

<400> SEQUENCE: 30

Xaa Xaa Asp Ala Ile Phe Thr Asn Ser Tyr Arg Lys Val Leu Xaa Gln
1               5                   10                  15

Leu Ser Ala Arg Lys Leu Leu Gln Asp Ile Xaa Xaa Arg Gln Gln Gly
            20                  25                  30

Glu Xaa Asn Xaa Glu Xaa Gly Ala
        35                  40

<210> SEQ ID NO 31
<211> LENGTH: 2505
<212> TYPE: DNA
<213> ORGANISM: Artificial Sequence
<220> FEATURE:
<223> OTHER INFORMATION: RNA II Promoter Mutation 1 in pAV0242 G > T at
      1463.

<400> SEQUENCE: 31
ccaccgcggt ggcggccgtc cgccctcggc accatcctca cgacacccaa atatggcgac    60
gggtgaggaa tggtggggag ttattttag agcggtgagg aaggtgggca ggcagcaggt    120
gttggcgctc taaaataac tcccgggagt tattttaga gcggaggaat ggtggacacc     180
caaatatggc gacggttcct caccgtcgc catatttggg tgtccgccct cggccggggc    240
cgcattcctg gggccgggc ggtgctcccg ccgcctcga taaaggctc ggggccggc       300 ggcggcccac gagctacccg gaggagcggg aggcgccaag cggatcccaa ggcccaactc   360
cccgaaccac tcagggtcct gtggacagct cacctagctg ccatggtgct ctgggtgttc   420
ttctttgtga tcctcaccct cagcaacagc tcccactgct ccccacctcc ccctttgacc   480
ctcaggatgc ggcggtatgc agatgccatc ttcaccaaca gctaccggaa ggtgctgggc   540
cagctgtccg cccgcaagct gctccaggac atcatgagca ggcagcaggg agagaggaac   600
caagagcaag gagcataatg aaagcttatc ggggtggcat ccctgtgacc cctccccagt   660
gcctctcctg gccctggaag ttgccactcc agtgcccacc agccttgtcc taataaaatt   720
aagttgcatc attttgtctg actaggtgtc cttctataat attatggggt ggaggggggt   780
ggtatggagc aaggggcaag ttgggaagac aacctgtagg gctcgagggg gggcccggta   840
ccatgtgagc aaaaggccag caaaaggcca ggaaccgtaa aaaggccgcg ttgctggcgt   900
ttttccatag gctccgcccc cctgacgagc atcacaaaaa tcgacgctca agtcagaggt   960
ggcgaaaccc gacaggacta taaagatacc aggcgtttcc ccctggaagc tccctcgtgc   1020
gctctcctgt tccgaccctg ccgcttaccg gatacctgtc gcctttctc ccttcgggaa    1080 gcgtggcgct ttctcatagc tcacgctgta ggtatctcag ttcggtgtag gtcgttcgct   1140
ccaagctggg ctgtgtgcac gaaccccccg ttcagcccga ccgctgcgcc ttatccggta   1200
```

```
actatcgtct tgagtccaac ccggtaagac acgacttatc gccactggca gcagccactg   1260
gtaacaggat tagcagagcg aggtatgtag gcggtgctac agagttcttg aagtggtggc   1320
ctaactacgg ctacactaga agaacagtat ttggtatctg cgctctgctg aagccagtta   1380
ccttcggaaa aagagttggt agctcttgat ccggcaaaca aaccaccgct ggtagcggtg   1440 gttttttgt ttacaagcag catattacgc gcagaaaaaa aggatctcaa gaagatcctt   1500
tgatcttttc tacggggtct gacgctcagc tagcgctcag aagaactcgt caagaaggcg   1560
atagaaggcg atgcgctgcg aatcgggagc ggcgataccg taaagcacga ggaagcggtc   1620
agcccattcg ccgccaagct cttcagcaat atcacgggta gccaacgcta tgtcctgata   1680
gcggtccgcc acacccagcc ggccacagtc gatgaatcca gaaaagcggc cattttccac   1740
catgatattc ggcaagcagg catcgccatg agtcacgacg agatcctcgc cgtcgggcat   1800
gcgcgccttg agcctggcga acagttcggc tggcgcgagc ccctgatgct cttcgtccag   1860
atcatcctga tcgacaagac cggcttccat ccgagtacgt gctcgctcga tgcgatgttt   1920
cgcttggtgg tcgaatgggc aggtagccgg atcaagcgta tgcagccgcc gcattgcatc   1980
agccatgatg gatactttct cggcaggagc aaggtgagat gacaggagat cctgccccgg   2040
cacttcgccc aatagcagcc agtcccttcc cgcttcagtg acaacgtcga gcacagctgc   2100
gcaaggaacg cccgtcgtgg ccagccacga tagccgcgct gcctcgtcct gcagttcatt   2160
cagggcaccg gacaggtcgg tcttgacaaa aagaaccggg cgcccctgcg ctgacagccg   2220
gaacacggcg gcatcagagc agccgattgt ctgttgtgcc cagtcatagc cgaatagcct   2280
ctccacccaa gcggccggag aacctgcgtg caatccatct tgttcaatca tgcgaaacga   2340
tcctcatcct gtctcttgat cagatcttga tcccctgcgc catcagatcc ttggcggcaa   2400
gaaagccatc cagtttactt tgcagggctt cccaaccttac cagagggcg ccccagctgg   2460 caattccggt tcgcttgctg tccataaaac cgcccagtct gagct         2505
```

<210> SEQ ID NO 32
<211> LENGTH: 2505
<212> TYPE: DNA
<213> ORGANISM: Artificial Sequence
<220> FEATURE:
<223> OTHER INFORMATION: RNA II Promoter Mutation 2 in pAV0242 A > T at 1464.

<400> SEQUENCE: 32

```
ccaccgcggt ggcggccgtc cgccctcggc accatcctca cgacacccaa atatggcgac     60
gggtgaggaa tggtggggag ttattttttag agcggtgagg aaggtgggca ggcagcaggt    120
gttggcgctc taaaaataac tcccgggagt tattttttaga gcggaggaat ggtggacacc    180
caaatatggc gacggttcct caccgtcgc catatttggg tgtccgccct cggccggggc    240
cgcattcctg ggggccgggc ggtgctcccg cccgcctcga taaaggctc cggggccggc    300 ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctccaggac atcatgagca ggcagcaggg agagaggaac    600
caagagcaag gagcataatg aaagcttatc ggggtggcat ccctgtgacc cctccccagt    660
gcctctcctg gccctggaag ttgccactcc agtgcccacc agccttgtcc taataaaatt    720
```

| | |
|---|---|
| aagttgcatc attttgtctg actaggtgtc cttctataat attatggggt ggagggggt | 780 |
| ggtatggagc aagggggcaag ttgggaagac aacctgtagg gctcgagggg gggcccggta | 840 |
| ccatgtgagc aaaaggccag caaaaggcca ggaaccgtaa aaaggccgcg ttgctggcgt | 900 |
| ttttccatag gctccgcccc cctgacgagc atcacaaaaa tcgacgctca agtcagaggt | 960 |
| ggcgaaaccc gacaggacta taaagatacc aggcgtttcc ccctggaagc tccctcgtgc | 1020 |
| gctctcctgt tccgaccctg ccgcttaccg gatacctgtc cgcctttctc ccttcgggaa | 1080 |
| gcgtggcgct ttctcatagc tcacgctgta ggtatctcag ttcggtgtag gtcgttcgct | 1140 |
| ccaagctggg ctgtgtgcac gaacccccccg ttcagcccga ccgctgcgcc ttatccggta | 1200 |
| actatcgtct tgagtccaac ccggtaagac gacttatc gccactggca gcagccactg | 1260 |
| gtaacaggat tagcagagcg aggtatgtag gcggtgctac agagttcttg aagtggtggc | 1320 |
| ctaactacgg ctacactaga agaacagtat ttggtatctg cgctctgctg aagccagtta | 1380 |
| ccttcggaaa aagagttggt agctcttgat ccggcaaaca aaccaccgct ggtagcggtg | 1440 |
| gtttttttgt ttacaagcag cagtttacgc gcagaaaaaa aggatctcaa gaagatcctt | 1500 |
| tgatcttttc tacggggtct gacgctcagc tagcgctcag aagaactcgt caagaaggcg | 1560 |
| atagaaggcg atgcgctgcg aatcgggagc ggcgataccg taaagcacga ggaagcggtc | 1620 |
| agcccattcg ccgccaagct cttcagcaat atcacgggta gccaacgcta tgtcctgata | 1680 |
| gcggtccgcc acacccagcc ggccacagtc gatgaatcca gaaaagcggc cattttccac | 1740 |
| catgatattc ggcaagcagg catcgccatg agtcacgacg agatcctcgc cgtcgggcat | 1800 |
| gcgcgccttg agcctggcga acagttcggc tggcgcgagc cctgatgct cttcgtccag | 1860 |
| atcatcctga tcgacaagac cggcttccat ccgagtacgt gctcgctcga tgcgatgttt | 1920 |
| cgcttggtgg tcgaatgggc aggtagccgg atcaagcgta tgcagccgcc gcattgcatc | 1980 |
| agccatgatg gatactttct cggcaggagc aaggtgagat gacaggagat cctgccccgg | 2040 |
| cacttcgccc aatagcagcc agtcccttcc cgcttcagtg acaacgtcga gcacagctgc | 2100 |
| gcaaggaacg cccgtcgtgg ccagccacga tagccgcgct gcctcgtcct gcagttcatt | 2160 |
| cagggcaccg gacaggtcgg tcttgacaaa aagaaccggg cgcccctgcg ctgacagccg | 2220 |
| gaacacggcg gcatcagagc agccgattgt ctgttgtgcc cagtcatagc cgaatagcct | 2280 |
| ctccacccaa gcggccggag aacctgcgtg caatccatct tgttcaatca tgcgaaacga | 2340 |
| tcctcatcct gtctcttgat cagatcttga tcccctgcgc catcagatcc ttggcggcaa | 2400 |
| gaaagccatc cagtttactt tgcagggctt cccaaccttta ccagagggcg ccccagctgg | 2460 |
| caattccggt tcgcttgctg tccataaaac cgcccagtct gagct | 2505 |

<210> SEQ ID NO 33
<211> LENGTH: 2505
<212> TYPE: DNA
<213> ORGANISM: Artificial Sequence
<220> FEATURE:
<223> OTHER INFORMATION: RNA II Promoter Mutation 3 in pAV0242 T > A at 1465.

<400> SEQUENCE: 33

| | |
|---|---|
| ccaccgcggt ggcggccgtc cgccctcggc accatcctca cgacacccaa atatggcgac | 60 |
| gggtgaggaa tggtggggag ttattttttag agcggtgagg aaggtgggca ggcagcaggt | 120 |
| gttggcgctc taaaaataac tcccgggagt tatttttaga gcggaggaat ggtggacacc | 180 |
| caaatatggc gacggttcct cacccgtcgc catatttggg tgtccgccct cggccggggc | 240 |

```
cgcattcctg ggggccgggc ggtgctcccg cccgcctcga taaaaggctc cggggccggc    300
ggcggcccac gagctacccg gaggagcggg aggcgccaag cggatcccaa ggcccaactc    360
cccgaaccac tcagggtcct gtggacagct cacctagctg ccatggtgct ctgggtgttc    420
ttctttgtga tcctcaccct cagcaacagc tcccactgct ccccacctcc ccctttgacc    480
ctcaggatgc ggcggtatgc agatgccatc ttcaccaaca gctaccggaa ggtgctgggc    540
cagctgtccg cccgcaagct gctccaggac atcatgagca ggcagcaggg agagaggaac    600
caagagcaag gagcataatg aaagcttatc ggggtggcat ccctgtgacc cctccccagt    660
gcctctcctg gccctggaag ttgccactcc agtgcccacc agccttgtcc taataaaatt    720
aagttgcatc attttgtctg actaggtgtc cttctataat attatggggt ggagggggt     780
ggtatggagc aaggggcaag ttgggaagac aacctgtagg gctcgagggg gggcccggta    840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc cgcctttctc ccttcgggaa   1080
gcgtggcgct ttctcatagc tcacgctgta ggtatctcag ttcggtgtag gtcgttcgct   1140
ccaagctggg ctgtgtgcac gaaccccccg ttcagcccga ccgctgcgcc ttatccggta   1200
actatcgtct gagtccaacc cggtaagaca cgacttatcg ccactggcag cagccactg    1260
gtaacaggat tagcagagcg aggtatgtag gcggtgctac agagttcttg aagtggtggc   1320
ctaactacgg ctacactaga agaacagtat ttggtatctg cgctctgctg aagccagtta   1380
ccttcggaaa aagagttggt agctcttgat ccggcaaaca aaccaccgct ggtagcggtg   1440
gtttttttgt ttacaagcag cagaatacgc gcagaaaaaa aggatctcaa gaagatcctt   1500
tgatcttttc tacggggtct gacgctcagc tagcgctcag aagaactcgt caagaaggcg   1560
atagaaggcg atgcgctgcg aatcgggagc ggcgataccg taaagcacga ggaagcggtc   1620
agcccattcg ccgccaagct cttcagcaat atcacgggta gccaacgcta tgtcctgata   1680
gcggtccgcc acacccagcc ggccacagtc gatgaatcca gaaaagcggc cattttccac   1740
catgatattc ggcaagcagg catcgccatg agtcacgacg agatcctcgc cgtcgggcat   1800
gcgcgccttg agcctggcga acagttcggc tggcgcgagc cctgatgct cttcgtccag     1860
atcatcctga tcgacaagac cggcttccat ccgagtacgt gctcgctcga tgcgatgttt   1920
cgcttggtgg tcgaatgggc aggtagccgg atcaagcgta tgcagccgcc gcattgcatc   1980
agccatgatg gatactttct cggcaggagc aaggtgagat gacaggagat cctgccccgg   2040
cacttcgccc aatagcagcc agtcccttcc cgcttcagtg acaacgtcga gcacagctgc   2100
gcaaggaacg cccgtcgtgg ccagccacga tagccgcgct gcctcgtcct gcagttcatt   2160
cagggcaccg gacaggtcgg tcttgacaaa agaaccggg cgccctgcg ctgacagccg     2220
gaacacggcg gcatcagagc agccgattgt ctgttgtgcc cagtcatagc cgaatagcct   2280
ctccacccaa gcggccggag aacctgcgtg caatccatct tgttcaatca tgcgaaacga   2340
tcctcatcct gtctcttgat cagatcttga tccctgcgc catcagatcc ttggcggcaa     2400
gaaagccatc cagtttactt tgcagggctt cccaacctta ccagagggcg ccccagctgg   2460
caattccggt tcgcttgctg tccataaaac cgcccagtct gagct                   2505

<210> SEQ ID NO 34
<211> LENGTH: 2505
```

<210> TYPE: DNA
<213> ORGANISM: Artificial Sequence
<220> FEATURE:
<223> OTHER INFORMATION: RNA II Promoter Mutation 8 in pAV0242 G > T at
      1463, and A > T at 1464.

<400> SEQUENCE: 34

```
ccaccgcggt ggcggccgtc cgccctcggc accatcctca cgacacccaa atatggcgac      60
gggtgaggaa tggtgggag ttattttag agcggtgagg aaggtgggca ggcagcaggt       120
gttggcgctc taaaataac tcccgggagt tattttaga gcggaggaat ggtggacacc       180
caaatatggc gacggttcct cacccgtcgc catatttggg tgtccgccct cggccggggc     240
cgcattcctg ggggccgggc ggtgctcccg cccgcctcga taaaaggctc ggggccggc      300
ggcggcccac gagctacccg gaggagcggg aggcgccaag cggatcccaa ggcccaactc     360
cccgaaccac tcagggtcct gtggacagct cacctagctg ccatggtgct ctgggtgttc    420
ttctttgtga tcctcaccct cagcaacagc tcccactgct ccccacctcc ccctttgacc     480
ctcaggatgc ggcggtatgc agatgccatc ttcaccaaca gctaccggaa ggtgctgggc    540
cagctgtccg cccgcaagct gctccaggac atcatgagca ggcagcaggg agagaggaac    600
caagagcaag gagcataatg aaagcttatc ggggtggcat ccctgtgacc cctccccagt    660
gcctctcctg gccctggaag ttgccactcc agtgccacc agccttgtcc taataaaatt      720
aagttgcatc attttgtctg actaggtgtc cttctataat attatggggt ggagggggt      780
ggtatggagc aaggggcaag ttgggaagac aacctagg gctcgagggg gggcccggta      840
ccatgtgagc aaaaggccag caaaaggcca ggaaccgtaa aaaggccgcg ttgctggcgt    900
ttttccatag gctccgcccc cctgacgagc atcacaaaaa tcgacgctca agtcagaggt    960
ggcgaaaccc gacaggacta taaagatacc aggcgtttcc ccctggaagc tccctcgtgc   1020
gctctcctgt tccgaccctg ccgcttaccg gatacctgtc cgcctttctc ccttcgggaa   1080
gcgtggcgct ttctcatagc tcacgctgta ggtatctcag ttcggtgtag tcgttcgct    1140
ccaagctggg ctgtgtgcac gaaccccccg ttcagcccga ccgctgcgcc ttatccggta   1200
actatcgtct tgagtccaac ccggtaagac acgacttatc gccactggca gcagccactg   1260
gtaacaggat tagcagagcg aggtatgtag gcggtgctac agagttcttg aagtggtggc    1320
ctaactacgg ctacactaga agaacagtat ttggtatctg cgctctgctg aagccagtta    1380
ccttcggaaa aagagttggt agctcttgat ccggcaaaca aaccaccgct ggtagcggtg    1440
gtttttttgt ttacaagcag cattttacgc gcagaaaaaa aggatctcaa gaagatcctt    1500
tgatcttttc tacggggtct gacgctcagc tagcgctcag aagaactcgt caagaaggcg    1560
atagaaggcg atgcgctgcg aatcgggagc ggcgataccg taaagcacga ggaagcggtc    1620
agcccattcg ccgccaagct cttcagcaat atcacgggta gccaacgcta tgtcctgata    1680
gcggtccgcc acacccagcc ggccacagtc gatgaatcca gaaaagcggc cattttccac    1740
catgatattc ggcaagcagg catcgccatg agtcacgacg agatcctcgc cgtcgggcat    1800
gcgcgccttg agcctggcga acagttcggc tggcgcgagc cctgatgct cttcgtccag    1860
atcatcctga tcgacaagac cggcttccat ccgagtacgt gctcgctcga tgcgatgttt    1920
cgcttggtgg tcgaatgggc aggtagccgg atcaagcgta tgcagccgcc gcattgcatc    1980
agccatgatg gatactttct cggcaggagc aaggtgagat gacaggagat cctgccccgg    2040
cacttcgccc aatagcagcc agtcccttcc cgcttcagtg acaacgtcga gcacagctgc    2100
gcaaggaacg cccgtcgtgg ccagccacga tagccgcgct gcctcgtcct gcagttcatt    2160
```

```
cagggcaccg acaggtcgg tcttgacaaa agaaccggg cgccctgcg ctgacagccg    2220 gaacacggcg gcatcagagc agccgattgt ctgttgtgcc cagtcatagc cgaatagcct    2280
ctccacccaa gcggccggag aacctgcgtg caatccatct tgttcaatca tgcgaaacga    2340
tcctcatcct gtctcttgat cagatcttga tccctgcgc catcagatcc ttggcggcaa    2400
gaaagccatc cagtttactt tgcagggctt cccaaccta ccagagggcg cccagctgg    2460 caattccggt tcgcttgctg tccataaaac cgcccagtct gagct    2505

<210> SEQ ID NO 35
<211> LENGTH: 2505
<212> TYPE: DNA
<213> ORGANISM: Artificial Sequence
<220> FEATURE:
<223> OTHER INFORMATION: RNA II Promoter Mutation 9 in pAV0242 G > T at
      1463, and T > A at 1465.

<400> SEQUENCE: 35
ccaccgcggt ggcggccgtc cgccctcggc accatcctca cgacacccaa atatggcgac      60
gggtgaggaa tggtggggag ttatttttag agcggtgagg aaggtgggca ggcagcaggt     120
gttggcgctc taaaaataac tcccgggagt tatttttaga gcggaggaat ggtggacacc     180
caaatatggc gacggttcct cacccgtcgc catatttggg tgtccgccct cggccggggc     240
cgcattcctg ggggccgggc ggtgctcccg cccgcctcga taaaaggctc cggggccggc     300
ggcggcccac gagctacccg gaggagcggg aggcgccaag cggatcccaa ggcccaactc     360
cccgaaccac tcagggtcct gtggacagct cacctagctg ccatggtgct ctgggtgttc     420
ttctttgtga tcctcaccct cagcaacagc tcccactgct ccccacctcc ccctttgacc     480
ctcaggatgc ggcggtatgc agatgccatc ttcaccaaca gctaccggaa ggtgctgggc     540
cagctgtccg cccgcaagct gctccaggac atcatgagca ggcagcaggg agagaggaac     600
caagagcaag gagcataatg aaagcttatc ggggtggcat ccctgtgacc cctccccagt     660
gcctctcctg gccctggaag ttgccactcc agtgcccacc agccttgtcc taataaaatt     720
aagttgcatc attttgtctg actaggtgtc cttctataat attatgggt ggagggggt     780 ggtatggagc aaggggcaag ttgggaagac aacctagg gctcgagggg gggcccggta     840
ccatgtgagc aaaaggccag caaaaggcca ggaaccgtaa aaaggccgcg ttgctggcgt     900
ttttccatag gctccgcccc cctgacgagc atcacaaaaa tcgacgctca agtcagaggt     960
ggcgaaaccc gacaggacta taaagatacc aggcgtttcc ccctggaagc tccctcgtgc    1020
gctctcctgt tccgaccctg ccgcttaccg gatacctgtc cgcctttctc ccttcgggaa    1080
gcgtggcgct ttctcatagc tcacgctgta ggtatctcag ttcggtgtag tcgttcgct    1140 ccaagctggg ctgtgtgcac gaacccccg ttcagcccga ccgctgcgcc ttatccggta    1200
actatcgtct tgagtccaac ccggtaagac acgacttatc gccactggca gcagccactg    1260
gtaacaggat tagcagagcg aggtatgtag gcggtgctac agagttcttg aagtggtggc    1320
ctaactacgg ctacactaga agaacagtat ttggtatctg cgctctgctg aagccagtta    1380
ccttcggaaa aagagttggt agctcttgat ccggcaaaca aaccaccgct ggtagcggtg    1440
gtttttttgt ttacaagcag cataatacgc gcagaaaaaa aggatctcaa gaagatcctt    1500
tgatcttttc tacggggtct gacgctcagc tagcgctcag aagaactcgt caagaaggcg    1560
atagaaggcg atgcgctgcg aatcgggagc ggcgataccg taaagcacga ggaagcggtc    1620
agcccattcg ccgccaagct cttcagcaat atcacgggta gccaacgcta tgtcctgata    1680
```

```
gcggtccgcc acacccagcc ggccacagtc gatgaatcca gaaaagcggc catttttccac    1740 catgatattc ggcaagcagg catcgccatg agtcacgacg agatcctcgc cgtcgggcat    1800
gcgcgccttg agcctggcga acagttcggc tggcgcgagc ccctgatgct cttcgtccag    1860
atcatcctga tcgacaagac cggcttccat ccgagtacgt gctcgctcga tgcgatgttt    1920
cgcttggtgg tcgaatgggc aggtagccgg atcaagcgta tgcagccgcc gcattgcatc    1980
agccatgatg gatactttct cggcaggagc aaggtgagat gacaggagat cctgccccgg    2040
cacttcgccc aatagcagcc agtcccttcc cgcttcagtg acaacgtcga gcacagctgc    2100
gcaaggaacg cccgtcgtgg ccagccacga tagccgcgct gcctcgtcct gcagttcatt    2160
cagggcaccg gacaggtcgg tcttgacaaa agaaccggg cgcccctgcg ctgacagccg    2220
gaacacggcg gcatcagagc agccgattgt ctgttgtgcc cagtcatagc cgaatagcct    2280
ctccacccaa gcggccggag aacctgcgtg caatccatct tgttcaatca tgcgaaacga    2340
tcctcatcct gtctcttgat cagatcttga tcccctgcgc catcagatcc ttggcggcaa    2400
gaaagccatc cagtttactt tgcagggctt cccaacctta ccagagggcg ccccagctgg    2460
caattccggt tcgcttgctg tccataaaac cgcccagtct gagct    2505

<210> SEQ ID NO 36
<211> LENGTH: 659
<212> TYPE: DNA
<213> ORGANISM: Artificial Sequence
<220> FEATURE:
<223> OTHER INFORMATION: Baseline Optimized Origin of Replication.

<400> SEQUENCE: 36
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtggt    600
ttttttgttt acaagcagca gattacgcgc agaaaaaaag gatctcaaga agatcctt     659

<210> SEQ ID NO 37
<211> LENGTH: 659
<212> TYPE: DNA
<213> ORGANISM: Artificial Sequence
<220> FEATURE:
<223> OTHER INFORMATION: Opt ORI with RNA II Promoter Mut 1 in Ori
      G -> T (bp 621).

<400> SEQUENCE: 37
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg    120
cgaaacccga caggactata aagataccag gcgtttcccc ctggaagctc cctcgtgcgc    180
tctcctgttc cgaccctgcc gcttaccgga tacctgtccg cctttctccc ttcgggaagc    240
```

```
gtggcgcttt ctcatagctc acgctgtagg tatctcagtt cggtgtaggt cgttcgctcc    300
aagctgggct gtgtgcacga accccccgtt cagcccgacc gctgcgcctt atccggtaac    360
tatcgtcttg agtccaaccc ggtaagacac gacttatcgc cactggcagc agccactggt    420
aacaggatta gcagagcgag gtatgtaggc ggtgctacag agttcttgaa gtggtggcct    480
aactacggct acactagaag aacagtattt ggtatctgcg ctctgctgaa gccagttacc    540
ttcggaaaaa gagttggtag ctcttgatcc ggcaaacaaa ccaccgctgg tagcggtggt    600 tttttttgttt acaagcagca tattacgcgc agaaaaaaag gatctcaaga agatcctttt   659
```

<210> SEQ ID NO 38
<211> LENGTH: 659
<212> TYPE: DNA
<213> ORGANISM: Artificial Sequence
<220> FEATURE:
<223> OTHER INFORMATION: OptORI with RNA II Promoter Mut 2 in Ori
      A -> T (bp622).

<400> SEQUENCE: 38

```
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg   120
cgaaacccga caggactata aagataccag gcgtttcccc ctggaagctc cctcgtgcgc   180
tctcctgttc cgaccctgcc gcttaccgga tacctgtccg cctttctccc ttcgggaagc   240
gtggcgcttt ctcatagctc acgctgtagg tatctcagtt cggtgtaggt cgttcgctcc   300
aagctgggct gtgtgcacga accccccgtt cagcccgacc gctgcgcctt atccggtaac   360
tatcgtcttg agtccaaccc ggtaagacac gacttatcgc cactggcagc agccactggt   420
aacaggatta gcagagcgag gtatgtaggc ggtgctacag agttcttgaa gtggtggcct   480
aactacggct acactagaag aacagtattt ggtatctgcg ctctgctgaa gccagttacc   540
ttcggaaaaa gagttggtag ctcttgatcc ggcaaacaaa ccaccgctgg tagcggtggt   600 tttttttgttt acaagcagca gtttacgcgc agaaaaaaag gatctcaaga agatcctttt  659
```

<210> SEQ ID NO 39
<211> LENGTH: 659
<212> TYPE: DNA
<213> ORGANISM: Artificial Sequence
<220> FEATURE:
<223> OTHER INFORMATION: Opt. ORI with RNA II Promoter Mut 3 in Ori
      T -> A (bp 623).

<400> SEQUENCE: 39

```
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg   120
cgaaacccga caggactata aagataccag gcgtttcccc ctggaagctc cctcgtgcgc   180
tctcctgttc cgaccctgcc gcttaccgga tacctgtccg cctttctccc ttcgggaagc   240
gtggcgcttt ctcatagctc acgctgtagg tatctcagtt cggtgtaggt cgttcgctcc   300
aagctgggct gtgtgcacga accccccgtt cagcccgacc gctgcgcctt atccggtaac   360
tatcgtcttg agtccaaccc ggtaagacac gacttatcgc cactggcagc agccactggt   420
aacaggatta gcagagcgag gtatgtaggc ggtgctacag agttcttgaa gtggtggcct   480
aactacggct acactagaag aacagtattt ggtatctgcg ctctgctgaa gccagttacc   540
ttcggaaaaa gagttggtag ctcttgatcc ggcaaacaaa ccaccgctgg tagcggtggt   600
``` tttttttgttt acaagcagca gaatacgcgc agaaaaaaag gatctcaaga agatcctttt    659

<210> SEQ ID NO 40
<211> LENGTH: 659
<212> TYPE: DNA
<213> ORGANISM: Artificial Sequence
<220> FEATURE:
<223> OTHER INFORMATION: Opt. ORI w/ RNA II Pro Mut 8 in Ori  G -> T, &
      A -> T (bp 621, 622).

<400> SEQUENCE: 40
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg   120
cgaaacccga caggactata aagataccag gcgtttcccc ctggaagctc cctcgtgcgc   180
tctcctgttc cgaccctgcc gcttaccgga tacctgtccg cctttctccc ttcgggaagc   240
gtggcgcttt ctcatagctc acgctgtagg tatctcagtt cggtgtaggt cgttcgctcc   300
aagctgggct gtgtgcacga accccccgtt cagcccgacc gctgcgcctt atccggtaac   360
tatcgtcttg agtccaaccc ggtaagacac gacttatcgc cactggcagc agccactggt   420
aacaggatta gcagagcgag gtatgtaggc ggtgctacag agttcttgaa gtggtggcct   480
aactacggct acactagaag aacagtattt ggtatctgcg ctctgctgaa gccagttacc   540
ttcggaaaaa gagttggtag ctcttgatcc ggcaaacaaa ccaccgctgg tagcggtggt   600
tttttttgttt acaagcagca ttttacgcgc agaaaaaaag gatctcaaga agatcctttt   659

<210> SEQ ID NO 41
<211> LENGTH: 659
<212> TYPE: DNA
<213> ORGANISM: Artificial Sequence
<220> FEATURE:
<223> OTHER INFORMATION: Opt. ORI w/RNA II Pro Mut 9 in ori G > T, and
      T > A (bp 621, 623).

<400> SEQUENCE: 41
atgtgagcaa aaggccagca aaaggccagg aaccgtaaaa aggccgcgtt gctggcgttt    60
ttccataggc tccgcccccc tgacgagcat cacaaaaatc gacgctcaag tcagaggtgg   120
cgaaacccga caggactata aagataccag gcgtttcccc ctggaagctc cctcgtgcgc   180
tctcctgttc cgaccctgcc gcttaccgga tacctgtccg cctttctccc ttcgggaagc   240
gtggcgcttt ctcatagctc acgctgtagg tatctcagtt cggtgtaggt cgttcgctcc   300
aagctgggct gtgtgcacga accccccgtt cagcccgacc gctgcgcctt atccggtaac   360
tatcgtcttg agtccaaccc ggtaagacac gacttatcgc cactggcagc agccactggt   420
aacaggatta gcagagcgag gtatgtaggc ggtgctacag agttcttgaa gtggtggcct   480
aactacggct acactagaag aacagtattt ggtatctgcg ctctgctgaa gccagttacc   540
ttcggaaaaa gagttggtag ctcttgatcc ggcaaacaaa ccaccgctgg tagcggtggt   600
tttttttgttt acaagcagca taatacgcgc agaaaaaaag gatctcaaga agatcctttt   659

<210> SEQ ID NO 42
<211> LENGTH: 659
<212> TYPE: DNA
<213> ORGANISM: Artificial Sequence
<220> FEATURE:
<223> OTHER INFORMATION: Opt ORI concensus Seq for Mutations
<220> FEATURE:
<221> NAME/KEY: misc_feature
<222> LOCATION: (621)..(621)
<223> OTHER INFORMATION: Can be T or G.

```
<220> FEATURE:
<221> NAME/KEY: misc_feature
<222> LOCATION: (622)..(622)
<223> OTHER INFORMATION: Can be T or A.
<220> FEATURE:
<221> NAME/KEY: misc_feature
<222> LOCATION: (623)..(623)
<223> OTHER INFORMATION: Can be T or A.

<400> SEQUENCE: 42
atgtgagcaa aaggccagca aaaggccagg aaccgtaaaa aggccgcgtt gctggcgttt      60
ttccataggc tccgcccccc tgacgagcat cacaaaaatc gacgctcaag tcagaggtgg     120
cgaaacccga caggactata agataccag gcgtttcccc ctggaagctc cctcgtgcgc      180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtggcct     480
aactacggct acactagaag aacagtattt ggtatctgcg ctctgctgaa gccagttacc     540
ttcggaaaaa gagttggtag ctcttgatcc ggcaaacaaa ccaccgctgg tagcggtggt     600 tttttttgttt acaagcagca nnntacgcgc agaaaaaaag gatctcaaga agatcctttt    659

<210> SEQ ID NO 43
<211> LENGTH: 35
<212> TYPE: DNA
<213> ORGANISM: Artificial Sequence
<220> FEATURE:
<223> OTHER INFORMATION: 5' upper primer

<400> SEQUENCE: 43
ggtagctctt gatccggcaa acaaaccacc gctgg                                35

<210> SEQ ID NO 44
<211> LENGTH: 35
<212> TYPE: DNA
<213> ORGANISM: Artificial Sequence
<220> FEATURE:
<223> OTHER INFORMATION: 3' lower primer.

<400> SEQUENCE: 44
ccagcggtgg tttgtttgcc ggatcaagag ctacc                                35

<210> SEQ ID NO 45
<211> LENGTH: 25
<212> TYPE: DNA
<213> ORGANISM: Artificial Sequence
<220> FEATURE:
<223> OTHER INFORMATION: NheI primer

<400> SEQUENCE: 45
cgagttcttc tgagcgctag ctgag                                           25

<210> SEQ ID NO 46
<211> LENGTH: 25
<212> TYPE: DNA
<213> ORGANISM: Artificial Sequence
<220> FEATURE:
<223> OTHER INFORMATION: AlwNI primer.

<400> SEQUENCE: 46
```

```
cactggcagc agccactggt aacag                                          25
```

<210> SEQ ID NO 47
<211> LENGTH: 70
<212> TYPE: DNA
<213> ORGANISM: Artificial Sequence
<220> FEATURE:
<223> OTHER INFORMATION: Wild-type origin of replication subspecies.

<400> SEQUENCE: 47

```
gttttttgt ttacaagcag cagattacgc gcagaaaaaa aggatctcaa gaagatcctt     60
tgatcttttc                                                           70
```

<210> SEQ ID NO 48
<211> LENGTH: 70
<212> TYPE: DNA
<213> ORGANISM: Artificial Sequence
<220> FEATURE:
<223> OTHER INFORMATION: Origin of replication subspecies mutant 1

<400> SEQUENCE: 48

```
gttttttgt ttacaagcag catattacgc gcagaaaaaa aggatctcaa gaagatcctt     60
tgatcttttc                                                           70
```

<210> SEQ ID NO 49
<211> LENGTH: 70
<212> TYPE: DNA
<213> ORGANISM: Artificial Sequence
<220> FEATURE:
<223> OTHER INFORMATION: Origin of replication subspecies of mutant 2.

<400> SEQUENCE: 49

```
gttttttgt ttacaagcag cagtttacgc gcagaaaaaa aggatctcaa gaagatcctt     60
tgatcttttc                                                           70
```

<210> SEQ ID NO 50
<211> LENGTH: 70
<212> TYPE: DNA
<213> ORGANISM: Artificial Sequence
<220> FEATURE:
<223> OTHER INFORMATION: Origin of replication subspecies of mutant 3.

<400> SEQUENCE: 50

```
gttttttgt ttacaagcag cagaatacgc gcagaaaaaa aggatctcaa gaagatcctt     60
tgatcttttc                                                           70
```

<210> SEQ ID NO 51
<211> LENGTH: 70
<212> TYPE: DNA
<213> ORGANISM: Artificial Sequence
<220> FEATURE:
<223> OTHER INFORMATION: Origin of replication subspecies mutant 8.

<400> SEQUENCE: 51

```
gttttttgt ttacaagcag cattttacgc gcagaaaaaa aggatctcaa gaagatcctt     60
tgatcttttc                                                           70
```

<210> SEQ ID NO 52
<211> LENGTH: 70
<212> TYPE: DNA
<213> ORGANISM: Artificial Sequence
<220> FEATURE:
<223> OTHER INFORMATION: Origin of replication subspecies mutant 9.

```
<400> SEQUENCE: 52 gttttttttgt ttacaagcag cataatacgc gcagaaaaaa aggatctcaa gaagatcctt      60
tgatcttttc                                                              70

<210> SEQ ID NO 53
<211> LENGTH: 18
<212> TYPE: DNA
<213> ORGANISM: Artificial Sequence
<220> FEATURE:
<223> OTHER INFORMATION: Mutant 1 5' RNAII promoter primer.

<400> SEQUENCE: 53
gcagcatatt acgcgcag                                                     18

<210> SEQ ID NO 54
<211> LENGTH: 18
<212> TYPE: DNA
<213> ORGANISM: Artificial Sequence
<220> FEATURE:
<223> OTHER INFORMATION: Mutant 1 3' RNAII promoter primer.

<400> SEQUENCE: 54
ctgcgcgtaa tatgctgc                                                     18

<210> SEQ ID NO 55
<211> LENGTH: 18
<212> TYPE: DNA
<213> ORGANISM: Artificial Sequence
<220> FEATURE:
<223> OTHER INFORMATION: Mutant 2 5' RNAII promoter primer.

<400> SEQUENCE: 55
gcagcagttt acgcgcag                                                     18

<210> SEQ ID NO 56
<211> LENGTH: 19
<212> TYPE: DNA
<213> ORGANISM: Artificial Sequence
<220> FEATURE:
<223> OTHER INFORMATION: Mutant 2 3' RNAII promoter primer.

<400> SEQUENCE: 56
gcgcgtaaac tgctgcttg                                                    19

<210> SEQ ID NO 57
<211> LENGTH: 18
<212> TYPE: DNA
<213> ORGANISM: Artificial Sequence
<220> FEATURE:
<223> OTHER INFORMATION: Mutant 3 5' RNAII promoter primer.

<400> SEQUENCE: 57
gcagcagaat acgcgcag                                                     18

<210> SEQ ID NO 58
<211> LENGTH: 19
<212> TYPE: DNA
<213> ORGANISM: Artificial Sequence
<220> FEATURE:
<223> OTHER INFORMATION: Mutant 3 3' RNAII promoter primer.

<400> SEQUENCE: 58
gcgcgtattc tgctgcttg                                                    19
```

<210> SEQ ID NO 59
<211> LENGTH: 21
<212> TYPE: DNA
<213> ORGANISM: Artificial Sequence
<220> FEATURE:
<223> OTHER INFORMATION: Mutant 8 5' RNAII promoter primer.

<400> SEQUENCE: 59
caagcagcat tttacgcgca g                                             21

<210> SEQ ID NO 60
<211> LENGTH: 21
<212> TYPE: DNA
<213> ORGANISM: Artificial Sequence
<220> FEATURE:
<223> OTHER INFORMATION: Mutant 8 3' RNAII promoter primer.

<400> SEQUENCE: 60
ctgcgcgtaa aatgctgctt g                                             21

<210> SEQ ID NO 61
<211> LENGTH: 21
<212> TYPE: DNA
<213> ORGANISM: Artificial Sequence
<220> FEATURE:
<223> OTHER INFORMATION: Mutant 9 5' RNAII promoter primer.

<400> SEQUENCE: 61
caagcagcat aatacgcgca g                                             21

<210> SEQ ID NO 62
<211> LENGTH: 21
<212> TYPE: DNA
<213> ORGANISM: Artificial Sequence
<220> FEATURE:
<223> OTHER INFORMATION: Mutant 9 3' RNAII promoter primer.

<400> SEQUENCE: 62
ctgcgcgtat tatgctgctt g                                             21

<210> SEQ ID NO 63
<211> LENGTH: 26
<212> TYPE: DNA
<213> ORGANISM: Artificial Sequence
<220> FEATURE:
<223> OTHER INFORMATION: AlwNI universal forward primer.

<400> SEQUENCE: 63
gcagcagcca ctggtaacag gattag                                        26

<210> SEQ ID NO 64
<211> LENGTH: 25
<212> TYPE: DNA
<213> ORGANISM: Artificial Sequence
<220> FEATURE:
<223> OTHER INFORMATION: NheI universal reverse primer.

<400> SEQUENCE: 64
cgagttcttc tgagcgctag ctgag                                         25